(12) United States Patent
Cogan et al.

(10) Patent No.: US 7,531,560 B2
(45) Date of Patent: *May 12, 2009

(54) ANTI-CYTOKINE HETEROCYCLIC COMPOUNDS

(75) Inventors: Derek Cogan, Sandy Hook, CT (US); Matthew Russell Netherton, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 524 days.

This patent is subject to a terminal disclaimer.

(21) Appl. No.: 11/270,207

(22) Filed: Nov. 9, 2005

(65) Prior Publication Data

US 2006/0100204 A1     May 11, 2006

Related U.S. Application Data

(60) Provisional application No. 60/626,547, filed on Nov. 10, 2004.

(51) Int. Cl.
*A61K 31/41* (2006.01)
*A61K 31/415* (2006.01)
*C07D 233/00* (2006.01)
*C07D 249/04* (2006.01)

(52) U.S. Cl. .............. 514/359; 514/383; 514/385; 514/403; 548/255; 548/262.2; 548/300.1; 548/356.1

(58) Field of Classification Search ............. 514/359, 514/383, 385, 403; 548/255, 262.2, 300.1, 548/356.1
See application file for complete search history.

(56) References Cited

U.S. PATENT DOCUMENTS

| | | | |
|---|---|---|---|
| 4,816,469 A | 3/1989 | Bochis et al. |
| 4,847,257 A | 7/1989 | Hupe et al. |
| 5,045,543 A | 9/1991 | Hupe |
| 5,210,079 A | 5/1993 | Carini et al. |
| 5,210,092 A | 5/1993 | Oku et al. |
| 5,215,994 A | 6/1993 | Oku et al. |
| 5,254,546 A | 10/1993 | Ardecky et al. |
| 5,354,867 A | 10/1994 | Carini et al. |
| 5,723,483 A | 3/1998 | Labeeuw et al. |
| 5,861,406 A | 1/1999 | Wehrmann |
| 5,925,661 A | 7/1999 | Labeewu et al. |
| 5,932,590 A | 8/1999 | Ciccarone et al. |
| 5,939,449 A | 8/1999 | Labeeuw et al. |
| 5,965,579 A | 10/1999 | Labeeuw et al. |
| 5,977,134 A | 11/1999 | Ciccarone et al. |
| 6,022,307 A | 2/2000 | Salvati et al. |
| 6,121,305 A | 9/2000 | Obara et al. |
| 6,172,239 B1 | 1/2001 | Labeeuw et al. |
| 6,201,002 B1 | 3/2001 | Beere et al. |
| 6,300,356 B1 | 10/2001 | Segal et al. |
| 6,413,992 B1 | 7/2002 | Tisdell et al. |
| 6,562,843 B1 | 5/2003 | Bullington et al. |
| 6,576,652 B2 | 6/2003 | Remuzzi |
| 2001/0044445 A1 | 11/2001 | Bamaung et al. |
| 2002/0032184 A1 | 3/2002 | Corbau et al. |
| 2005/0004176 A1 | 1/2005 | Dyckman et al. |
| 2005/0153972 A1 * | 7/2005 | Cogan et al. ............ 514/252.05 |
| 2005/0245536 A1 | 11/2005 | Hao et al. |
| 2005/0256113 A1 * | 11/2005 | Cogan et al. ............. 514/230.5 |

FOREIGN PATENT DOCUMENTS

| | | |
|---|---|---|
| DE | 4302051 A1 | 7/1994 |
| WO | WO91/15206 | 10/1991 |
| WO | WO92/10097 | 6/1992 |
| WO | WO96/32382 | 10/1996 |
| WO | WO99/51580 | 10/1999 |
| WO | WO 00/24735 A1 | 5/2000 |
| WO | WO01/72714 A2 | 10/2001 |
| WO | WO 03/002910 | 1/2003 |
| WO | WO03/022820 A1 | 3/2003 |
| WO | WO 03/030902 A1 | 4/2003 |
| WO | WO 03/063781 A2 | 8/2003 |
| WO | WO2004/006906 A2 | 1/2004 |

OTHER PUBLICATIONS

Patani et al., Chem Rev, 1996, vol. 96 (8), pp. 3147-3176, especially p. 3170.*
English Translation for DE 43 02 051 A1.

* cited by examiner

*Primary Examiner*—Golam M M Shameem
*Assistant Examiner*—Susannah Chung
(74) *Attorney, Agent, or Firm*—Michael P. Morris; Mary-Ellen M. Devlin; Anthony P. Bottino

(57) ABSTRACT

Disclosed are compounds of formula (I)

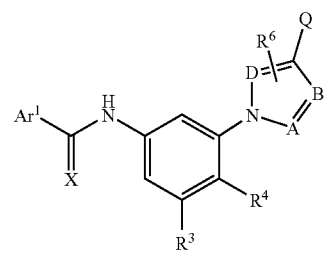

which inhibit production of cytokines involved in inflammatory processes and are thus useful for treating diseases and pathological conditions involving inflammation such as chronic inflammatory disease. Also disclosed are processes for preparing these compounds and pharmaceutical compositions comprising these compounds.

18 Claims, No Drawings

ANTI-CYTOKINE HETEROCYCLIC COMPOUNDS

APPLICATION DATA

This application claims priority to U.S. provisional application No. 60/626,547 filed Nov. 10, 2004.

TECHNICAL FIELD

This invention relates to compounds of formula (I)

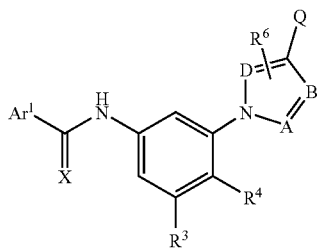

The compounds of the invention inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

BACKGROUND INFORMATION

Tumor necrosis factor (TNF) and interleukin-1 (IL-1) are important biological entities collectively referred to as proinflammatory cytokines which play a role in cytokine mediated diseases. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28-38). Studies suggest that inflammatory changes mediated by cytokines may be involved in endothelial cell pathogenesis including restenosis after percutaneous transluminal coronary angioplasty (PTCA) (Tashiro, H., et al., 2001 Mar, *Coron Artery Dis* 12(2):107-13). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24-5, 1997). These include the treatment of rheumatoid arthritis, Crohn's disease and ulcerative colitis (Rankin, E. C. C., et al., 1997, *British J. Rheum.* 35: 334-342 and Stack, W. A., et al., 1997, *Lancet* 349: 521-524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A,* 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines has been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses*, 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TNFα and IL-1β are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, *Ann. Emerg. Med.*, 35, 26). TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (El-hage et al., 1998, *Circulation*, 97, 242).

TNFα levels are elevated in airways of patients with chronic obstructive pulmonary disease and it may contribute to the pathogenesis of this disease (M. A. Higham et al., 2000, *Eur. Respiratory J.*, 15, 281). Circulating TNFα may also contribute to weight loss associated with this disease (N. Takabatake et al., 2000, *Amer. J. Resp. & Crit. Care Med.*, 161 (4 Pt 1), 1179). Elevated TNFα levels have also been found to be associated with congestive heart failure and the level has been correlated with severity of the disease (A. M. Feldman et al., 2000, *J. Amer. College of Cardiology*, 35, 537). In addition, TNFα has been implicated in reperfusion injury in lung (Borjesson et al., 2000, *Amer. J. Physiol.*, 278, L3-12), kidney (Lemay et al., 2000, *Transplantation*, 69, 959), and the nervous system (Mitsui et al., 1999, *Brain Res.*, 844, 192).

TNFα is also a potent osteoclastogenic agent and is involved in bone resorption and diseases involving bone resorption (Abu-Amer et al., 2000, *J. Biol. Chem.*, 275, 27307). It has also been found highly expressed in chondrocytes of patients with traumatic arthritis (Melchiorri et al., 2000, *Arthritis and Rheumatism*, 41, 2165). TNFα has also been shown to play a key role in the development of glomerulonephritis (Le Hir et al., 1998, *Laboratory Investigation*, 78, 1625).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867).

IL-1 has also been shown to induce uveitis in rats which could be inhibited with IL-1 blockers. (Xuan et al., 1998, *J. Ocular Pharmacol. and Ther.*, 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.*, 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including bum-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hematol.* 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma.* 19, 173). The development of insulin-dependent diabetes (Type 1) can be correlated with the accumulation in pancreatic islet cells of T-cells producing IFN γ (Ablumunits, et al., 1998, *J Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol.* 109, 342). The expression of a number of cytokines, including IFN γ has been shown to increase following a delayed type hypersensitivity reaction thus indicating a role for IFN γ in atopic dermatitis (Szepietowski, et al, 1997, *Br J Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol.* 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: rheumatoid arthritis, tumor associated osteolysis and post-menopausal osteoporosis (Evans, et al, 1996, *J Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 *Suppl* 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

WO 01/01986 discloses particular compounds alleged to having the ability to inhibit TNF-alpha. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalphathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. WO 02/32862 discloses that inhibitors of pro-inflammatory cytokines including TNFα are allegedly useful for treating acute and chronic inflammation in the lung caused by inhalation of smoke such as cigarette smoke. TNFα anatagonists are apparently also useful for the treatment of endometriosis, see EP 1022027 A1. Infliximab, in clinical trials for RA, has also been indicated to be useful for treating various inflammatory diseases including Behcet's disease, uveitis and ankylosing spondylitis. Pancreatitis may also be regulated by inflammatory mediator production, see J Surg Res 2000 May 15 90(2)95-101; Shock 1998 Sep. 10(3):160-75. p38MAP kinase pathway plays an role in *B. burgdorferi*-elicited infammation and may be useful in treating inflammation induced by the Lyme disease agent. Anguita, J. et. al., *The Journal of Immunology,* 2002, 168:6352-6357.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas and their use in treating cytokine diseases and proteolytic enzyme mediated disease. WO 00/41698 discloses aryl ureas said to be useful in treating p38 MAP kinase diseases.

Compounds active against p38 MAP kinase can also be useful for treating various types of cancers as described in WO 03/068223.

U.S. Pat. No. 5,162,360 discloses N-substituted aryl-N'-heterocyclic substituted urea compounds which are described as being useful for treating hypercholesterolemia and atheroclerosis. Di-substituted aryl and heteroaryl compounds are also disclosed in U.S. Pat. Nos. 6,080,763; 6,319,921; 6,297,381 and 6,358,945. The compounds in the patents are alleged to possess anti-cytokine activity and are therefore useful in treating diseases associated with inflammation.

The work cited above supports the principle that inhibition of cytokine production will be beneficial in the treatment of cytokine mediated diseases. Therefore a need exists for small molecule inhibitors for treating these diseases with optimized efficacy, pharmacokinetic and safety profiles.

BRIEF SUMMARY OF THE INVENTION

The work cited above supports the principle that inhibition of cytokine production with small molecule compounds will be beneficial in the treatment of various disease states.

It is therefore an object of the invention to provide compounds of formula (I)

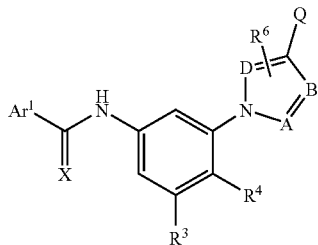

It is a further object of the invention to provide methods for treating cytokine mediated diseases and pathological conditions involving inflammation such as chronic inflammatory disease, using the novel compounds of the invention.

It is yet a further object of the invention to provide pharmaceutical compositions and processes of preparation of the above-mentioned novel compounds.

DETAILED DESCRIPTION OF THE INVENTION

In the broadest generic embodiment, there is provided compounds of the formula (I)

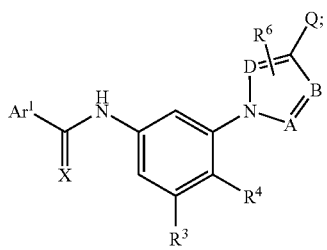

(I)

wherein:

$Ar^1$ is chosen from (i), (ii), (iii) and (iv) below:

i) a carbocycle independently substituted by one or more of $R^1$, $R^2$ and $R^x$, (ii)

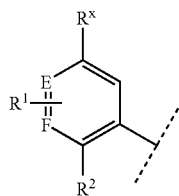

wherein one of E or F is nitrogen and the other is carbon, $R^1$ is covalently attached to either E or F, and when nitrogen is $N-R^1$ the double bond between E and F is not present;

(iii)

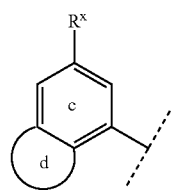

wherein c is a benzo ring fused to ring d which is a 5-7 membered heterocyclic ring optionally substituted by an oxo (=O) group and one to two R groups each independently being H or C1-3 alkyl;

(iv) a 5 membered nitrogen containing heteroaryl or heterocyclic ring optionally substituted by $R^1$ or $R^x$;

$R^1$ is chosen from hydrogen, $NO_2$, $-N(R^c)_2$, $J-C(O)-N(R^c)-$, $J-S(O)_m-N(R^c)-$, $C1-6$ alkyl$S(O)_m-$ or $R^1$ is chosen from C1-6 alkyl, C3-7 cylcoalkyl, C1-5 alkoxyl or C3-7 cycloalkoxyl, C1-5 alkylthiol or C3-7 cycloalkylthiol, C1-5 acyl, C1-5 alkoxycarbonyl, C1-5 acyloxy, C1-5 acylamino, C2-5 alkenyl, C2-5 alkynyl, heterocycle, aryl, heterocycleC1-6 alkyl, heteroaryl, heteroarylC1-6 alkyl and nitrile; each of the aforementioned where possible are optionally partially or fully halogenated or are optionally further substituted with alkylsulfonylamino, aminocarboxyl, alkoxyl, amino, alkylamino, dialkylamino, hydroxyl, oxo, nitro or nitrile;

$R^2$ is chosen from:

hydrogen, halogen, nitrile, C1-5 alkyl$S(O)_m-$, aryl$S(O)_m$, $J-O-C(O)-O-$, $N(R^c)_2-C(O)-(CH_2)_n-$, C1-6 acetyl, aroyl, C1-6alkoxycarbonyl, C1-6 alkyl, C3-7cycloalkyl, C1-6 alkoxy, C3-5cycloalkoxy, C1-5 alkylC1-5 alkoxy, hydroxy, hydroxy C1-5 alkyl, and amino optionally mono- or di-substituted by C1-5 alkyl, aryl or aryl C1-5 alkyl; each of the aforementioned where possible are optionally partially or fully halogenated or are optionally further substituted with C1-3 alkyl, alkylsulfonylamino, alkoxyl, amino, alkylamino, dialkylamino, hydroxyl, oxo, nitro or nitrile;

each $R^x$ is chosen from C1-6 alkyl or C3-7 cycloalkyl each being optionally substituted by C1-3 alkyl and optionally partially or fully halogenated, C1-4 acyl, aroyl, C1-4 alkoxy, C1-5alkyl$S(O)_m-$, each may optionally be partially or fully halogenated, halogen, C1-6 alkoxycarbonyl, carbocyclesulfonyl;

each R$^c$ is independently hydrogen or C1-5 alkyl;
D, A and B in

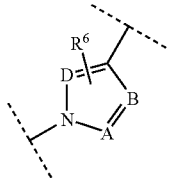

of the formula (I) are each independently chosen from N or CH wherein the hydrogen atom is optionally replaced by R$^6$;
Q is —C(O)—R$^5$ or Het,
Het is a heterocyclic or heteroaryl ring wherein Het is optionally substituted by one to three R$^5$;
m is 0, 1 or 2
J is chosen from C1-10 alkyl and C3-7cycloalkyl each optionally substituted by R$^b$;
R$^3$, R$^4$, R$^6$, R$^7$ and R$^8$ are each independently chosen from hydrogen, halogen, C1-5 alkyl, C1-5 alkoxy, C1-5 alkylC1-5 alkoxy, hydroxy, hydroxy C1-5 alkyl or amino optionally mono- or di-substituted by C1-5 alkyl, aryl or aryl C1-5 alkyl;
R$^5$ is:
R$^a$, —O—R$^a$, —S(O)$_m$—R$^a$, —N(R$^a$)$_2$, —C(O)—R$^a$, —NH(CR$^7$R$^8$)$_n$—R$^a$, N(R$^a$)$_2$—(CH$_2$)$_{1-2}$— —(CR$^7$R$^8$)$_n$—R$^a$, O(CR$^7$R$^8$)$_n$—R$^a$, —C(O)—O(CR$^7$R$^8$)$_n$—R$^a$, —C(O)(CR$^7$R$^8$)$_n$—R$^a$—C(O)C(O)R$^a$, —C(O)C(O)OR$^a$, —C(O)NHR$^a$, and —C(O)NH(CR$^7$R$^8$)$_n$—, each optionally substituted by C1-3 alkyl, halogen or hydroxy,
wherein n is 1-5;
R$^a$ and R$^b$ are each independently chosen from hydrogen, C1-6 alkyl, hydroxyC1-5 alkyl, C2-5 alkenyl, C2-5 alkynyl, carbocycle, carbocycleC0-2 alkyl, aryl, heterocycle, heteroaryl, C1-5 alkoxy, C1-5 alkylthio, amino, C1-5 alkylamino, C1-5 dialkylamino, arylamino, aryl C1-5 alkylamino, diarylamino, C1-5 acyl, C1-5 alkoxycarbonyl, C1-5 acyloxy, C1-5 acylamino, each of the aforementioned are optionally partially or fully halogenated, or R$^a$ and R$^b$ are chosen from C1-5 alkylsulphonylamino, hydroxy, oxo, halogen, —CF$_3$, —CH$_2$—CF$_3$, nitro and nitrile, wherein each carbocycle, heterocycle or heteroaryl for R$^a$ and R$^b$ is optionally substituted by amino, C1-3 alkyl, halogen or hydroxy;
and
X is O or S
or the pharmaceutically acceptable salts, acids, esters or isomers thereof.

In a first subgeneric aspect of the invention, there are provided compounds of the formula (I) as described above and wherein
Q is Het;

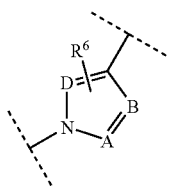

of the formula (I) is chosen from:

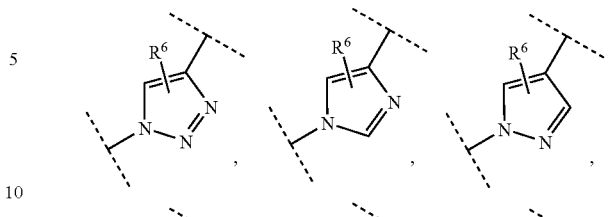

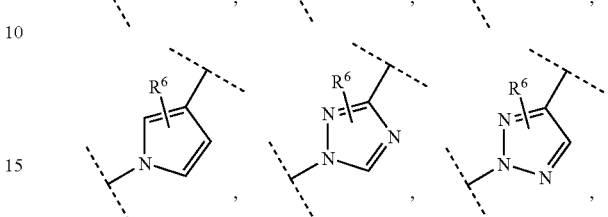

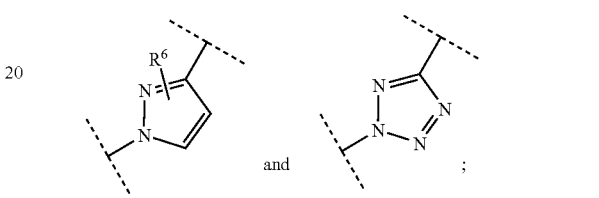

Het is

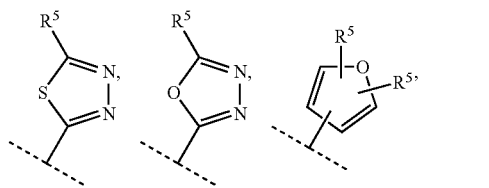

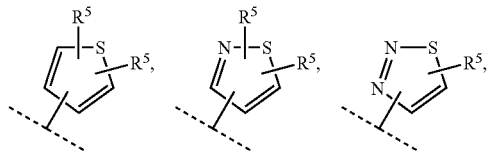

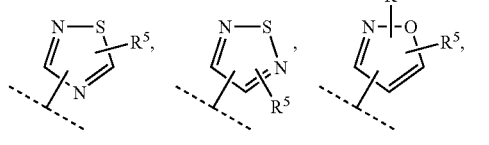

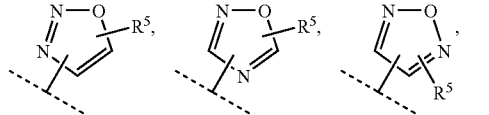

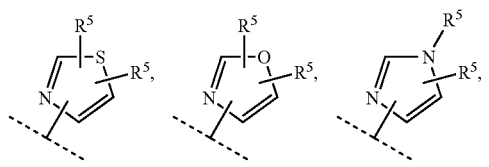

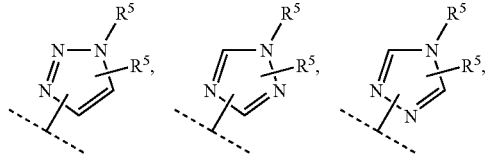

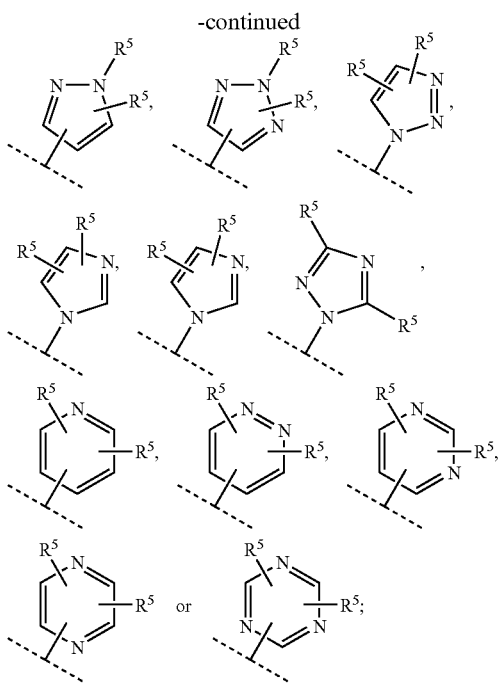

J is chosen from C1-10 alkyl, aryl and C3-7 cycloalkyl each optionally substituted by $R^b$;

$R^2$ is independently chosen from hydrogen, J-O—C(O)—O—, C1-6 alkoxy, C1-6 alkyl, C1-6 acetyl, aroyl, halogen, methoxycarbonyl, phenylsulfonyl, C1-5 alkylS(O)$_m$— and C3-7 cycloalkyl optionally substituted by C1-3 alkyl, each $R^2$ where possible may be optionally partially or fully halogenated;

$R^1$ is chosen from H, C1-6 alkyl, phenyl, C1-5 alkylS(O)$_m$—, J-S(O)$_m$—N($R^c$)—, C1-5 alkoxyl, C1-5 alkylthiol, NH$_2$—C(O)—(CH$_2$)$_n$—, ($R^c$)$_2$N C1-6 alkyl, C1-5acylNH—, —NH$_2$, —NO$_2$, heteroaryl chosen from pyrazole, triazole, imidazole and tetrazole, and nitrile;

ring d is a 5-6 membered heterocyclic ring such that rings c and d fuse to form the following:

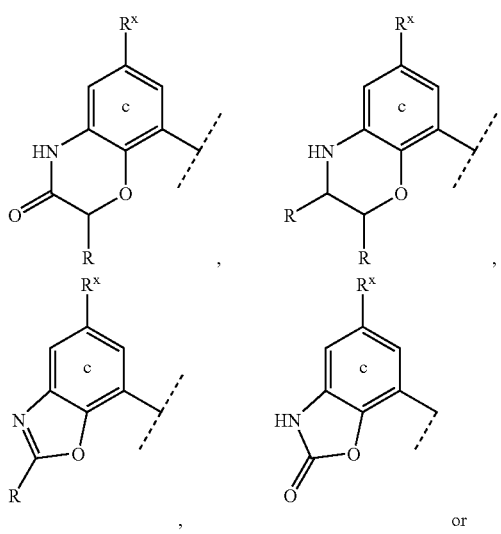

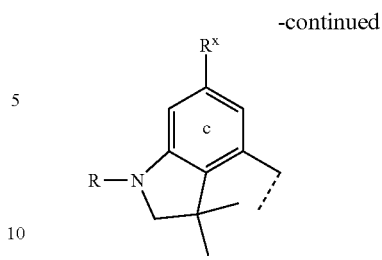

where each R is independently H or C1-3 alkyl;

if Ar is (iv) then Ar is pyrazolyl optionally substituted by $R^1$ or $R^x$;

$R^3$ and $R^4$ are each independently chosen from hydrogen, C1-3 alkoxy, C1-3 alkyl and halogen;

n is 1-4;

$R^a$ and $R^b$ are each independently chosen from hydrogen, C1-6 alkyl, C2-5 alkenyl, C2-5 alkynyl, C3-8 cycloalkylC0-2 alkyl, aryl, C1-5 alkoxy, C1-5 alkylthio, amino, C1-5 alkylamino, C1-5 dialkylamino, arylamino, C1-5 acyl, C1-5 alkoxycarbonyl, C1-5 acyloxy, C1-5 acylamino, aryl C1-5alkylamino, C1-5 alkylsulphonylamino, hydroxy, halogen, —CF$_3$, —CH$_2$—CF$_3$ nitro, nitrile, or $R^a$ and $R^b$ are chosen from; heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, homopiperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, aziridinyl, pentamethylene sulfide, pentamethylene sulfoxide, pentamethylene sulfone, tetramethylene sulfide, tetramethylene sulfoxide and tetramethylene sulfone and heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl; wherein each aryl, heterocycle or heteroaryl for $R^a$ and $R^b$ is optionally substituted by amino, C1-3 alkyl, halogen or hydroxy;

and X is O.

In yet another embodiment, there are provided compounds of the formula (I) as described immediately above and wherein $Ar^1$ is chosen from (i), (ii) and (iv);

wherein if $Ar^1$ is (iv) then $Ar^1$ is

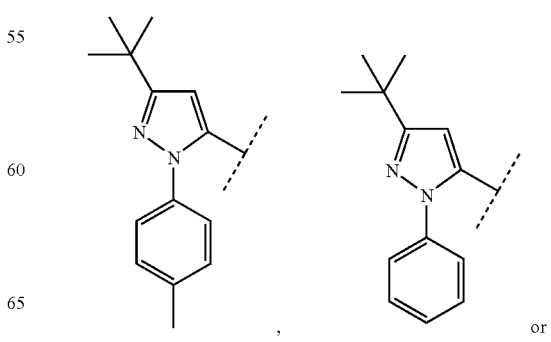

-continued

[structure: 3-tert-butyl-1-methyl-1H-pyrazol-5-yl group]

R⁵ is:
a) $R^a$, —O—$R^a$, —S(O)$_m$—$R^a$, —N($R^a$)$_2$, N($R^a$)$_2$—(CH$_2$)$_{1-2}$—, —NH(CR⁷R⁸)$_n$—$R^a$, —(CR⁷R⁸)$_n$—$R^a$ or —O(CR⁷R⁸)$_n$—$R^a$;
or R⁵ is:
b) —C(O)—$R^a$, —C(O)—O(CR⁷R⁸)$_n$—$R^a$, —C(O)(CR⁷R⁸)$_n$—$R^a$, —C(O)NHR$^a$, —C(O)NH(CR⁷R⁸)$_n$—, —C(O)C(O)R$^a$ or —C(O)C(O)OR$^a$;
each of the above R⁵ is optionally substituted by C1-3 alkyl, halogen or hydroxyl, and wherein n is 1-3

In yet another embodiment, there are provided compounds of the formula (I) as described immediately above and wherein
Ar¹ is:

[structure: pyridine with Rx, R²]

or Ar¹ is cyclopropyl, cyclobutyl, phenyl, naphthyl, tetrahydronaphthyl, indanyl and indenyl each independently substituted with one or more of R¹, $R^x$, and R²;
R¹ is nitrile, NO$_2$, NH$_2$, C1-3acylNH—,
J-S(O)$_m$—N(R$^c$)— where J is C1-10 alkyl, or R¹ is

[structure: R$^c$—N(R$^c$)—CH$_2$—]

R² is independently chosen from C1-6 alkyl, C1-6 alkyl S(O)$_m$—, C1-3 alkoxy and C3-6 cycloalkyl optionally substituted by C1-3 alkyl, each may optionally be partially or fully halogenated;
R³ and R⁴ are each independently chosen from hydrogen, C1-3 alkyl, fluoro and chloro;
R⁶ is chosen from hydrogen and amino;
n is 1-2;
$R^a$ and $R^b$ are each independently chosen from hydrogen, C1-6 alkyl, C3-7 cycloalkylC0-2 alkyl, aryl, C1-5 alkoxy, amino, C1-5 alkylamino, C1-5 dialkylamino, arylamino, aryl C1-5alkylamino, C1-3 acyl, C1-5 alkoxycarbonyl, C1-5 acyloxy, C1-5 acylamino, C1-5 sulphonylamino, hydroxy, halogen, —CF$_3$, —CH$_2$—CF$_3$ nitro, nitrile;
or $R^a$ is chosen from pyrrolidinyl, pyrrolinyl, morpholinyl, thiomorpholinyl, thiomorpholinyl sulfoxide, thiomorpholinyl sulfone, piperidinyl, piperazinyl, homopiperazinyl, piperidinonyl, tetrahydropyrimidonyl, aziridinyl, isoxazolyl, oxazolyl, thiazolyl, thiadiazolyl, tetrazolyl, pyrazolyl, pyrrolyl, imidazolyl, pyridinyl, pyrimidinyl, pyrazinyl and pyridazinyl; wherein each aryl, heterocycle or heteroaryl for $R^a$ and $R^b$ is optionally substituted by amino, C1-3 alkyl, halogen or hydroxy.

In yet still another embodiment, there are provided compounds of the formula (I) as described immediately above and wherein
Ar¹ is

[structures: substituted phenyl and pyridine groups with Rx, R¹, R²; and cyclopropyl-tert-butyl group]

substituted by one or more of R¹, R² and $R^x$;
R¹ is:
J-S(O)$_2$—NH—, where J is C1-5 alkyl,
or R¹ is nitrile, NO$_2$, NH$_2$ or C1-3acylNH—;
wherein $R^x$=$R^2$ each are independently chosen from C1-5 alkyl, C1-5 alkylS(O)$_m$—, C1-4 alkoxy and and C3-5 cycloalkyl optionally substituted by C1-2 alkyl, each may optionally be partially or fully halogenated;
R⁸ is hydrogen, methyl, ethyl, CH$_2$OH and CH$_2$OCH$_3$.

In yet another embodiment, there are provided compounds of the formula (I) as described immediately above and wherein
$R^a$ is chosen from hydrogen, C1-6 alkyl, C3-6 cycloalkylC0-2 alkyl, phenyl, C1-5 alkoxy, amino, C1-5 alkylamino, C1-5 dialkylamino, arylamino, aryl C1-5alkylamino, C1-3 acyl, C1-5 alkoxycarbonyl, C1-5 acyloxy, C1-5 acylamino, hydroxy, halogen, —CF$_3$, —CH$_2$—CF$_3$;
or $R^a$ is chosen from morpholinyl, thiomorpholinyl, thiomorpholinyl sulfoxide, thiomorpholinyl sulfone, piperazinyl, homopiperazinyl, pyrrolidinyl, piperidinyl, piperidinonyl, pyridinyl, pyrimidinyl, pyrazinyl and pyridazinyl wherein each phenyl, heterocycle or heteroaryl for $R^a$ is optionally substituted by amino, C1-3 alkyl, halogen or hydroxy.

In yet another embodiment, there are provided compounds of the formula (I) as described immediately above and wherein
$R^a$ is chosen from hydrogen, C1-6 alkyl, C3-6 cycloalkyl, phenyl, C1-5 alkoxy, C1-5 alkoxycarbonyl, amino, C1-5 alkylamino, C1-5 dialkylamino, arylamino, aryl C1-5alkylamino, C1-5 acyloxy, C1-5 acylamino, hydroxy, halogen, —CF$_3$, —CH$_2$—CF$_3$;
or $R^a$ is chosen morpholinyl, piperidinyl piperazinyl, homopiperazinyl, pyrrolidinyl and pyridinyl wherein each phenyl, heterocycle or heteroaryl for $R^a$ is optionally substituted by amino, C1-3 alkyl, halogen or hydroxy.

In yet another embodiment, there are provided compounds of the formula (I) as described immediately above and wherein

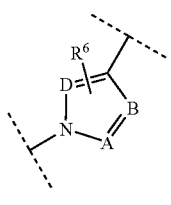
of the formula (I) is chosen from:
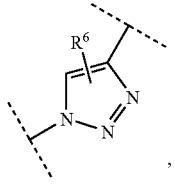 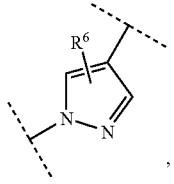
and
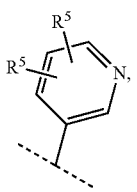
Het is;
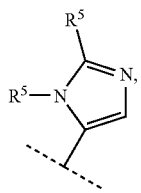 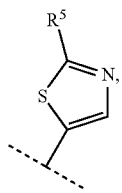 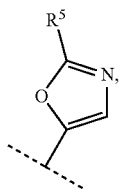
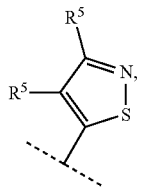 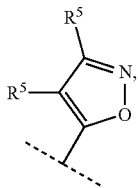 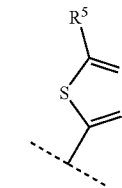
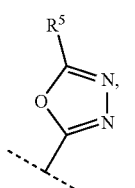 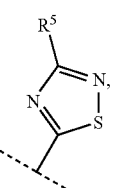 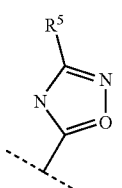
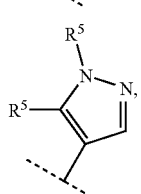 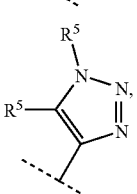 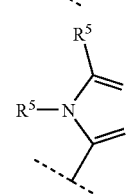
-continued
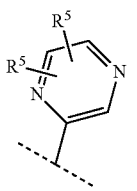 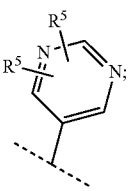
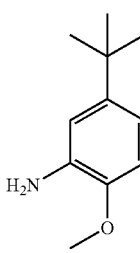 or 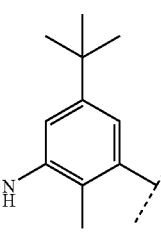
$Ar^1$ is
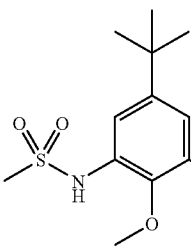 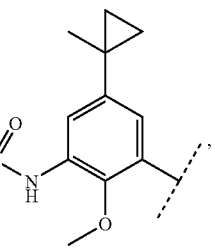
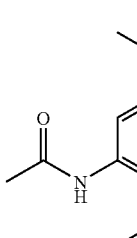 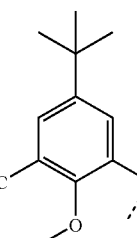
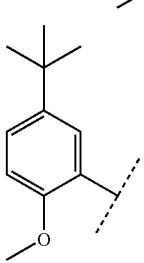 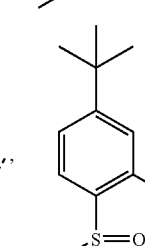

-continued
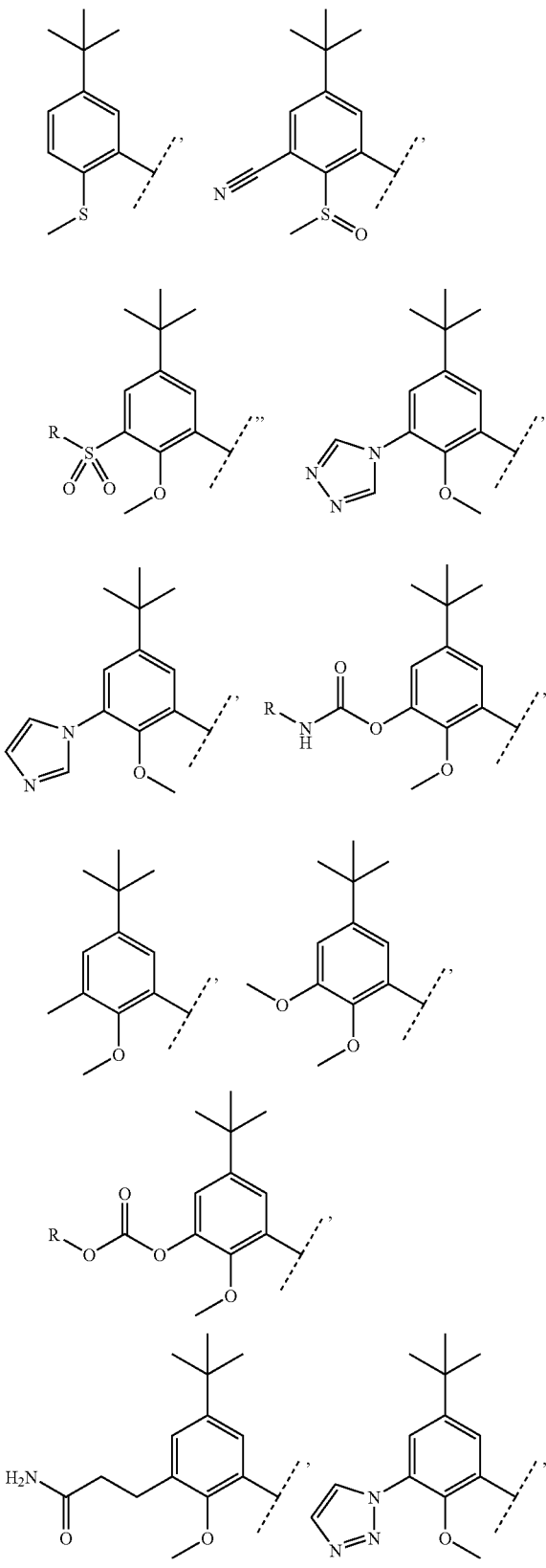
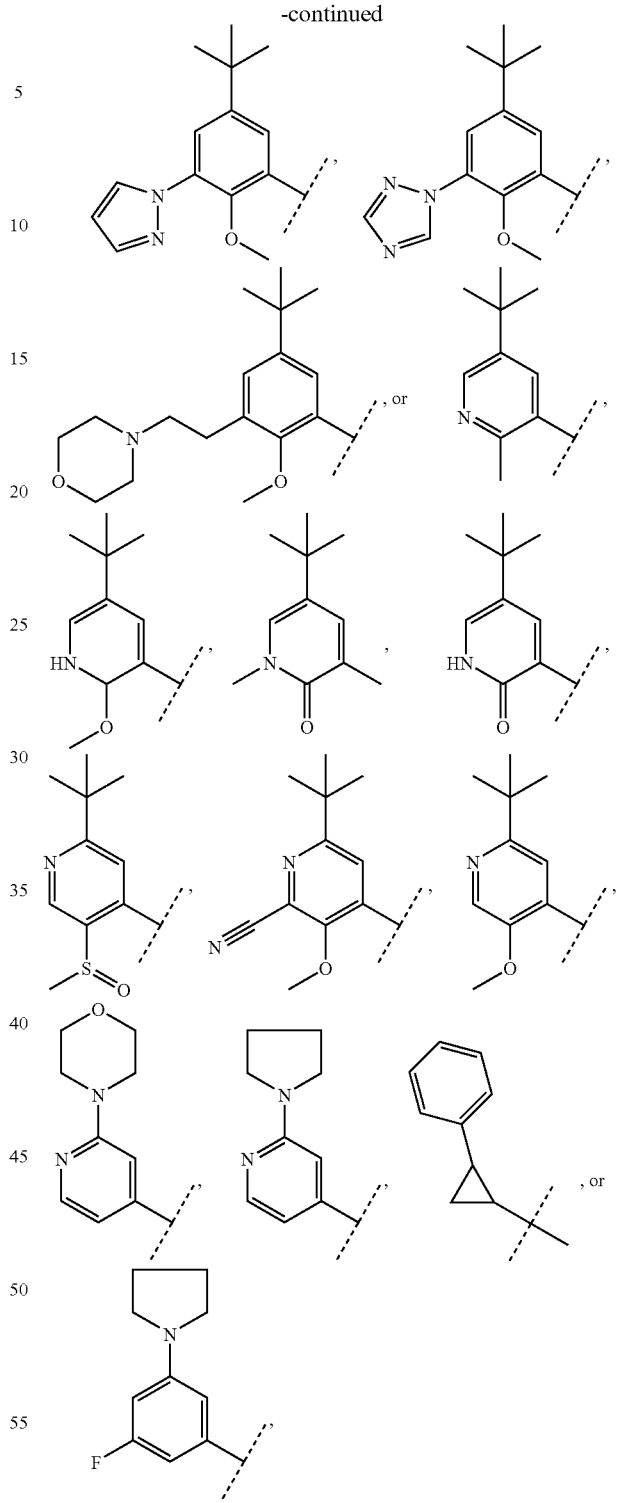
wherein R is as hereinabove described;
R⁵ is:
C1-5 alkyl, C3-6 cycloalkyl, $N(R^a)_2(CH_2)_{1-2}$—, halogen, C1-3 alkoxy, hydroxy, —$N(R^a)_2$, —$CF_3$, —$CH_2$—$CF_3$, aryl, —$S(O)_m$—$R^a$, —$NH(CR^7R^8)_n$—$R^a$ or —$(CR^7R^8)_n$—$N(R^a)_2$ each optionally substituted by C1-3 alkyl, halogen or hydroxy, or R⁵ is —C(O)Rᵃ, —C(O)C(O)Rᵃ, —C(O)NHRᵃ.

Rᵃ is chosen from hydrogen, morpholinyl, piperidinyl, piperazinyl, pyrrolidinyl, pyridinyl, C₁₋₅ mono or dialkylamino, arylamino, C3-6cylcoalkyl, C1-5 alkyl and C1-3 alkoxy wherein each phenyl or heterocycle for Rᵃ is optionally substituted by amino, C1-3 alkyl, halogen or hydroxyl.

The following are preferred embodiments of Het combined with

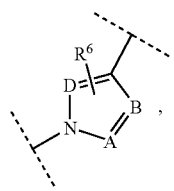

and wherein Ar¹, X, R³, R⁴ of the formula (I) are as defined in any one of the first seven embodiments provided hereinabove and wherein:

i) Het is

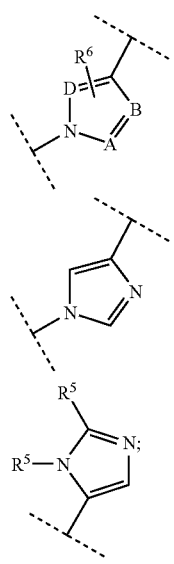 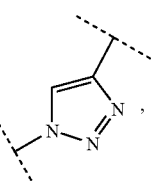 is 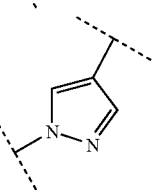

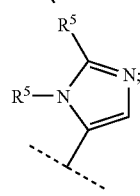 or 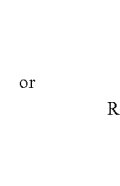...

ii) Het is

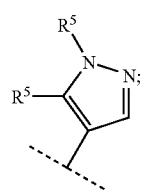

iii) Het is

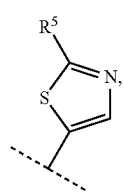 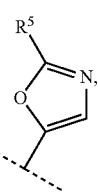 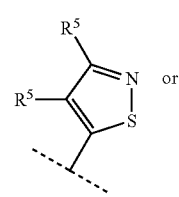 or iv) Het is

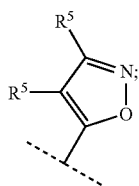

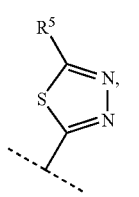 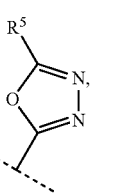 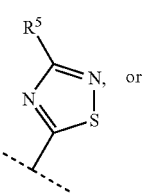 or

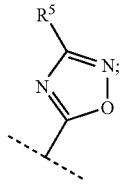

v) Het is

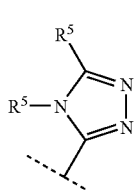 or 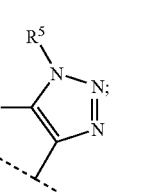

vi) Het is

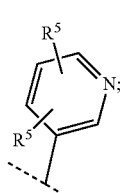

or vii) Het is

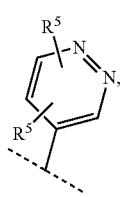 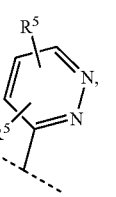 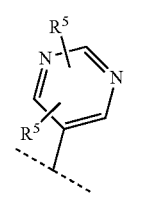 or

-continued

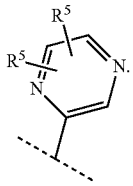

In a second subgeneric aspect of the invention, there are provided compounds of the formula (I) as described above and wherein Q is —C(O)—$R^5$;

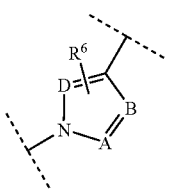

of the formula (I) is chosen from:

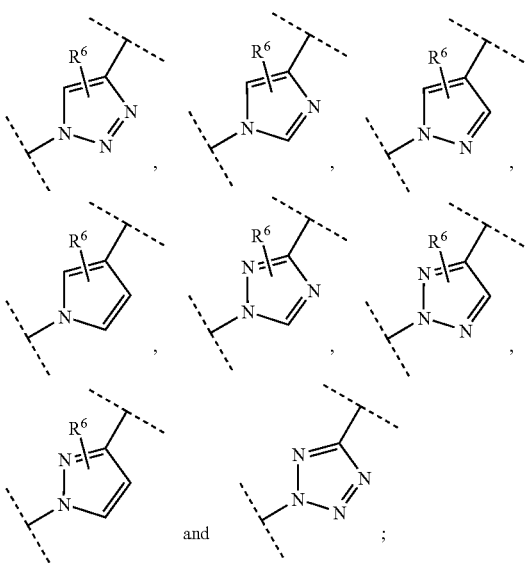

J is chosen from C1-10 alkyl, aryl and C3-7 cycloalkyl each optionally substituted by $R^b$;

$R^2$ is independently chosen from hydrogen, J-O—C(O)—O—, C1-6 alkoxy, C1-6 alkyl, C1-6 acetyl, aroyl, halogen, methoxycarbonyl, phenylsulfonyl, C1-5 alkylS(O)$_m$— and C3-7 cycloalkyl optionally substituted by C1-3 alkyl, each $R^2$ where possible may be optionally partially or fully halogenated;

$R^1$ is chosen from H, C1-6 alkyl, phenyl, C1-5 alkylS(O)$_m$—, J-S(O)$_m$—N($R^c$)—, C1-5 alkoxyl, C1-5 alkylthiol, NH$_2$—C(O)—(CH$_2$)$_n$—, ($R^c$)$_2$N C1-6 alkyl, C1-5acylNH—, —NH$_2$, —NO$_2$, heteroaryl chosen from pyrazole, triazole, imidazole and tetrazole, and nitrile;

ring d is a 5-6 membered heterocyclic ring such that rings c and d fuse to form the following:

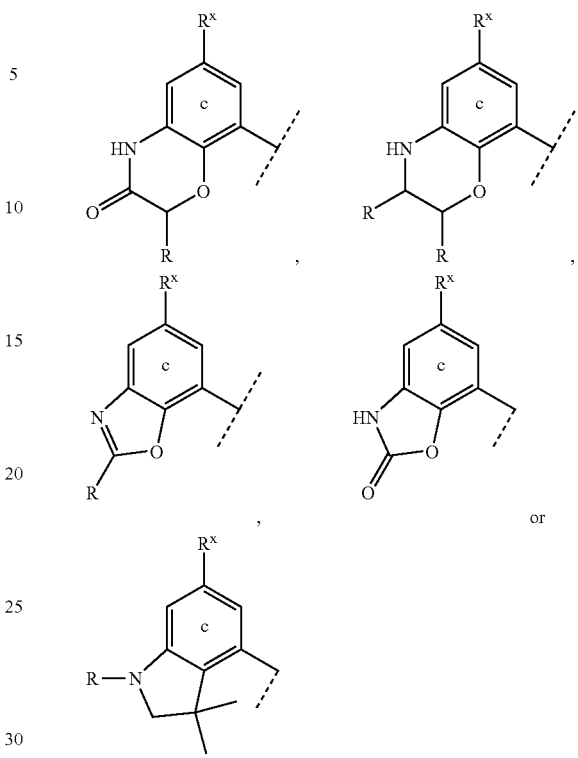

where each R is independently H or C1-3 alkyl;

if Ar is (iv) then Ar is pyrazolyl optionally substituted by $R^1$ or $R^x$;

$R^3$ and $R^4$ are each independently chosen from hydrogen, C1-3 alkoxy, C1-3 alkyl and halogen;

n is 1-4;

$R^a$ and $R^b$ are each independently chosen from hydrogen, C1-6 alkyl, C2-5 alkenyl, C2-5 alkynyl, C3-8 cycloalkylC0-2 alkyl, aryl, C1-5 alkoxy, C1-5 alkylthio, amino, C1-5 alkylamino, C1-5 dialkylamino, arylamino, C1-5 acyl, C1-5 alkoxycarbonyl, C1-5 acyloxy, C1-5 acylamino, aryl C1-5alkylamino, C1-5 alkylsulphonylamino, hydroxy, halogen, —CF$_3$, —CH$_2$—CF$_3$ nitro, nitrile, or $R^a$ and $R^b$ are chosen from; heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, homopiperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, aziridinyl, pentamethylene sulfide, pentamethylene sulfoxide, pentamethylene sulfone, tetramethylene sulfide, tetramethylene sulfoxide and tetramethylene sulfone and heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl; wherein each aryl, heterocycle or heteroaryl for $R^a$ and $R^b$ is optionally substituted by amino, C1-3 alkyl, halogen or hydroxy;

and X is O.

In yet another embodiment, there are provided compounds of the formula (I) as described immediately above and wherein Ar¹ is chosen from (i), (ii) and (iv);
wherein if Ar¹ is (iv) then Ar¹ is

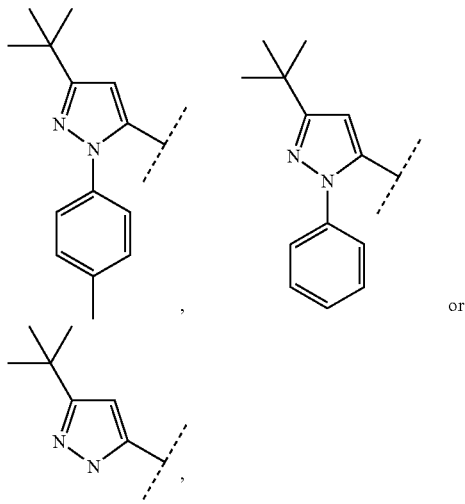

, or

,

R⁵ is:
a) $R^a$, —O—$R^a$, —S(O)$_m$—$R^a$, —N($R^a$)$_2$, ($R^a$)$_2$—(CH$_2$)$_{1-2}$—, —NH(CR⁷R⁸)$_n$—$R^a$, —(CR⁷R⁸)$_n$—$R^a$ or —O(CR⁷R⁸)$_n$—$R^a$;

or R⁵ is:
b) —C(O)—$R^a$, —C(O)—O(CR⁷R⁸)$_n$$R^a$, —C(O)(CR⁷R⁸)$_n$—$R^a$, —C(O)NH$R^a$, —C(O)NH(CR⁷R⁸)$_n$—, —C(O)C(O)$R^a$ or —C(O)C(O)O$R^a$;

each of the above R⁵ is optionally substituted by C1-3 alkyl, halogen or hydroxyl, and wherein n is 1-3.

In yet another embodiment, there are provided compounds of the formula (I) as described immediately above and wherein Ar¹ is:

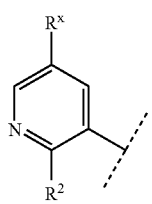

or Ar¹ is cyclopropyl, cyclobutyl, phenyl, naphthyl, tetrahydronaphthyl, indanyl and indenyl each independently substituted with one or more of R¹, $R^x$, and R²;

R¹ is nitrile, NO$_2$, NR$_2$, C1-3acylNH—,
J-S(O)$_m$—N($R^c$)— where J is C1-10 alkyl, or R¹ is

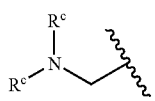

,

R² is independently chosen from C1-6 alkyl, C1-6 alkyl S(O)$_m$—, C1-3 alkoxy and C3-6 cycloalkyl optionally substituted by C1-3 alkyl, each may optionally be partially or fully halogenated;

R³ and R⁴ are each independently chosen from hydrogen, C1-3 alkyl, fluoro and chloro;

R⁶ is chosen from hydrogen and amino;

n is 1-2;

$R^a$ and $R^b$ are each independently chosen from hydrogen, C1-6 alkyl, C3-7 cycloalkylC0-2 alkyl, aryl, C1-5 alkoxy, amino, C1-5 alkylamino, C1-5 dialkylamino, arylamino, aryl C1-5alkylamino, C1-3 acyl, C1-5 alkoxycarbonyl, C1-5 acyloxy, C1-5 acylamino, C1-5 sulphonylamino, hydroxy, halogen, —CF$_3$, —CH$_2$—CF$_3$ nitro, nitrile;

or $R^a$ is chosen from pyrrolidinyl, pyrrolinyl, morpholinyl, thiomorpholinyl, thiomorpholinyl sulfoxide, thiomorpholinyl sulfone, piperidinyl, piperazinyl, homopiperazinyl, piperidinonyl, tetrahydropyrimidonyl, aziridinyl, isoxazolyl, oxazolyl, thiazolyl, thiadiazolyl, tetrazolyl, pyrazolyl, pyrrolyl, imidazolyl, pyridinyl, pyrimidinyl, pyrazinyl and pyridazinyl; wherein each aryl, heterocycle or heteroaryl for $R^a$ and $R^b$ is optionally substituted by amino, C1-3 alkyl, halogen or hydroxy.

In yet still another embodiment, there are provided compounds of the formula (I) as described immediately above and wherein Ar¹ is

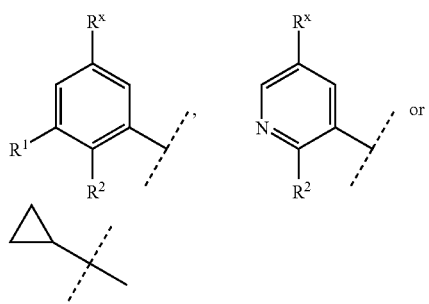

substituted by one or more of R¹, R² and $R^x$;

R¹ is:
J-S(O)$_2$—NH—, where J is C1-5 alkyl,
or R¹ is nitrile, NO$_2$, NH$_2$ or C1-3acylNH—;
wherein $R^x$=R² each are independently chosen from C1-5 alkyl, C1-5 alkylS(O)$_m$—, C1-4 alkoxy and and C3-5 cycloalkyl optionally substituted by C1-2 alkyl, each may optionally be partially or fully halogenated;
R⁸ is hydrogen, methyl, ethyl, CH$_2$OH and CH$_2$OCH$_3$.

In yet another embodiment, there are provided compounds of the formula (I) as described immediately above and wherein $R^a$ is chosen from hydrogen, C1-6 alkyl, C3-6 cycloalkylC0-2 alkyl, phenyl, C1-5 alkoxy, amino, C1-5 alkylamino, C1-5 dialkylamino, arylamino, aryl C1-5alkylamino, C1-3 acyl, C1-5 alkoxycarbonyl, C1-5 acyloxy, C1-5 acylamino, hydroxy, halogen, —CF$_3$, —CH$_2$—CF$_3$;

or $R^a$ is chosen from morpholinyl, thiomorpholinyl, thiomorpholinyl sulfoxide, thiomorpholinyl sulfone, piperazinyl, homopiperazinyl, pyrrolidinyl, piperidinyl, piperidinonyl, pyridinyl, pyrimidinyl, pyrazinyl and pyridazinyl wherein each phenyl, heterocycle or heteroaryl for $R^a$ is optionally substituted by amino, C1-3 alkyl, halogen or hydroxy.

In yet another embodiment, there are provided compounds of the formula (I) as described immediately above and wherein R$^a$ is chosen from hydrogen, C1-6 alkyl, C3-6 cycloalkyl, phenyl, C1-5 alkoxy, C1-5 alkoxycarbonyl, amino, C1-5 alkylamino, C1-5 dialkylamino, arylamino, aryl C1-5alkylamino, C1-5 acyloxy, C1-5 acylamino, hydroxy, halogen, —CF$_3$, —CH$_2$—CF$_3$;

or R$^a$ is chosen morpholinyl, piperidinyl piperazinyl, homopiperazinyl, pyrrolidinyl and pyridinyl wherein each phenyl, heterocycle or heteroaryl for R$^a$ is optionally substituted by amino, C1-3 alkyl, halogen or hydroxy.

In yet another embodiment, there are provided compounds of the formula (I) as described immediately above and wherein

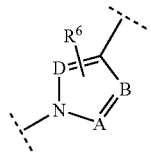

of the formula (I) is chosen from:

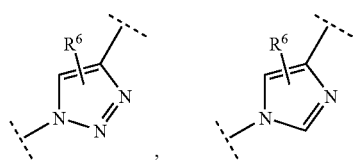

and

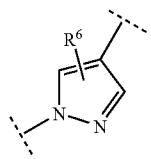

Ar$^1$ is

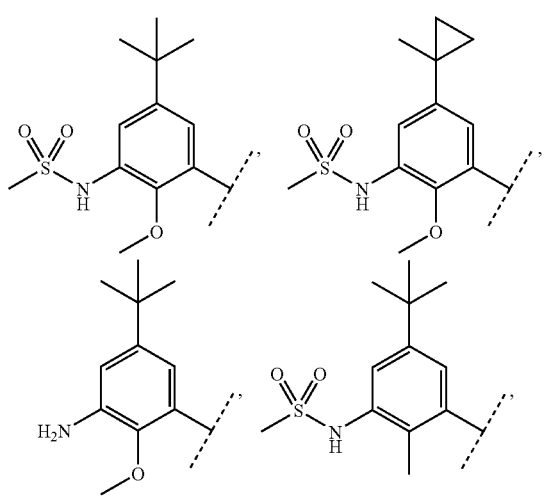

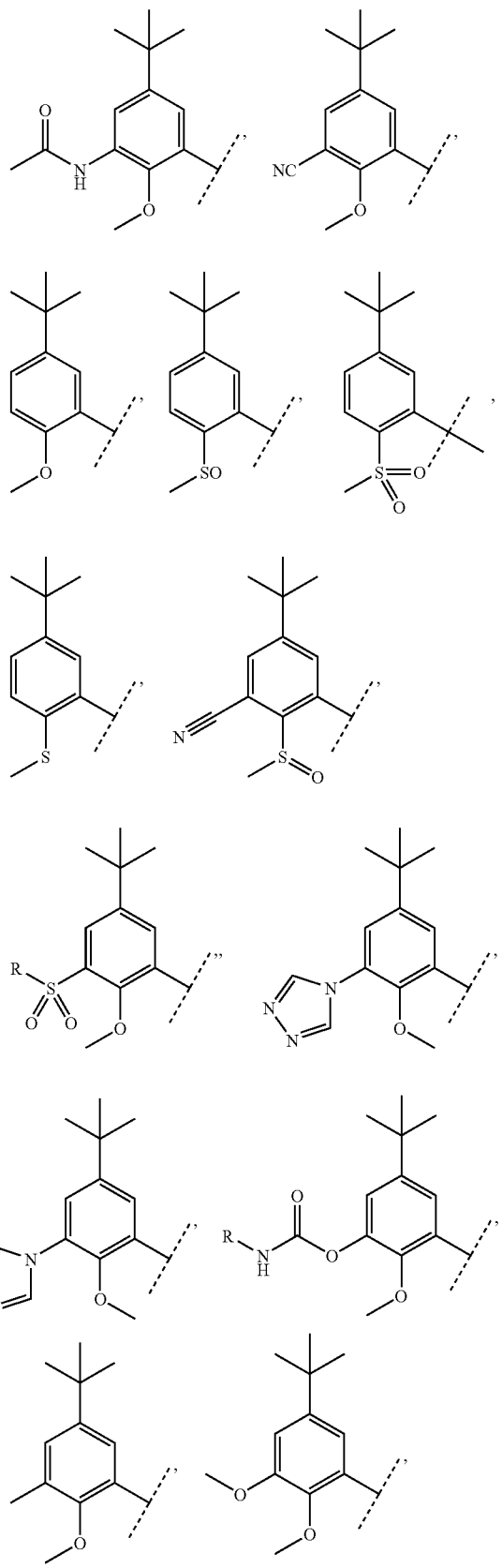

-continued

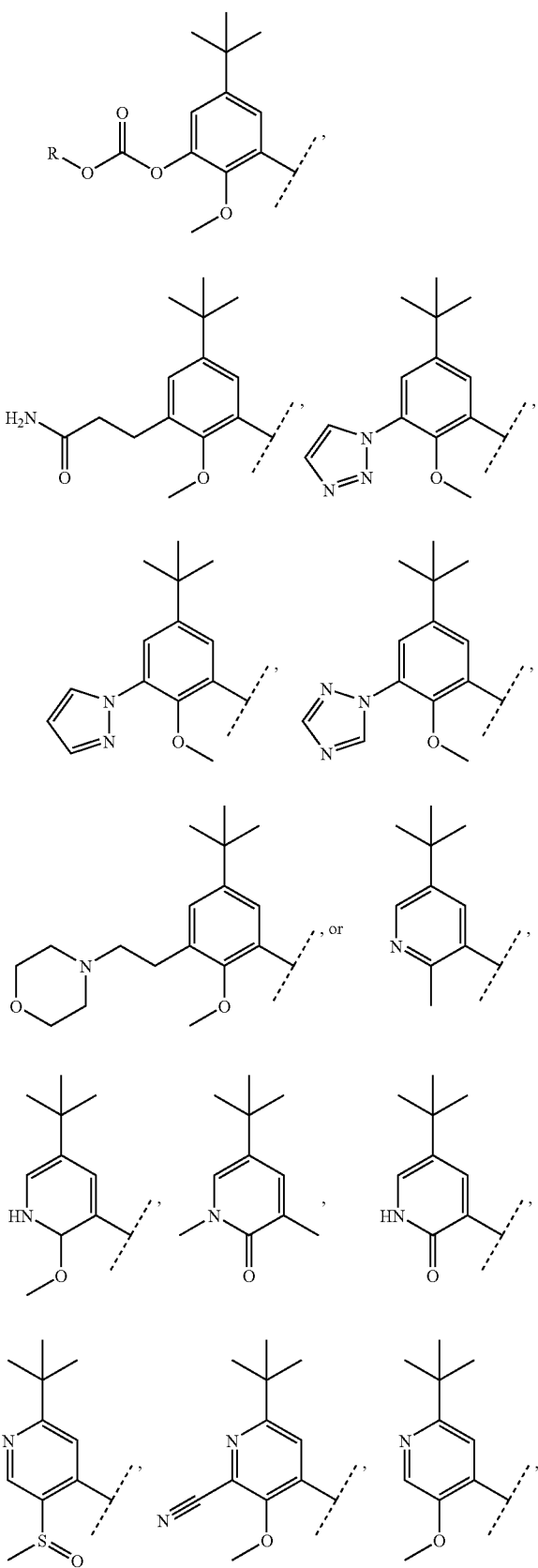

-continued

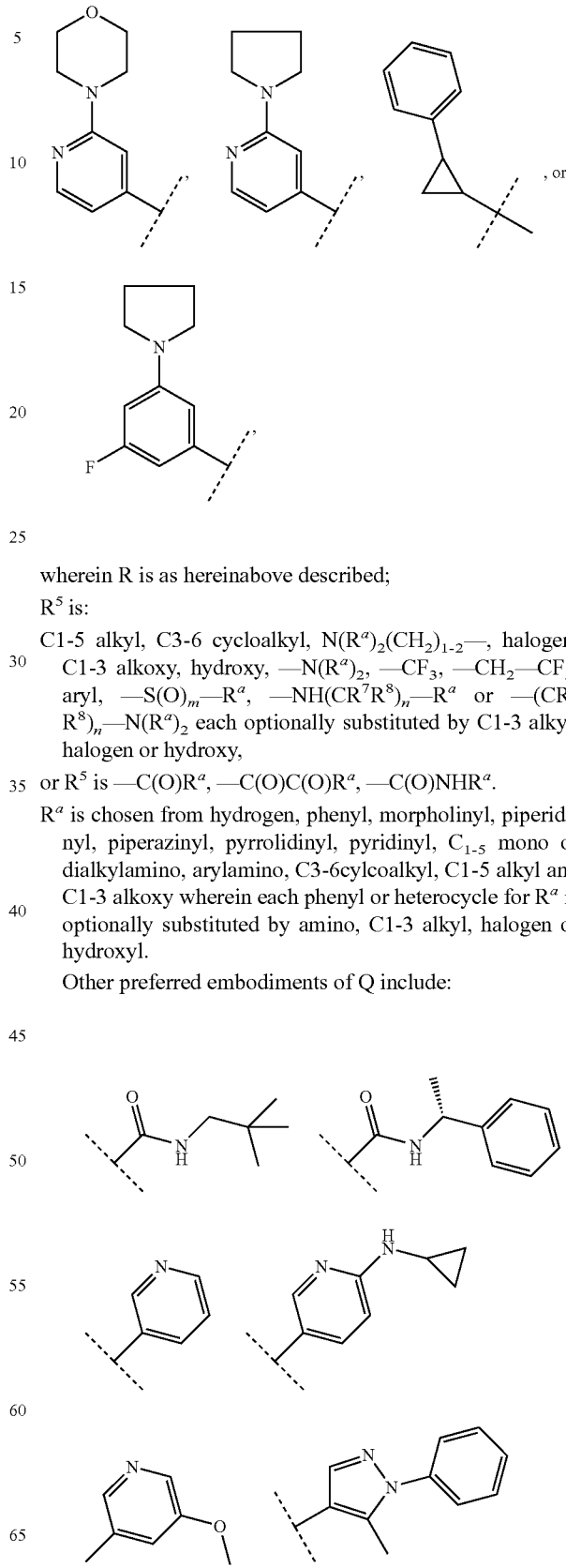

wherein R is as hereinabove described;

$R^5$ is:

C1-5 alkyl, C3-6 cycloalkyl, $N(R^a)_2(CH_2)_{1-2}$—, halogen, C1-3 alkoxy, hydroxy, —$N(R^a)_2$, —$CF_3$, —$CH_2$—$CF_3$, aryl, —$S(O)_m$—$R^a$, —$NH(CR^7R^8)_n$—$R^a$ or —$(CR^7R^8)_n$—$N(R^a)_2$ each optionally substituted by C1-3 alkyl, halogen or hydroxy, or $R^5$ is —$C(O)R^a$, —$C(O)C(O)R^a$, —$C(O)NHR^a$.

$R^a$ is chosen from hydrogen, phenyl, morpholinyl, piperidinyl, piperazinyl, pyrrolidinyl, pyridinyl, $C_{1-5}$ mono or dialkylamino, arylamino, C3-6cylcoalkyl, C1-5 alkyl and C1-3 alkoxy wherein each phenyl or heterocycle for $R^a$ is optionally substituted by amino, C1-3 alkyl, halogen or hydroxyl.

Other preferred embodiments of Q include:

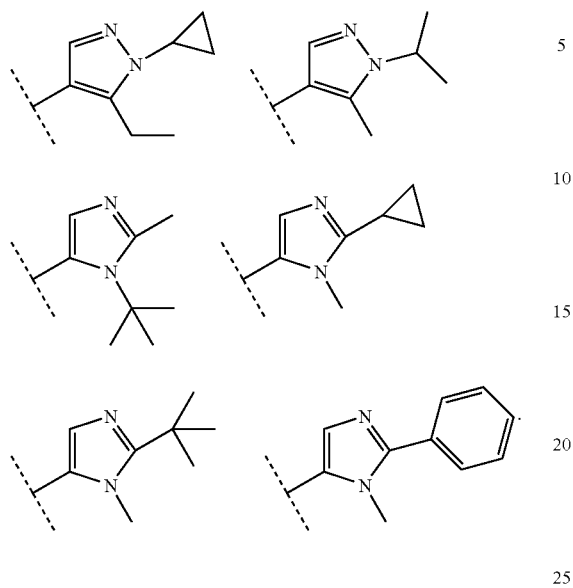

The following are representative compounds of the invention which can be made according to the general schemes and working examples below:

TABLE I

| Structure | Name |
|---|---|
| 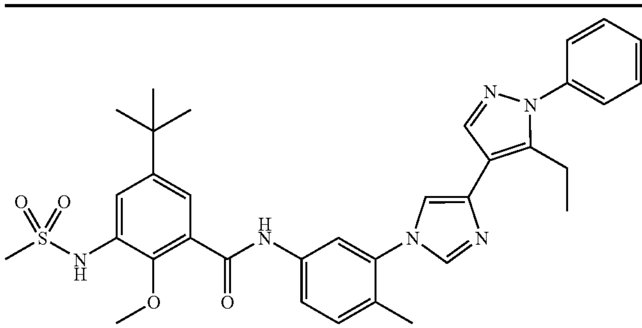 | 5-tert-Butyl-N-{3-[4-(5-ethyl-1-phenyl-1H-pyrazol-4-yl)-imidazol-1-yl]-4-methyl-phenyl}-3-methanesulfonylamino-2-methoxy-benzamide |
|  | 5-tert-Butyl-N-{3-[4-(5-ethyl-1-phenyl-1H-pyrazol-4-yl)-imidazol-1-yl]-4-methyl-phenyl}-2-methoxy-benzamide | or the pharmaceutically acceptable salts, acids, esters or isomers thereof.

In another embodiment, there is provided the following representative compounds of the invention which can be made according to the general schemes and working examples below:

| Structure | Name |
|---|---|
| 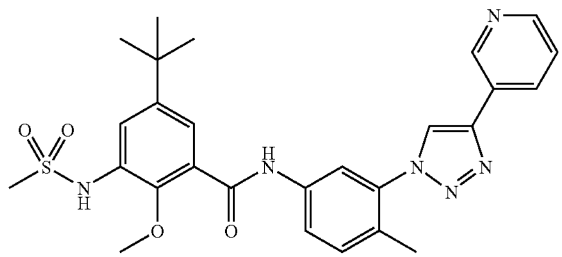 | 5-tert-Butyl-3-methanesulfonylamino-2-methoxy-N-[4-methyl-3-(4-pyridin-3-yl-1,2,3-triazol-1-yl)-phenyl]-benzamide |
| 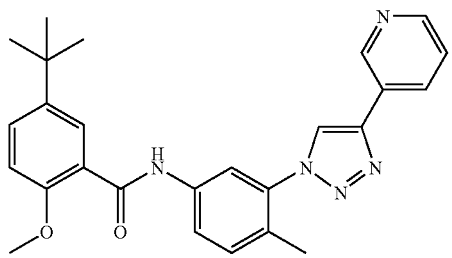 | 5-tert-Butyl-2-methoxy-N-[4-methyl-3-(4-pyridin-3-yl-1,2,3-triazol-1-yl)-phenyl]-benzamide |
| 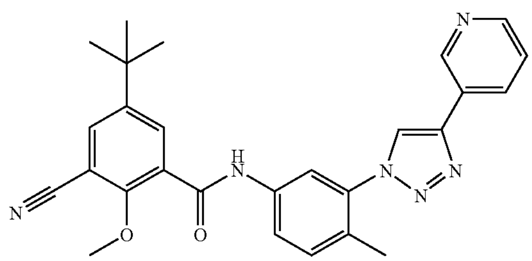 | 5-tert-Butyl-3-cyano-2-methoxy-N-[4-methyl-3-(4-pyridin-3-yl-1,2,3-triazol-1-yl)-phenyl]-benzamide |
| 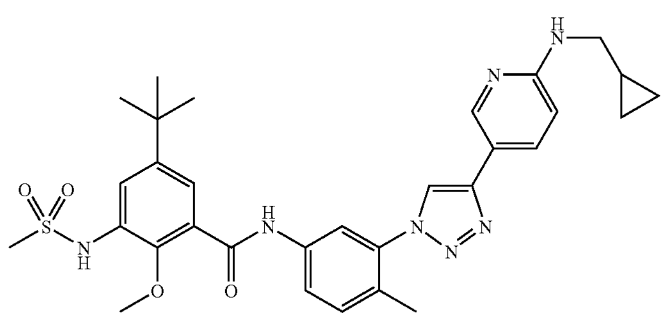 | 5-tert-Butyl-N-(3-{4-[6-(cyclopropylmethyl-amino)-pyridin-3-yl]-1,2,3-triazol-1-yl}-4-methyl-phenyl)-3-methanesulfonylamino-2-methoxy-benzamide |
| 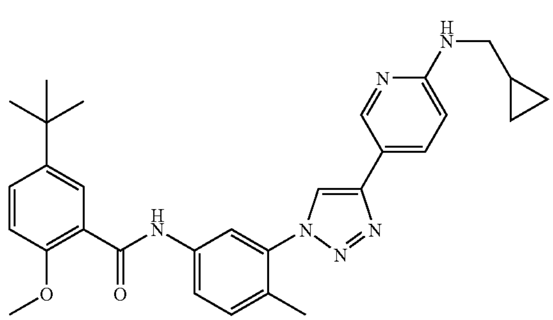 | 5-tert-Butyl-N-(3-{4-[6-(cyclopropylmethyl-amino)-pyridin-3-yl]-1,2,3-triazol-1-yl}-4-methyl-phenyl)-2-methoxy-benzamide |

-continued

| Structure | Name |
|---|---|
| 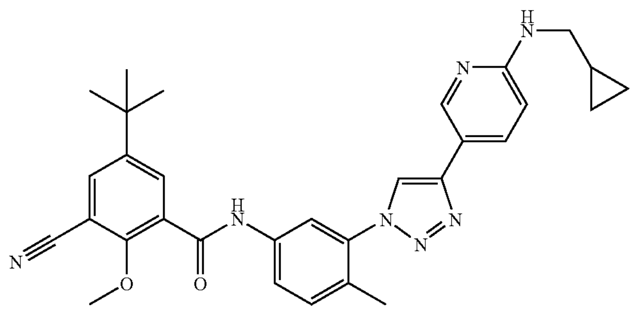 | 5-tert-Butyl-3-cyano-N-(3-{4-[6-(cyclopropylmethyl-amino)-pyridin-3-yl]-1,2,3-triazol-1-yl}-4-methyl-phenyl)-2-methoxy-benzamide |
| 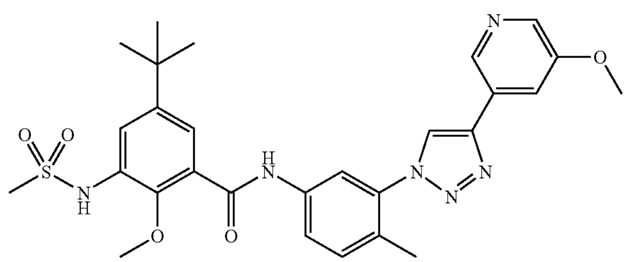 | 5-tert-Butyl-3-methanesulfonylamino-2-meethoxy-N-{3-[4-(5-methoxy-pyridin-3-yl)-1,2,3-triazol-1-yl]-4-methyl-phenyl}-benzamide |
| 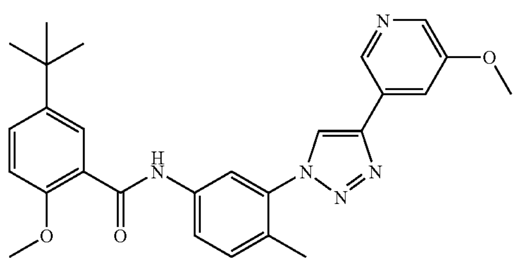 | 5-tert-Butyl-2-methoxy-N-{3-[4-(5-methoxy-pyridin-3-yl)-1,2,3-triazol-1-yl]-4-methyl-phenyl}-benzamide |
| 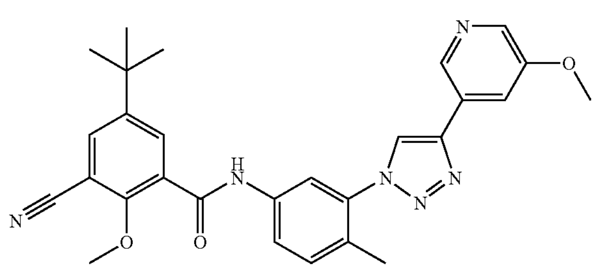 | 5-tert-Butyl-3-cyano-2-methoxy-N-{3-[4-(5-methoxy-pyridin-3-yl)-1,2,3-triazol-1-yl]-4-methyl-phenyl}-benzamide |
| 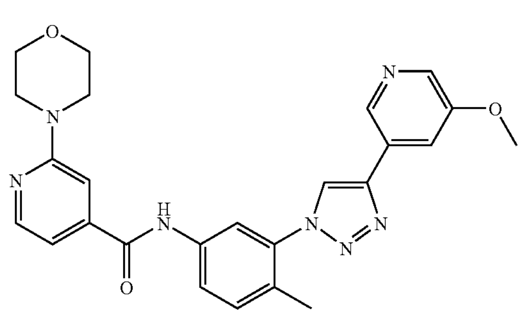 | N-{3-[4-(5-Methoxy-pyridin-3-yl)-1,2,3-triazol-1-yl]-4-methyl-phenyl}-2-morpholin-4-yl-isonicotinamide |

-continued

| Structure | Name |
|---|---|
| 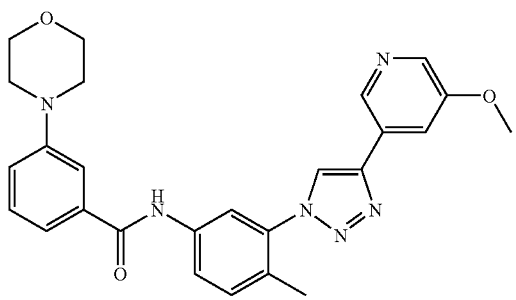 | N-{3-[4-(5-Methoxy-pyridin-3-yl)-1,2,3-triazol-1-yl]-4-methyl-phenyl}-3-morpholin-4-yl-benzamide |
| 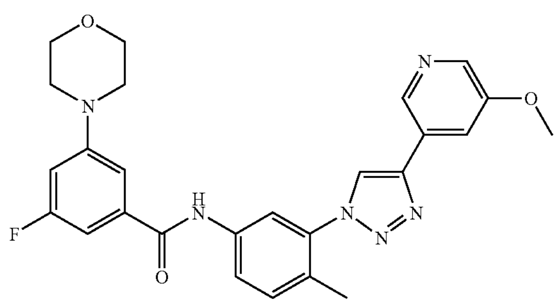 | 3-Fluoro-N-{3-[4-(5-methoxy-pyridin-3-yl)-1,2,3-triazol-1-yl]-4-methyl-phenyl}-5-morpholin-4-yl-benzamide |
| 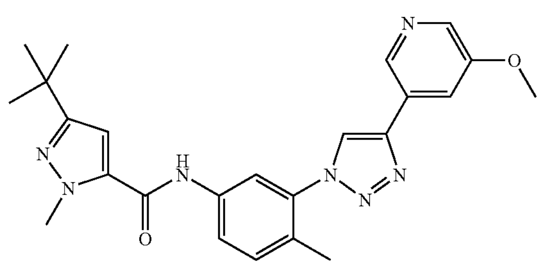 | 5-tert-Butyl-2-methyl-2H-pyrazole-3-carboxylic acid {3-[4-(5-methoxy-pyridin-3-yl)-1,2,3-triazol-1-yl]-4-methyl-phenyl}-amide |
| 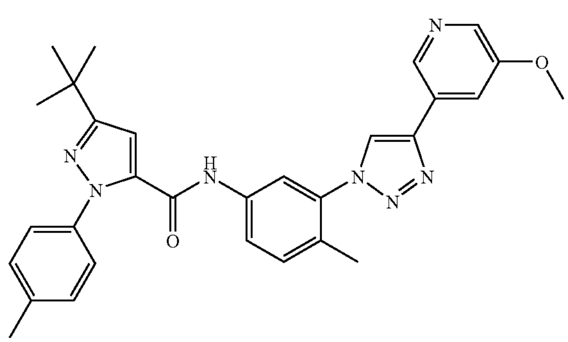 | 5-tert-Butyl-2-p-tolyl-2H-pyrazole-3-carboxylic acid {3-[4-(5-methoxy-pyridin-3-yl)-1,2,3-triazol-1-yl]-4-methyl-phenyl}-amide |
| 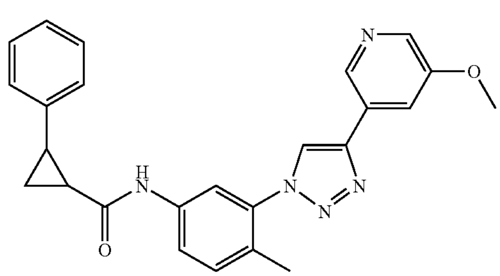 | 2-Phenyl-cyclopropanecarboxylic acid {3-[4-(5-methoxy-pyridin-3-yl)-1,2,3-triazol-1-yl]-4-methyl-phenyl}-amide |

-continued

| Structure | Name |
|---|---|
| 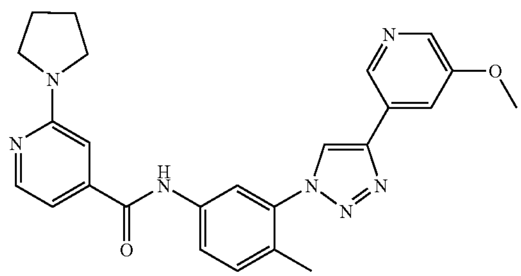 | N-{3-[4-(5-Methoxy-pyridin-3-yl)-1,2,3-triazol-1-yl]-4-methyl-phenyl}-2-pyrrolidin-1-yl-isonicotinamide |
| 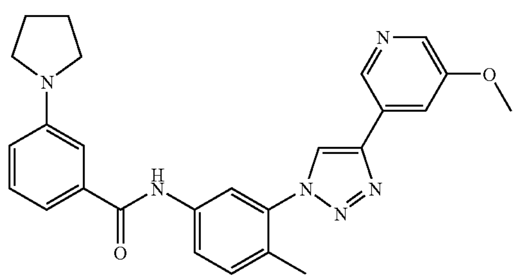 | N-{3-[4-(5-Methoxy-pyridin-3-yl)-1,2,3-triazol-1-yl]-4-methyl-phenyl}-3-pyrrolidin-1-yl-benzamide |
| 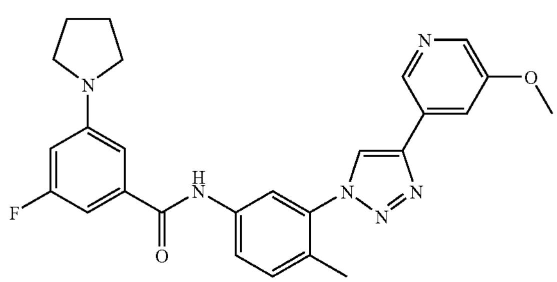 | 3-Fluoro-N-{3-[4-(5-methoxy-pyridin-3-yl)-1,2,3-triazol-1-yl]-4-methyl-phenyl}-5-pyrrolidin-1-yl-benzamide |
| 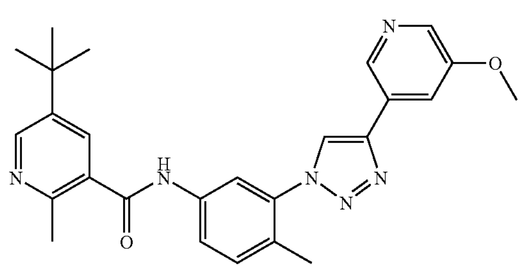 | 5-tert-Butyl-N-{3-[4-(5-methoxy-pyridin-3-yl)-1,2,3-triazol-1-yl]-4-methyl-phenyl}-2-methyl-nicotinamide |
| 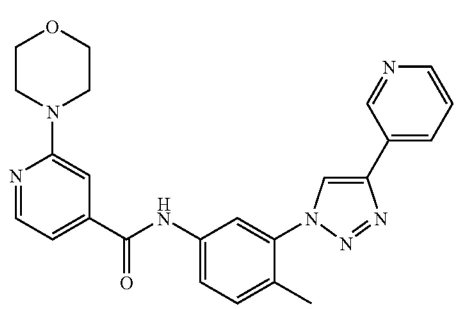 | N-[4-Methyl-3-(4-pyridin-3-yl-1,2,3-triazol-1-yl)-phenyl]-2-morpholin-4-yl-isonicotinamide |

-continued

| Structure | Name |
|---|---|
| 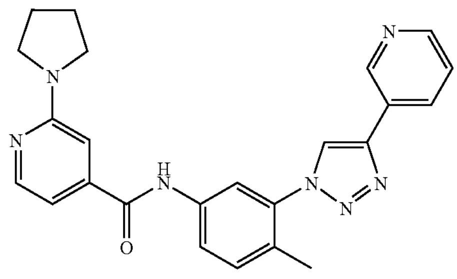 | N-[4-methyl-3-(4-pyridin-3-yl-1,2,3-triazol-1-yl)-phenyl]-2-pyrrolidin-1-yl-isonicotinamide |
| 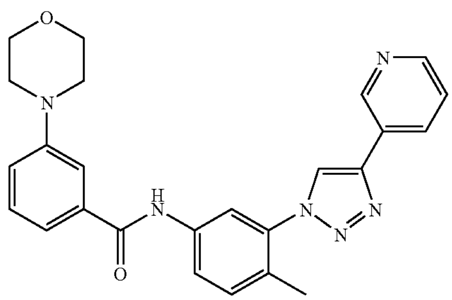 | N-[4-Methyl-3-(4-pyridin-3-yl-1,2,3-triazol-1-yl)-phenyl]-3-morpholin-4-yl-benzamide |
| 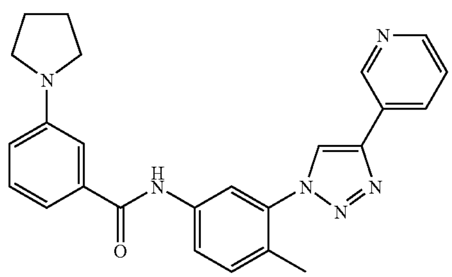 | N-[4-Methyl-3-(4-pyridin-3-yl-1,2,3-triazol-1-yl)-phenyl]-3-pyrrolidin-1-yl-benzamide |
| 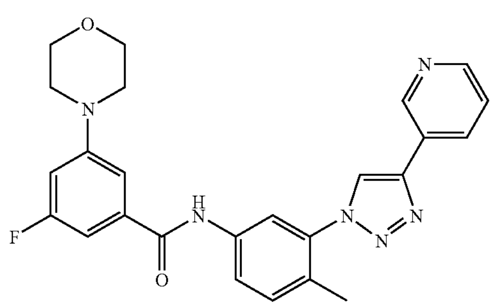 | 3-Fluoro-N-[4-methyl-3-(4-pyridin-3-yl-1,2,3-triazol-1-yl)-phenyl]-5-morpholin-4-yl-benzamide |
| 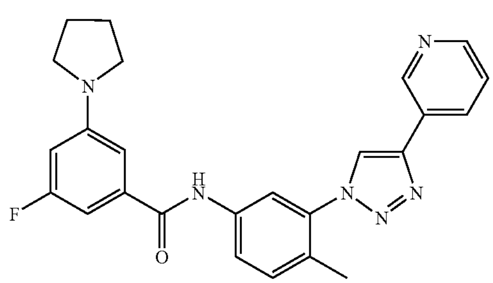 | 3-Fluoro-N-[4-methyl-3-(4-pyridin-3-yl-1,2,3-triazol-1-yl)-phenyl]-5-pyrrolidin-1-yl-benzamide |

-continued

| Structure | Name |
|---|---|
| 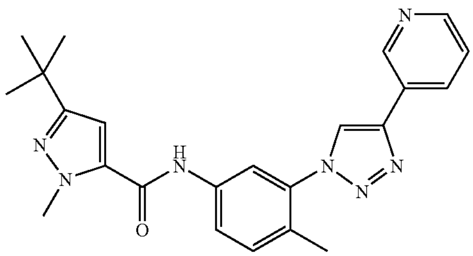 | 5-tert-Butyl-2-methyl-2H-pyrazole-3-carboxylic acid [4-methyl-3-(4-pyridin-3-yl-1,2,3-triazol-1-yl)-phenyl]-amide |
| 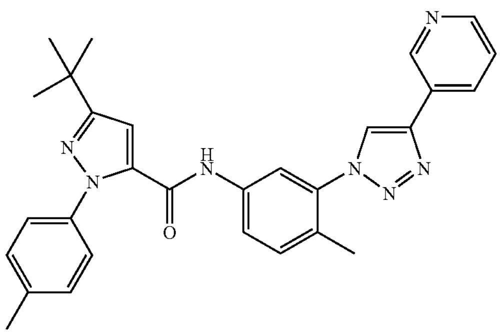 | 5-tert-Butyl-2-p-tolyl-2H-pyrazole-3-carboxylic acid [4-methyl-3-(4-pyridin-3-yl-1,2,3-triazol-1-yl)-phenyl]-amide |
| 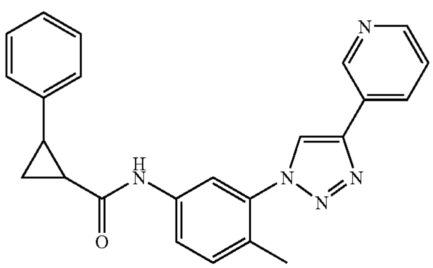 | 2-Phenyl-cyclopropanecarboxylic acid [4-methyl-3-(4-pyridin-3-yl-1,2,3-triazol-1-yl)-phenyl]-amide |
| 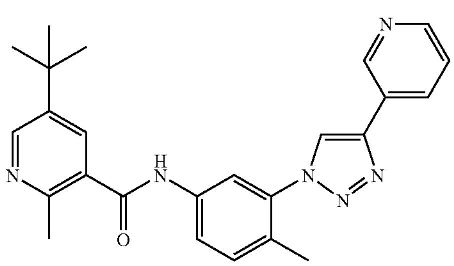 | 5-tert-Butyl-2-methyl-N-[4-methyl-3-(4-pyridin-3-yl-1,2,3-triazol-1-yl)-phenyl)-nicotinamide |
| 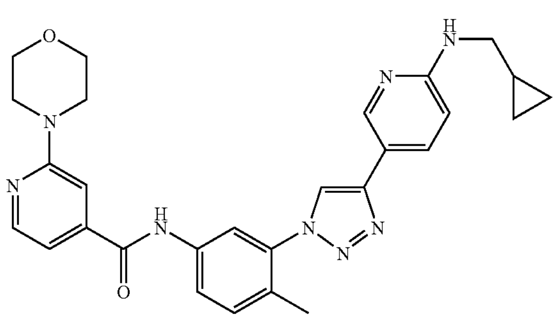 | N-(3-{4-[6-(Cyclopropylmethyl-amino)-pyridin-3-yl]-1,2,3-triazol-1-yl}-4-methyl-phenyl)-2-morpholin-4-yl-isonicotinamide |

-continued

| Structure | Name |
|---|---|
| 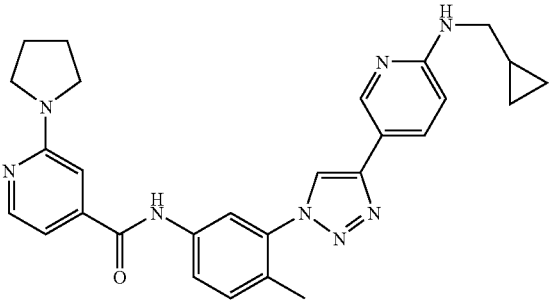 | N-(3-{4-[6-(Cyclopropylmethyl-amino)-pyridin-3-yl]-1,2,3-triazol-1-yl}-4-methyl-phenyl)-2-pyrrolidin-1-yl-isonicotinamide |
| 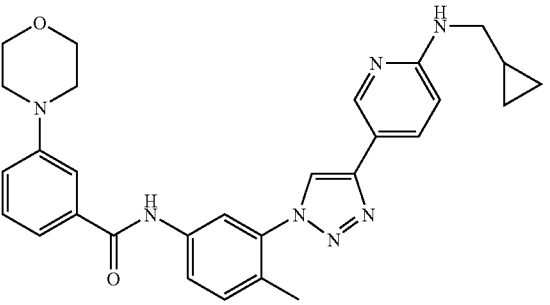 | N-(3-{4-[6-(Cyclopropylmethyl-amino)-pyridin-3-yl]-1,2,3-triazol-1-yl}-4-methyl-phenyl)-3-morpholin-4-yl-benzamide |
| 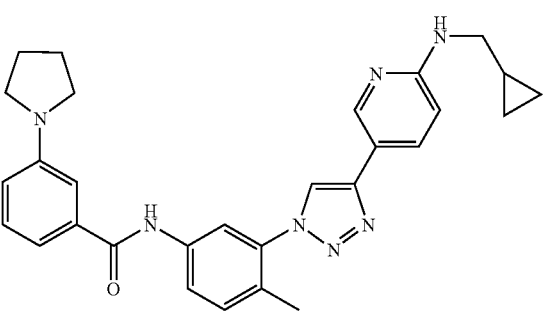 | N-(3-{4-[6-(Cyclopropylmethyl-amino)-pyridin-3-yl]-1,2,3-triazol-1-yl}-4-methyl-phenyl)-3-pyrrolidin-1-yl-benzamide |
| 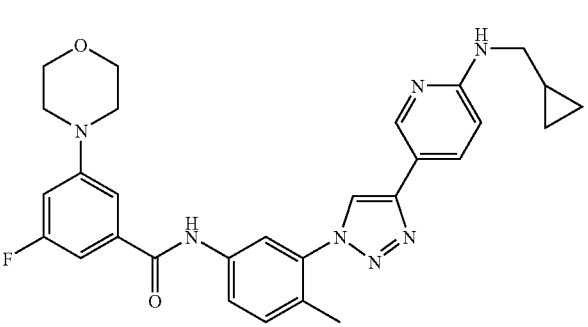 | N-(3-{4-[6-(Cyclopropylmethyl-amino)-pyridin-3-yl]-1,2,3-triazol-1-yl}-4-methyl-phhenyl)-3-fluoro-5-morpholin-4-yl-benzamide |
| 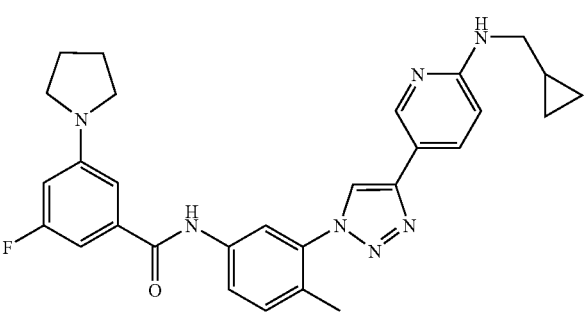 | N-(3-{4-[6-(cyclopropylmethyl-amino)-pyridin-3-yl]-1,2,3-triazol-1-yl}-4-methyl-phenyl)-3-fluoro-5-pyrrolidin-1-yl-benzamide |

| Structure | Name |
|---|---|
| 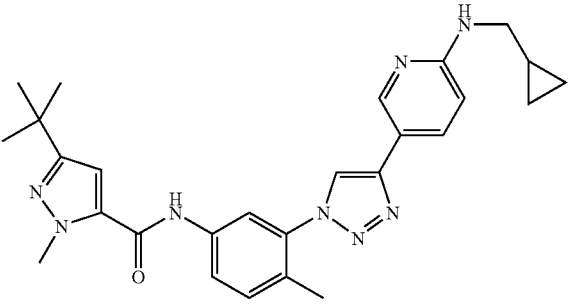 | 5-tert-Butyl-2-methyl-2H-pyrazole-3-carboxylic acid (3-{4-[6-(cyclopropylmethyl-amino)-pyridin-3-yl]-1,2,3-triazol-1-yl}-4-methyl-phenyl)-amide |
| 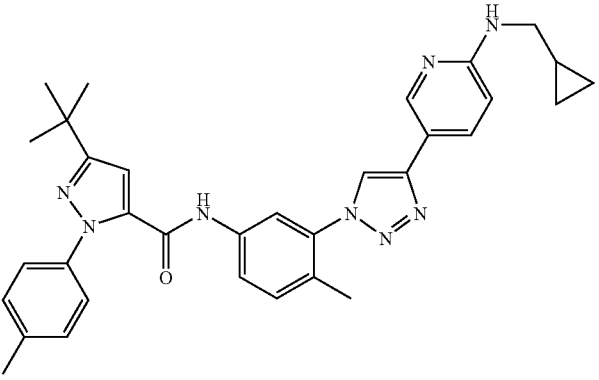 | 5-tert-Butyl-2-p-tolyl-2H-pyrazole-3-carboxylic acid (3-{4-[6-(cyclopropylmethyl-amino)-pyridin-3-yl]-1,2,3-triazol-1-yl}-4-methyl-phenyl)-amide |
| 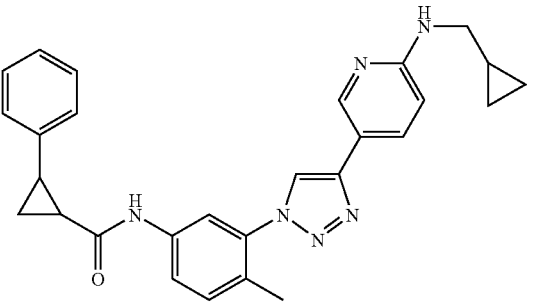 | 2-Phenyl-cyclopropanecarboxylic acid (3-{4-[6-(cyclopropylmethyl-amino)-pyridin-3-yl]-1,2,3-triazol-1-yl}-4-methyl-phenyl)-amide |
| 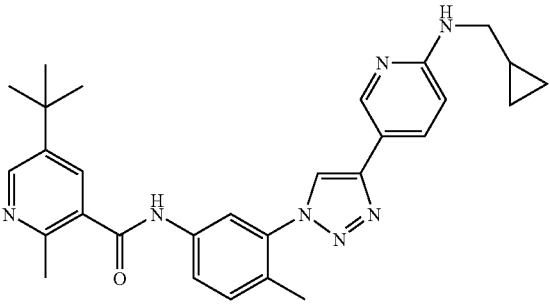 | 5-tert-Butyl-N-(3-{4-[6-(cyclopropylmethyl-amino)-pyridin-3-yl]-1,2,3-triazol-1-yl}-4-methyl-phenyl)-2-methyl-nicotinamide |
| 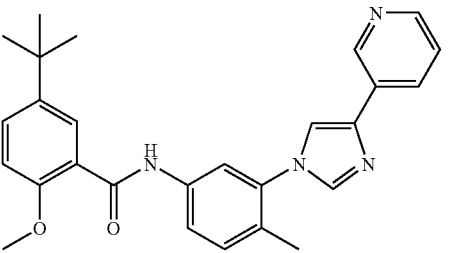 | 5-tert-Butyl-2-methoxy-N-[4-methyl-3-(4-pyridin-3-yl-imidazol-1-yl)-phenyl]-benzamide |

-continued

| Structure | Name |
|---|---|
| 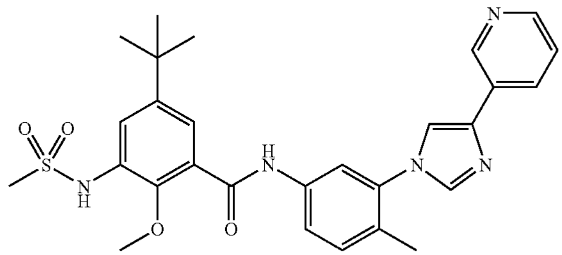 | 5-tert-Butyl-3-methanesulfonylamino-2-methoxy-N-[4-methyl-3-(4-pyridin-3-yl-imidazol-1-yl)-phenyl]-benzamide |
| 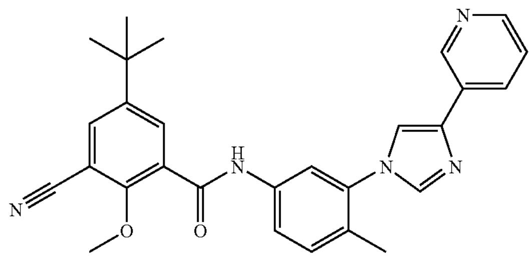 | 5-tert-Butyl-3-cyano-2-methoxy-N-[4-methyl-3-(4-pyridin-3-yl-imidazol-1-yl)-phenyl]-benzamide |
| 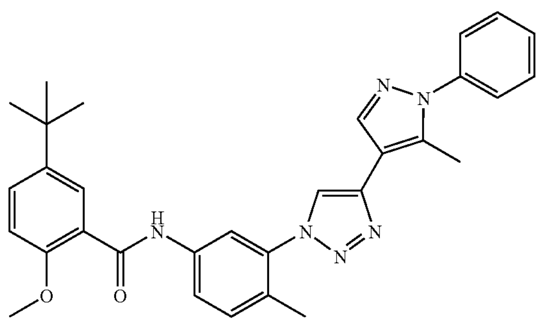 | 5-tert-Butyl-2-methoxy-N-{4-methyl-3-[4-(5-methyl-1-phenyl-1H-pyrazol-4-yl)-1,2,3-triazol-1-yl]-phenyl}-benzamide |
| 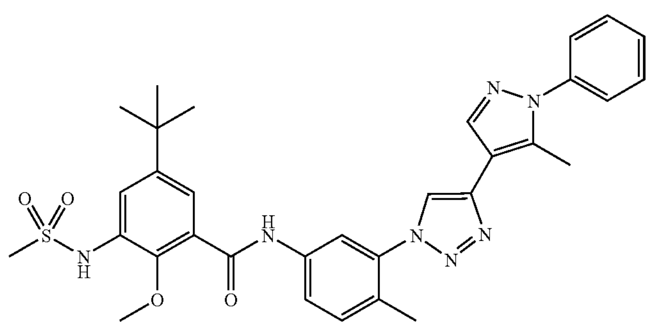 | 5-tert-Butyl-3-methanesulfonylamino-2-methoxy-N-{4-methyl-3-[4-(5-methyl-1-phenyl-1H-pyrazol-4-yl)-1,2,3-triazol-1-yl]-phenyl}-benzamide |
| 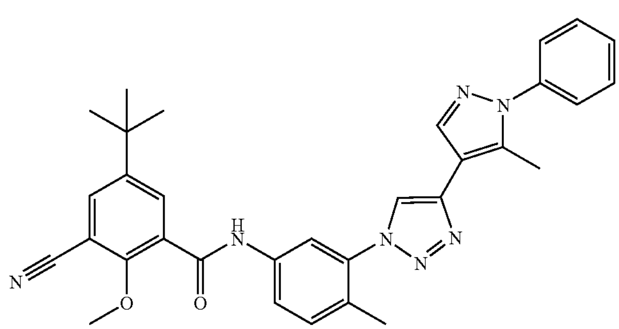 | 5-tert-Butyl-3-cyano-2-methoxy-N-{4-methyl-3-[4-(5-methyl-1-phenyl-1H-pyrazol-4-yl)-1,2,3-triazol-1-yl]-phenyl}-benzamide |

-continued

| Structure | Name |
|---|---|
| 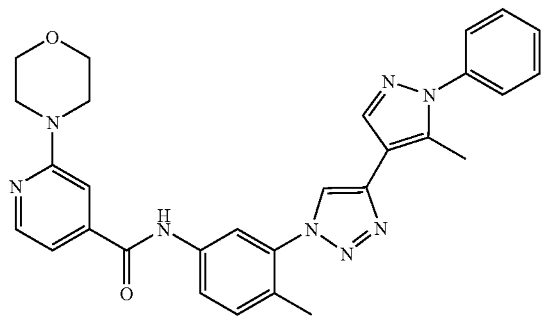 | N-{4-Methyl-3-[4-(5-methyl-1-phenyl-1H-pyrazol-4-yl)-1,2,3-triazol-1-yl]-phenyl}-2-morpholin-4-yl-isonicotinamide |
| 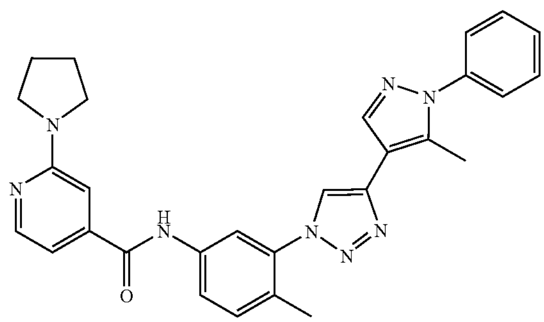 | N-{4-Methyl-3-[4-(5-methyl-1-phenyl-1H-pyrazol-4-yl)-1,2,3-triazol-1-yl]-phenyl}-2-pyrrolidin-1-yl-isonicotinamide |
| 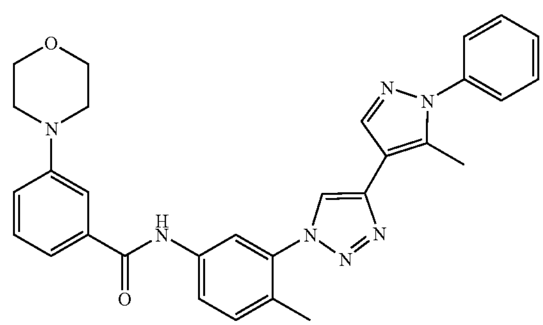 | N-{4-Methyl-3-[4-(5-methyl-1-phenyl-1H-pyrazol-4-yl)-1,2,3-triazol-1-yl]-phenyl}-3-morpholin-4-yl-benzamide |
| 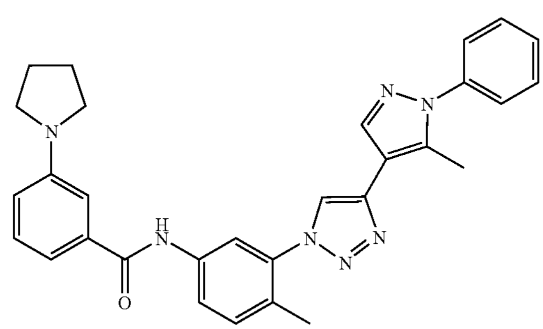 | N-{4-Methyl-3-[4-(5-methyl-1-phenyl-1H-pyrazol-4-yl)-1,2,3-triazol-1-yl]-phenyl}-3-pyrrolidin-1-yl-benzamide |

-continued

| Structure | Name |
|---|---|
| 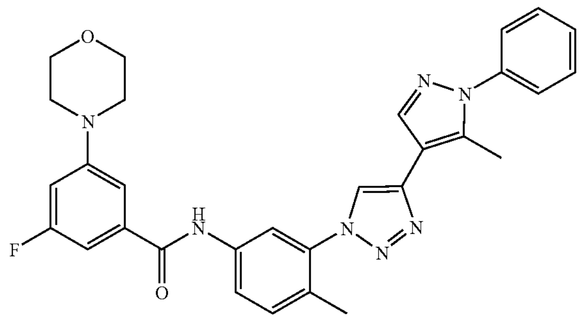 | 3-Fluoro-N-{4-methyl-3-[4-(5-methyl-1-phenyl-1H-pyrazol-4-yl)-1,2,3-triazol-1-yl]-phenyl}-5-morpholin-4-yl-benzamide |
| 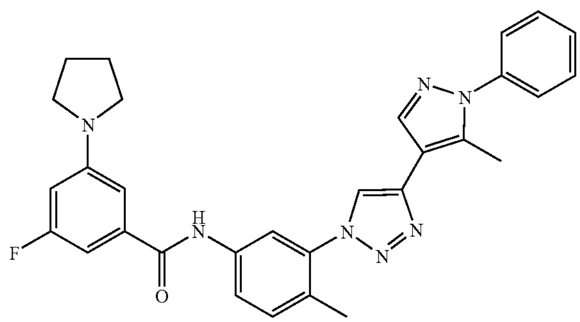 | 3-Fluoro-N-{4-methyl-3-[4-(5-methyl-1-phenyl-1H-pyrazol-4-yl)-1,2,3-triazol-1-yl]-phenyl}-5-pyrrolidin-1-yl-benzamide |
| 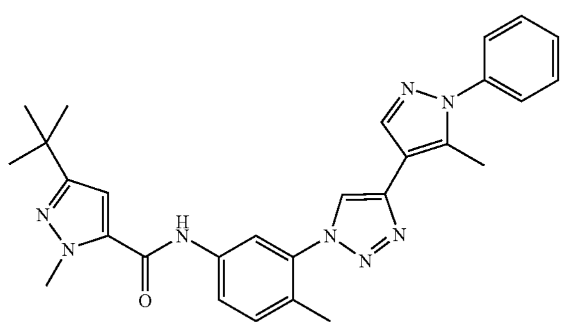 | 5-tert-Butyl-2-methyl-2H-pyrazole-3-carboxylic acid {4-methyl-3-[4-(5-methyl-1-phenyl-1H-pyrazol-4-yl)-1,2,3-triazol-1-yl]-phhenyl}-amide |
| 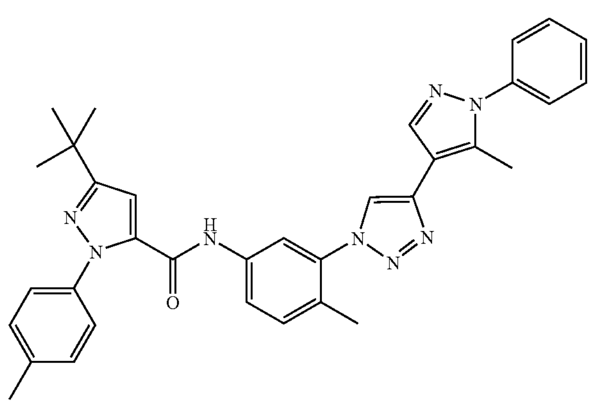 | 5-tert-Butyl-2-p-tolyl-2H-pyrazole-3-carboxylic acid {4-methyl-3-[4-(5-methyl-1-phenyl-1H-pyrazol-4-yl)-1,2,3-triazol-1-yl]-phenyl}-amide |

-continued

| Structure | Name |
|---|---|
| 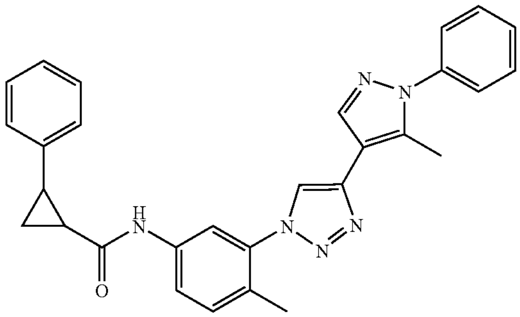 | 2-Phenyl-cyclopropanecarboxylic acid {4-methyl-3-[4-(5-methyl-1-phenyl-1H-pyrazol-4-yl)-1,2,3-triazol-1-yl]-phenyl}-amide |
| 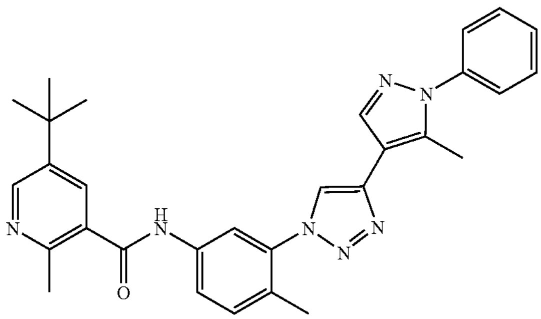 | 5-tert-Butyl-2-methyl-N-{4-methyl-3-[4-(5-methyl-1-phenyl-1H-pyrazol-4-yl)-1,2,3-triazol-1-yl]-phenyl}-nicotinamide |
| 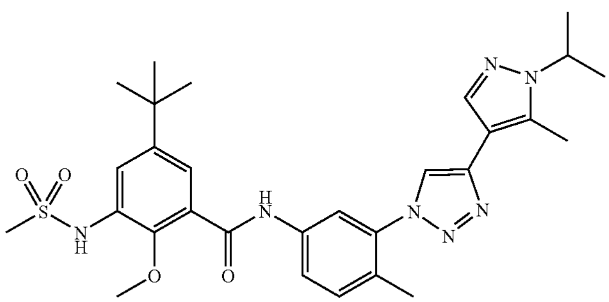 | 5-tert-Butyl-N-{3-[4-(1-isopropyl-5-methyl-1H-pyrazol-4-yl)-1,2,3-triazol-1-yl]-4-methyl-phenyl}-3-methanesulfonylamino-2-methoxy-benzamide |
| 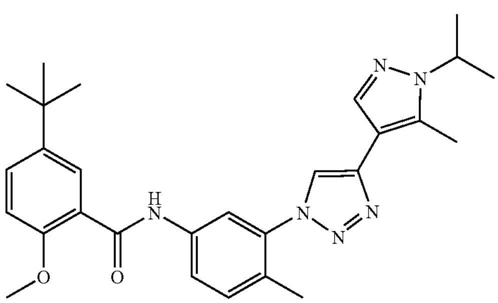 | 5-tert-Butyl-N-{3-[4-(1-isopropyl-5-methyl-1H-pyrazol-4-yl)-1,2,3-triazol-1-yl]-4-methyl-phenyl}-2-methoxy-benzamide |
| 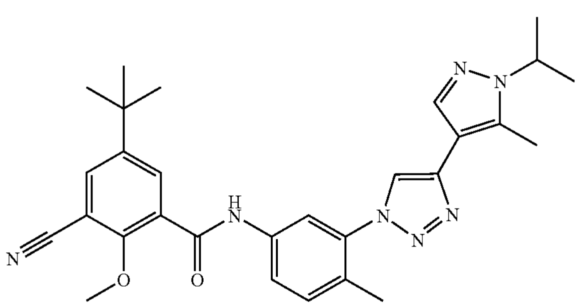 | 5-tert-Butyl-3-cyano-N-{3-[4-(1-isopropyl-5-methyl-1H-pyrazol-4-yl)-1,2,3-triazol-1-yl]-4-meethyl-phenyl}-2-methoxy-benzamide |

-continued

| Structure | Name |
|---|---|
| 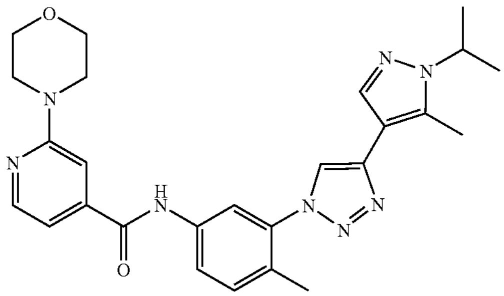 | N-{3-[4-(1-Isopropyl-5-methyl-1H-pyrazol-4-yl)-1,2,3-triazol-1-yl]-4-methyl-phenyl}-2-morpholin-4-yl-isonicotinamide |
| 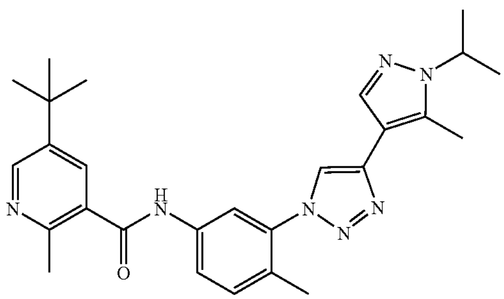 | 5-tert-Butyl-N-{3-[4-(1-isopropyl-5-methyl-1H-pyrazol-4-yl)-1,2,3-triazol-1-yl]-4-methyl-phenyl}-2-methyl-nicotinamide |
| 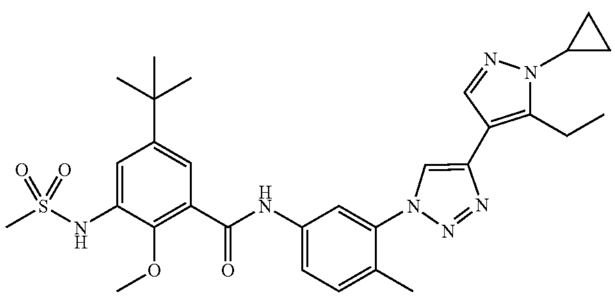 | 5-tert-Butyl-N-{3-[4-(1-cyclopropyl-5-ethyl-1H-pyrazol-4-yl)-1,2,3-triazol-1-yl]-4-methyl-phenyl}-3-methanesulfonylamino-2-methoxy-benzamide |
| 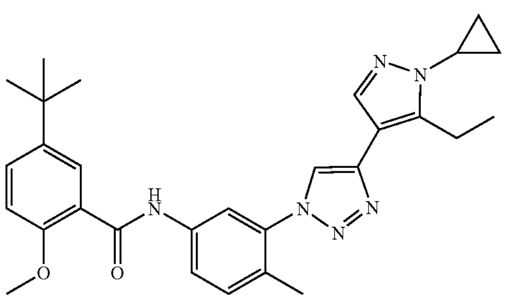 | 5-tert-Butyl-N-{3-[4-(1-cyclopropyl-5-ethyl-1H-pyrazol-4-yl)-1,2,3-triazol-1-yl]-4-methyl-phenyl}-2-methoxy-benzamide |
| 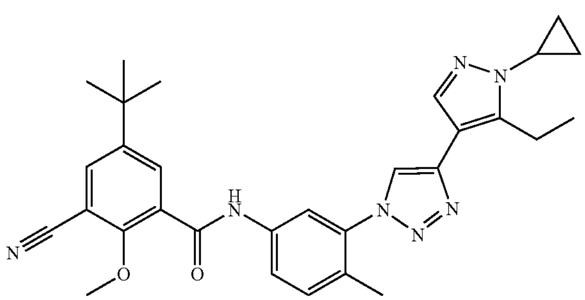 | 5-tert-Butyl-3-cyano-N-{3-[4-(1-cyclopropyl-5-ethyl-1H-pyrazol-4-yl)-1,2,3-triazol-1-yl]-4-methyl-phenyl}-2-methoxy-benzamide |

-continued

| Structure | Name |
|---|---|
| 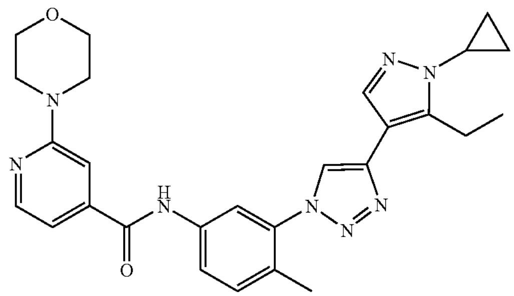 | N-{3-[4-(1-Cyclopropyl-5-ethyl-1H-pyrazol-4-yl)-1,2,3-triazol-1-yl]-4-methyl-phenyl}-2-morpholin-4-yl-isonicotinamide |
| 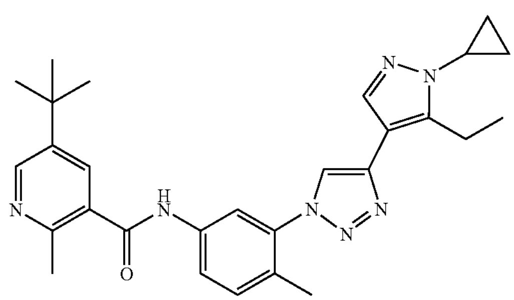 | 5-tert-Butyl-N-{3-[4-(1-cyclopropyl-5-ethyl-1H-pyrazol-4-yl)-1,2,3-triazaol-1-yl]-4-methyl-phenyl}-2-methyl-nicotinamide |
| 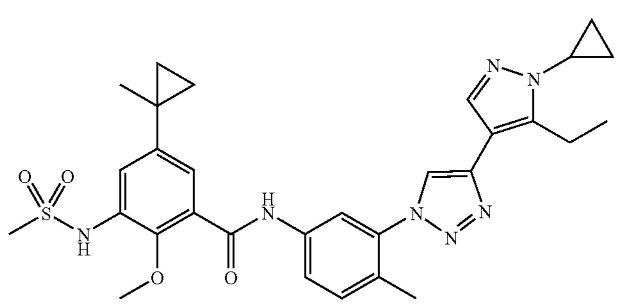 | N-{3-[4-(1-Cyclopropyl-5-ethyl-1H-pyrazol-4-yl)-1,2,3-triazol-1-yl]-4-methyl-phenyl}-3-methanesulfonylamino-2-methoxy-5-(1-methyl-cyclopropyl)-benzamide |
| 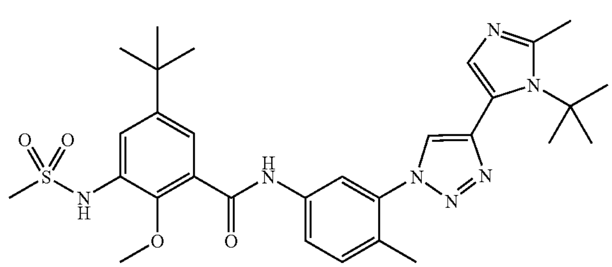 | 5-tert-Butyl-N-{3-[4-(3-tert-butyl-2-methyl-3H-imidazol-4-yl)-1,2,3-triazol-1-yl]-4-methyl-phenyl}-3-methanesulfonylamino-2-methoxy-benzamide |
| 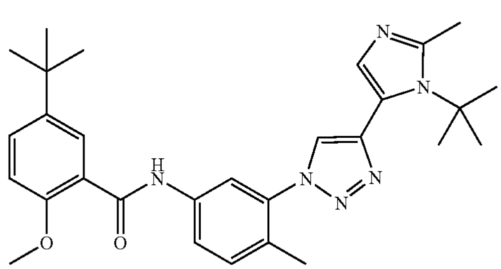 | 5-tert-Butyl-N-{3-[4-(4-tert-Butyl-2-methyl-3H-imidazol-4-yl)-1,2,3-triazol-1-yl]-4-methyl-phenyl}-2-methoxy-benzamide |

-continued

| Structure | Name |
|---|---|
| 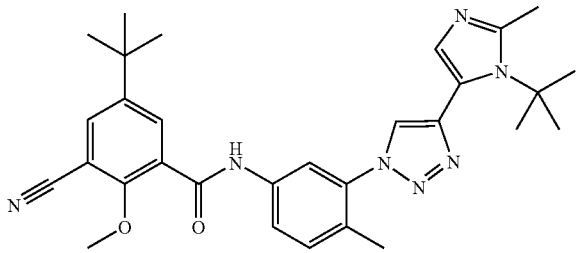 | 5-tert-Butyl-N-{3-[4-(3-tert-butyl-2-methyl-3H-imidazol-4-yl)-1,2,3-triazol-1-yl]-4-methyl-phenyl}-3-cyano-2-methoxy-benzamide |
| 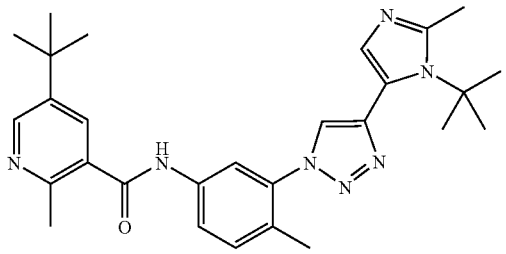 | 5-tert-Butyl-N-{3-[4-(3-tert-butyl-2-methyl-3H-imidazol-4-yl)-1,2,3-triazol-1-yl]-4-methyl-phenyl}-2-methyl-nicotinamide |
| 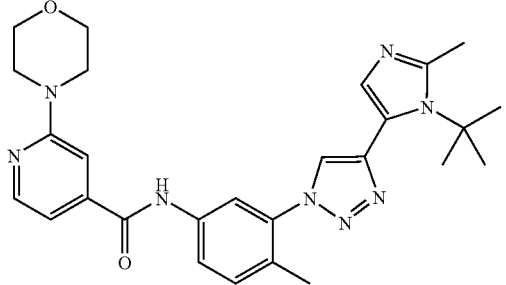 | N-{3-[4-(3-tert-Butyl-2-methyl-3H-imidazol-4-yl)-1,2,3-triazol-1-yl]-4-methyl-phenyl}-2-morpholin-4-yl-isonicotinamide |
| 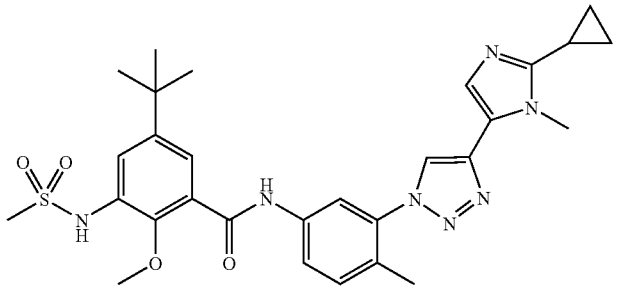 | 5-tert-Butyl-N-{3-[4-(2-cyclopropyl-3-methyl-3H-imidazol-4-yl)-1,2,3-triazol-1-yl]-4-methyl-phenyl}-3-methanesulfonylamino-2-methoxy-benzamide |
| 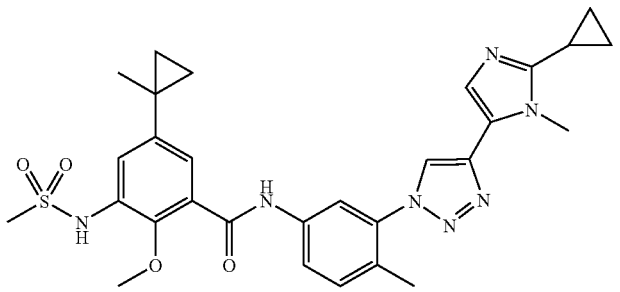 | N-{3-[4-(2-Cyclopropyl-3-methyl-3H-imidazol-4-yl)-1,2,3-triazol-1-yl]-4-methyl-phenyl}-3-methanesulfonylamino-2-methoxy-5-(1-methyl-cyclopropyl)-benzamide |

-continued

| Structure | Name |
|---|---|
| 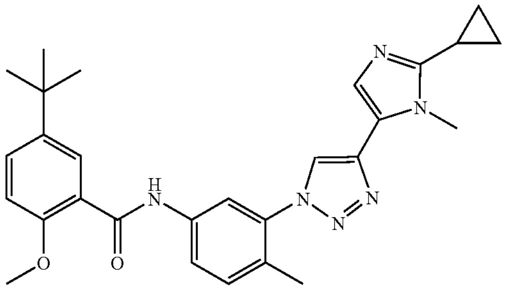 | 5-tert-Butyl-N-{3-[4-(2-cyclopropyl-3-methyl-3H-imidazol-4-yl)-1,2,3-triazol-1-yl]-4-methyl-phenyl}-2-methoxy-benzamide |
| 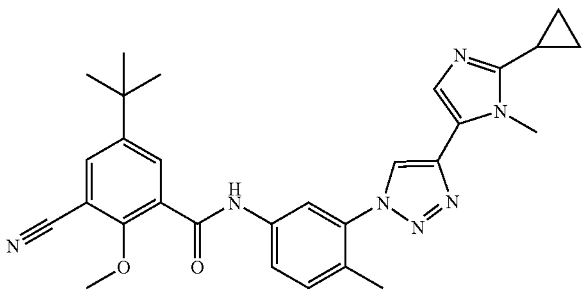 | 5-tert-Butyl-3-cyano-N-{3-[4-(2-cyclopropyl-3-methyl-3H-imidazol-4-yl)-1,2,3-triazol-1-yl]-4-methyl-phenyl}-2-methoxy-benzamide |
| 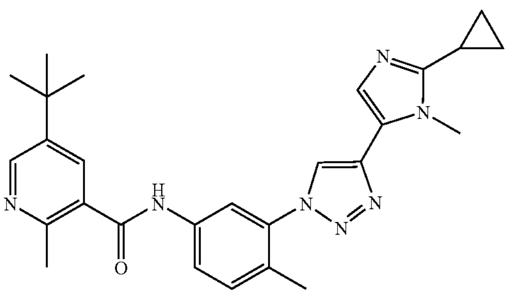 | 5-tert-Butyl-N-{3-[4-(2-cyclopropyl-3-methyl-3H-imidazol-4-yl)-1,2,3-triazol-1-yl]-4-methyl-phenyl}-2-methyl-nicotinamide |
| 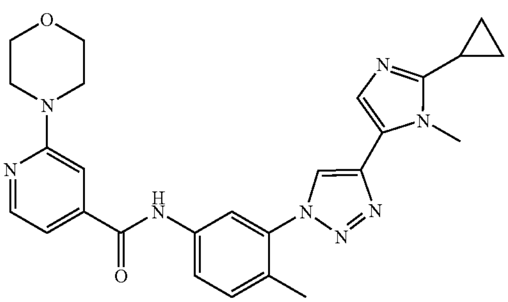 | N-{3-[4-(2-Cyclopropyl-3-methyl-3H-imidazol-4-yl)-1,2,3-triazol-1-yl]-4-methyl-phenyl}-2-morpholin-4-yl-isonicotinamide |
| 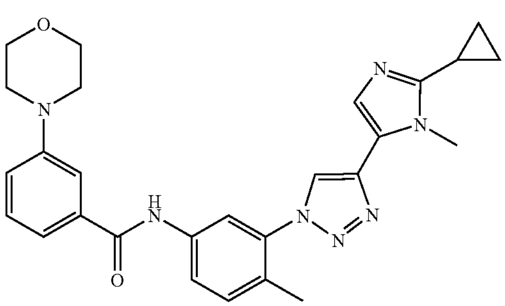 | N-{3-[4-(2-Cyclopropyl-3-methyl-3H-imidazol-4-yl)-1,2,3-triazol-1-yl]-4-methyl-phenyl}-3-morpholin-4-yl-benzamide |

-continued

| Structure | Name |
|---|---|
| 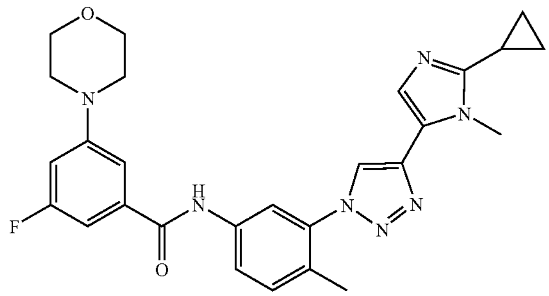 | N-{3-[4-(2-Cyclopropyl-3-methyl-3H-imidazol-4-yl)-1,2,3-triazol-1-yl]-4-methyl-phenyl}-3-fluoro-5-morpholin-4-yl-benzamide |
| 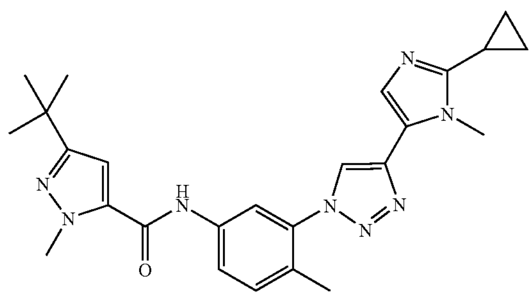 | 5-tert-Butyl-2-methyl-2H-pyrazole-3-carboxylic acid {3-[4-(2-cyclopropyl-3-methyl-3H-imidazol-4-yl)-1,2,3-triazol-1-yl]-4-methyl-phenyl}-amide |
| 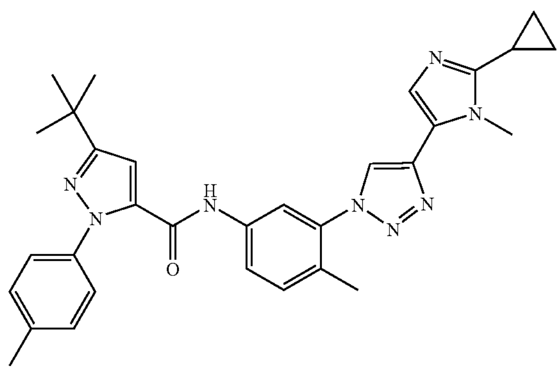 | 5-tert-Butyl-p-tolyl-2H-pyrazole-3-carboxylic acid {3-[4-(2-cyclopropyl-3-methyl-3H-imidazol-4-yl)-1,2,3-triazol-1-yl]-4-methyl-phenyl}-amide |
| 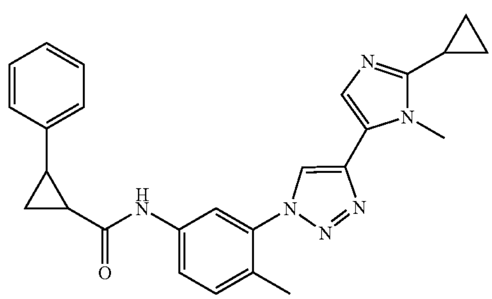 | 2-Phenyl-cyclopropanecarboxylic acid {3-[4-(2-cyclopropyl-3-methyl-3H-imidazol-4-yl)-1,2,3-triazol-1-yl]-4-methyl-phenyl}-amide |
| 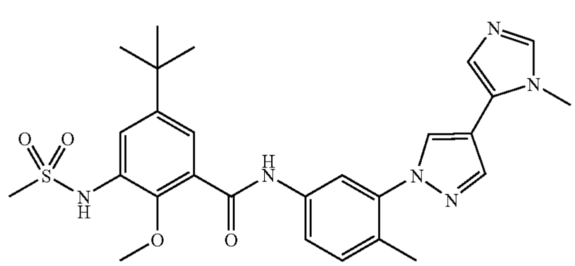 | 5-tert-Butyl-3-methanesulfonylamino-2-methoxy-N-{4-methyl-3-[4-(3-methyl-3H-imidazol-4-yl)-pyrazol-1-yl]-phenyl}-benzamide |

| Structure | Name |
|---|---|
| 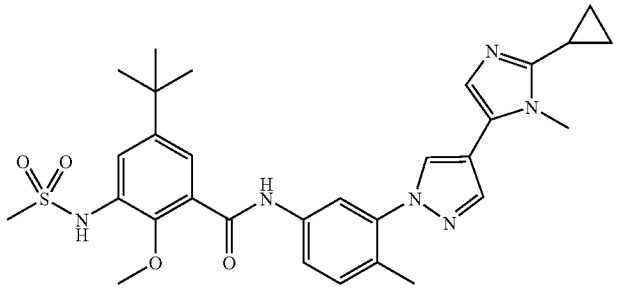 | 5-tert-Butyl-N-{3-[4-(2-cyclopropyl-3-methyl-3H-imidazol-4-yl)-pyrazol-1-yl]-4-methyl-phenyl}-3-methanesulfonylamino-2-methoxy-benzamide |
| 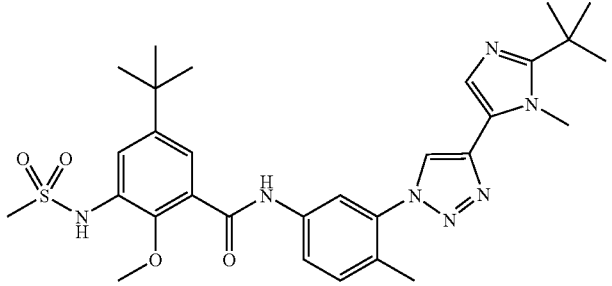 | 5-tert-Butyl-N-{3-[4-(2-tert-butyl-3-methyl-3H-imidazol-4-yl)-1,2,3-triazol-1-yl]-4-methyl-phenyl}-3-methanesulfonylmaino-2-methoxy-benzamide |
| 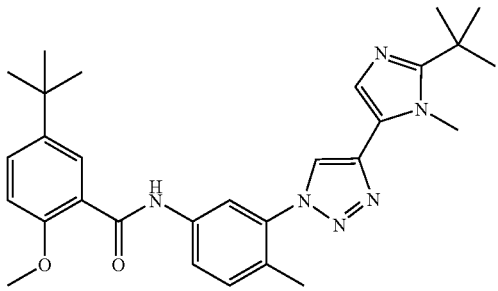 | 5-tert-Butyl-N-{3-[4-(2-tert-butyl-3-methyl-3H-imidazol-4-yl)-1,2,3-triazol-1-yl]-4-methyl-phenyl}-2-methoxy-benzamide |
| 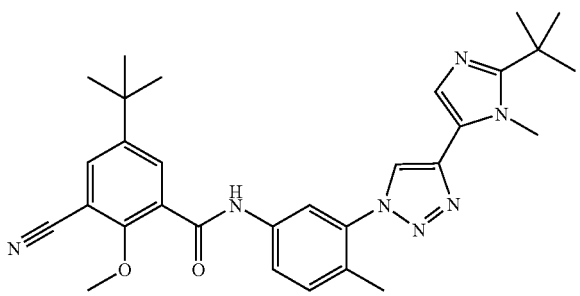 | 5-tert-Butyl-N-{3-[4-(2-tert-butyl-3-methyl-3H-imidazol-4-yl)-1,2,3-triazol-1-yl]-4-methyl-phenyl}-3-cyano-2-methoxy-benzamide |
| 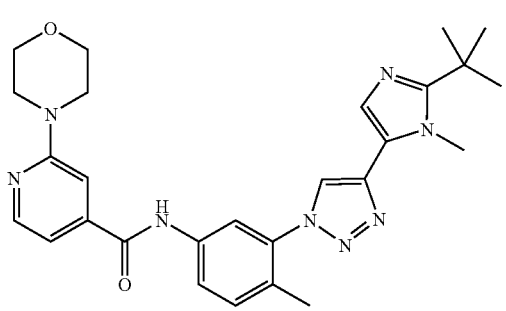 | N-{3-[4-(2-tert-Butyl-3-methyl-3H-imidazol-4-yl)-1,2,3-triazol-1-yl]-4-methyl-phenyl}-2-morpholin-4-yl-isonicotinamide |

| Structure | Name |
|---|---|
| 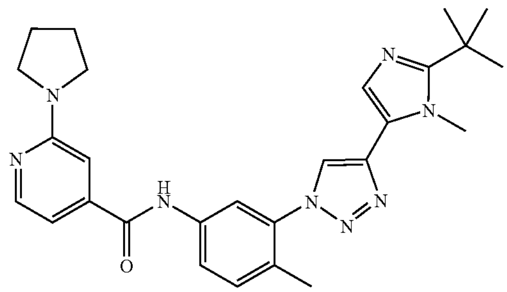 | N-{3-[4-(2-tert-Butyl-3-methyl-3H-imidazol-4-yl)-1,2,3-triazol-1-yl]-4-methyl-phenyl}-2-pyrrolidin-1-yl-isonicotinamide |
| 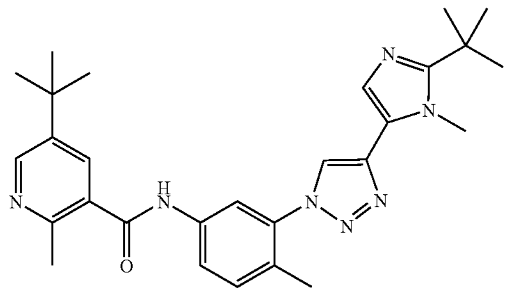 | 5-tert-Butyl-N-{3-[4-(2-tert-butyl-3-meethyl-3H-imidazol-4-yl)-1,2,3-triazol-1-yl]-4-methyl-phenyl}-2-methyl-nicotinamide |
| 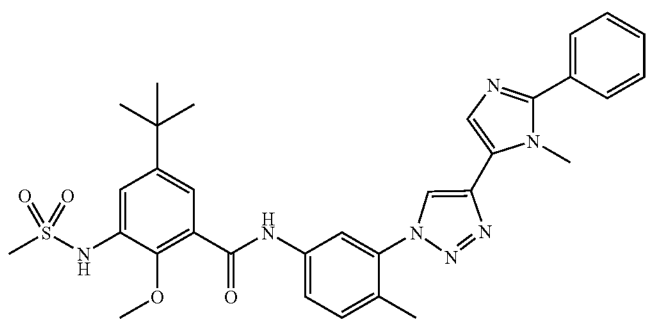 | 5-tert-Butyl-3-methanesulfonylamino-2-methoxy-N-{4-methyl-3-[4-(3-methyl-2-phenyl-3H-imidazol-4-yl)-1,2,3-triazol-1-yl]-phenyl}-benzamide |
| 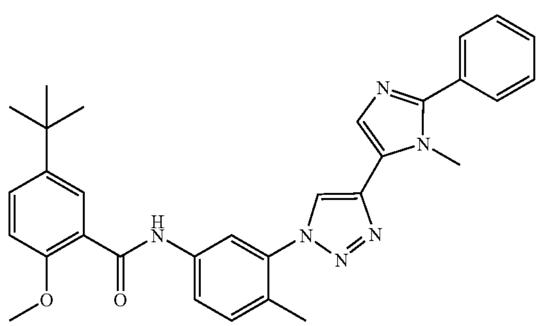 | 5-tert-Butyl-2-methoxy-N-{4-methyl-3-[4-(3-methyl-2-phenyl-3H-imidazol-4-yl)-1,2,3-triazol-1-yl]-phenyl}-benzamide |
| 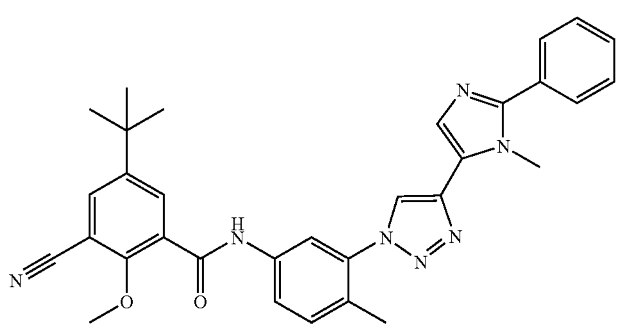 | 5-tert-Butyl-3-cyano-2-methoxy-N-{4-methyl-3-[4-(3-methyl-2-phenyl-3H-imidazol-4-yl)-1,2,3-triazol-1-yl]-phenyl}-benzamide |

-continued

| Structure | Name |
|---|---|
| 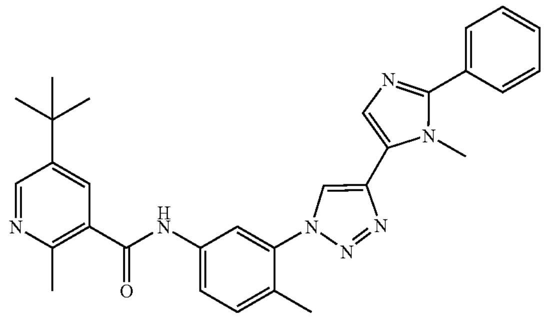 | 5-tert-Butyl-2-methyl-N-{4-methyl-3-[4-(3-methyl-2-phenyl-3H-imidazol-4-yl)-1,2,3-triazol-1-yl]-phenyl}-nicotinamide |
| 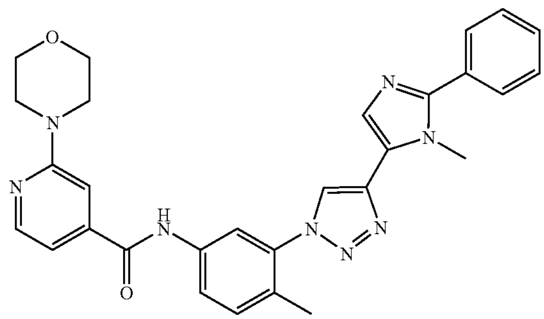 | N-{4-Methyl-3-[4-(4-methyl-2-phenyl-3H-imidazol-4-yl)-1,2,3-triazol-1-yl]-phenyl}-2-morpholin-4-yl-isonicotinamide |
| 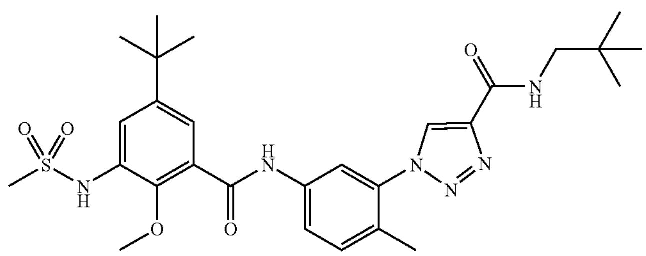 | 1-[5-(5-tert-Butyl-3-methanesulfonylamino-2-methoxy-benzoylamino)-2-methyl-phenyl]-1H-1,2,3-triazole-4-carboxylic acid (2,2-dimethyl-propyl)-amide |
| 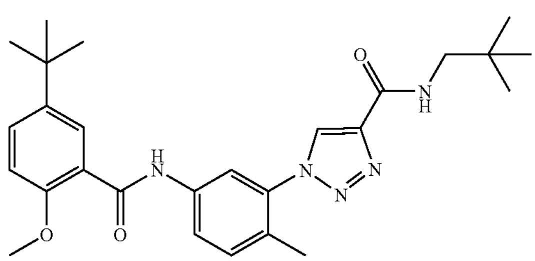 | 1-[5-(5-tert-Butyl-2-methoxy-benzoylamino)-2-methyl-phhenyl]-1H-1,2,3-triazole-3-carboxylic acid (2,2-dimethyl-propyl)-amide |
| 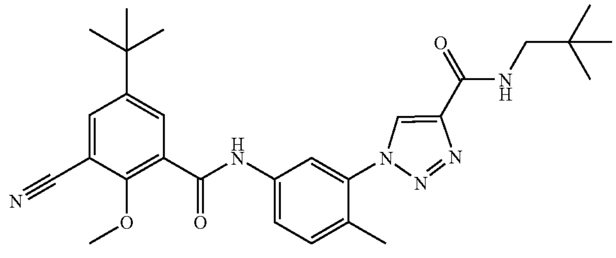 | 1-[5-(5-tert-Butyl-3-cyano-2-methoxy-benzoylamino)-2-methyl-phenyl]-1H-1,2,3-triazole-4-carboxylic acid (2,2-dimethyl-propyl)-amide |

-continued

| Structure | Name |
|---|---|
| 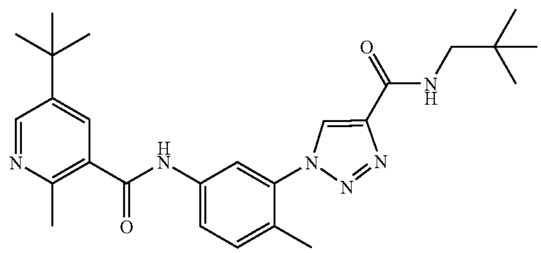 | 5-tert-Butyl-N-{3-[4-(2,2-dimethyl-propylcarbamoyl)-1,2,3-triazol-1-yl]-4-methyl-phhenyl}-2-methyl-nicotinamide |
| 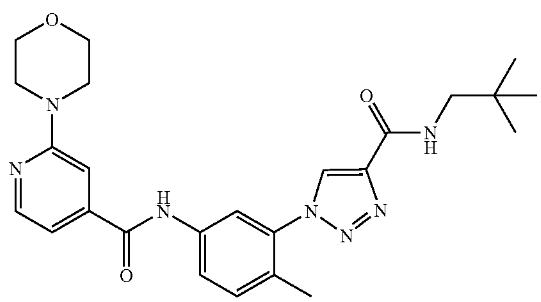 | N-{3-[4-(2,2-Dimethyl-propylcarbamoyl)-1,2,3-triazol-1-yl]-4-methyl-phenyl}-2-morpholin-4-yl-isonicotinamide |
| 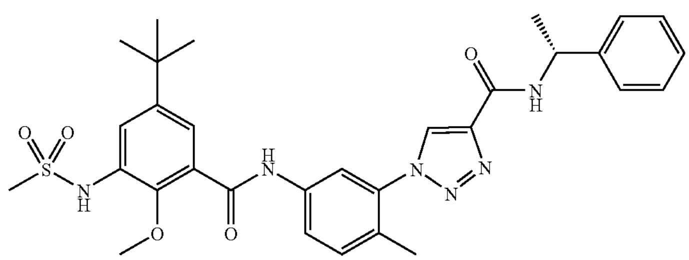 | 1-[5-(5-tert-Butyl-3-methanesulfonylamino-2-methoxy-benzoylamino)-2-methyl-phenyl]-1H-1,2,3-triazole-4-carboxylic acid ((R)-1-phenyl-ethyl)-amide |
| 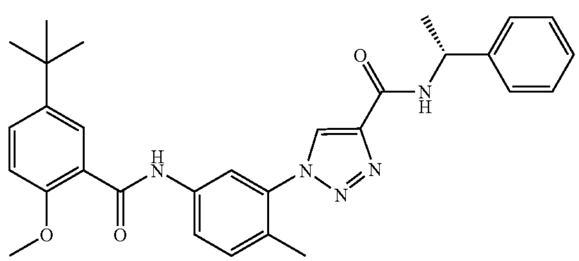 | 1-[5-(5-tert-Butyl-2-methoxy-benzoylamino)-2-methyl-phenyl]-1H-1,2,3-triazole-4-carboxylic acid ((R)-1-phenyl-ethyl)-amide |
| 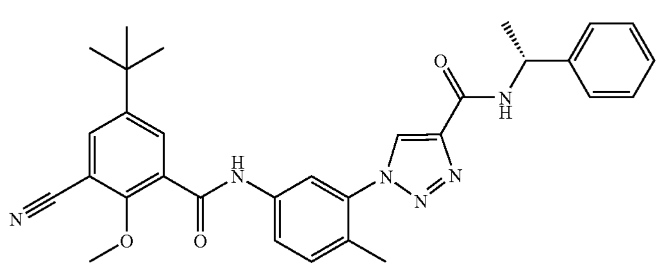 | 1-[5-(5-tert-Butyl-3-cyano-2-methoxy-benzoylamino)-2-methyl-phenyl]-1H-1,2,3-triazole-4-carboxylic acid ((R)-1-phenyl-ethyl)-amide |

-continued

| Structure | Name |
|---|---|
| 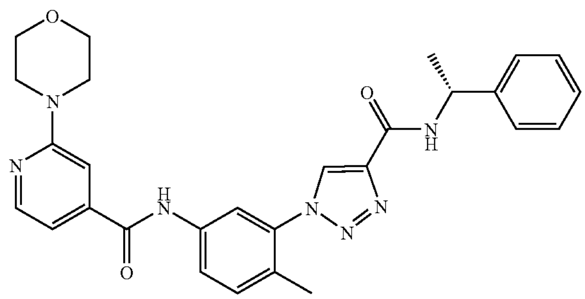 | N-{4-Methyl-3-[4-((R)-1-phenyl-ethylcarbamoyl)-1,2,3-triazol-1-yl]-phenyl}-2-morpholin-4-yl-isonicotinamide |
| 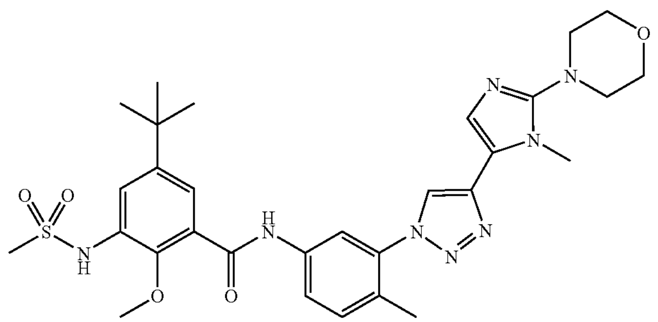 | 5-tert-Butyl-3-methanesulfonylamino-2-methoxy-N-{4-methyl-3-[4-(3-methyl-2-morpholin-4-yl-3H-imidazol-4-yl)-1,2,3-triazol-1-yl]-phenyl}-benzamide |
| 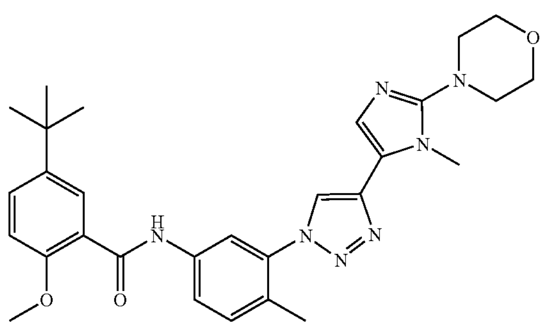 | 5-tert-Butyl-2-methoxy-N-{4-methyl-3-[4-(3-methyl-2-morpholin-4-yl-3H-imidazol-4-yl)-1,2,3-triazol-1-yl]-phenyl}-benzamide |
| 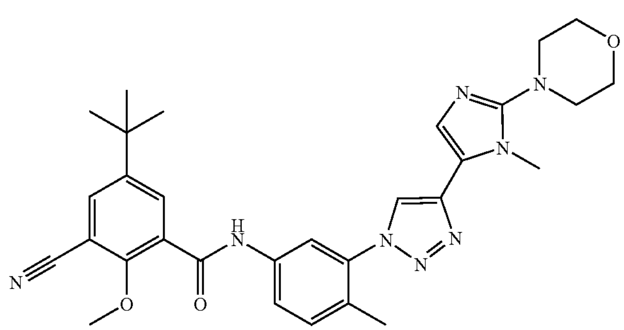 | 5-tert-Butyl-3-cyano-22-meethoxy-N-{4-methyl-3-[4-(3-methyl-2-morpholin-4-yl-3H-imidazol-4-yl)-1,2,3-triazol-1-yl]-phenyl}-benzamide |
| 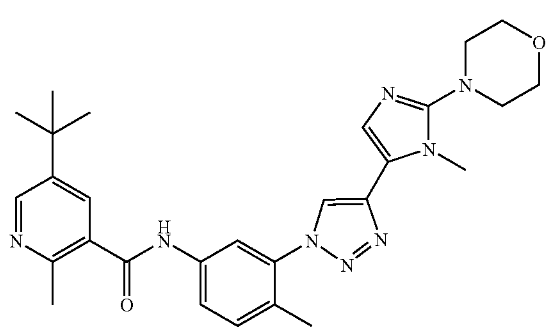 | 5-tert-Butyl-2-methyl-N-{4-methyl-3-[4-(3-methyl-2-morpholin-4-yl-3H-imidazol-4-yl)-1,2,3-triazol-1-yl]-phenyl}-nicotinamide |

| Structure | Name |
|---|---|
| 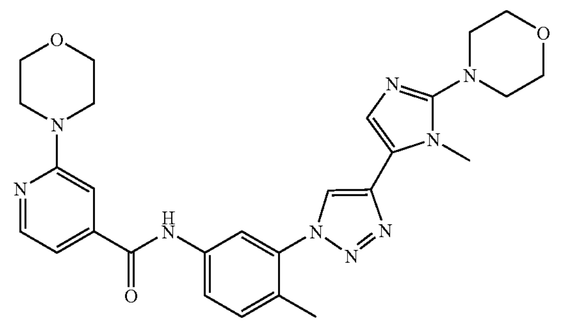 | N-{4-Methyl-3-[4-(3-methyl-2-morpholin-4-yl-3H-imidazol-4-yl)-1,2,3-triazol-1-yl]-phenyl}-2-morpholin-4-yl-isonicotinamide |

In all the compounds disclosed hereinabove in this application, in the event the nomenclature is in conflict with the structure, it shall be understood that the compound is defined by the structure.

The invention includes the use of any compounds of described above containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "C1-4alkoxy" is a C1-4alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5-8 membered monocyclic or 8-11 membered bicyclic ring containing 1-4 heteroatoms such as N,O and S. Unless otherwise stated, such heteroaryls include aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in defintions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—C1-6 alkyl radical, unless otherwise specified, this shall be understood to include —S(O)—C1-6 alkyl and —S(O)$_2$—C1-6 alkyl, likewise, —S—R$^a$ may be represented as phenyl-S(O)$_m$— when R$^a$ is phenyl and where m is 0, 1 or 2.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —CH$_2$CHF$_2$, —CF$_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and $N-(C_1-C_4 \text{ alkyl})_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

General Synthetic Methods

The invention additionally provides for methods of making the compounds of formula (I). The compounds of the invention may be prepared by the general methods and examples presented below, and methods known to those of ordinary skill in the art. Further reference in this regard may be made to U.S. Pat. No. 6,358,945, U.S. application Ser. Nos. 09/714,539, 09/834,797, 10/120,028, 10/143,322 and 10/147,675. Each of the aforementioned are incorporated in their entirety.

In all schemes, unless otherwise specified, Ar, A, B, D, $R^3$, $R^4$ and $R^6$ in the formulas shown below shall have the meanings defined for these groups in the definition of the formula (I) of the invention, described hereinabove. Intermediates used in the syntheses below are either commercially available or easily prepared by methods known to those skilled in the art. Reaction progress may be monitored by conventional methods such as thin layer chromatography (TLC). Intermediates and products may be purified by methods known in the art, including column chromatography, HPLC or recrystallization.

Compounds of formula (I) may be prepared by the methods illustrated in Scheme 1. As illustrated in Scheme 1 an aniline derivative of formula II may be coupled with the desired carboxylic acid III using standard coupling conditions known in the art (see for example M. Bodanszky, 1984, The Practice of Peptide Synthesis, Springer-Verlag). For example, one may couple III and II by treating with 1-[3-(dimethylamino)propyl]-3-ethylcarbodiimide hydrochloride (EDC) followed by 1-hydroxybenzotriazole hydrate (HOBT) in a suitable solvent such as DMF. One may also react II with a carboxylic acid derivative such as an ester or acid halide by methods known in the art. For example reaction of II with an ester IV in the presence of a suitable base provides the desired compound of formula (I)

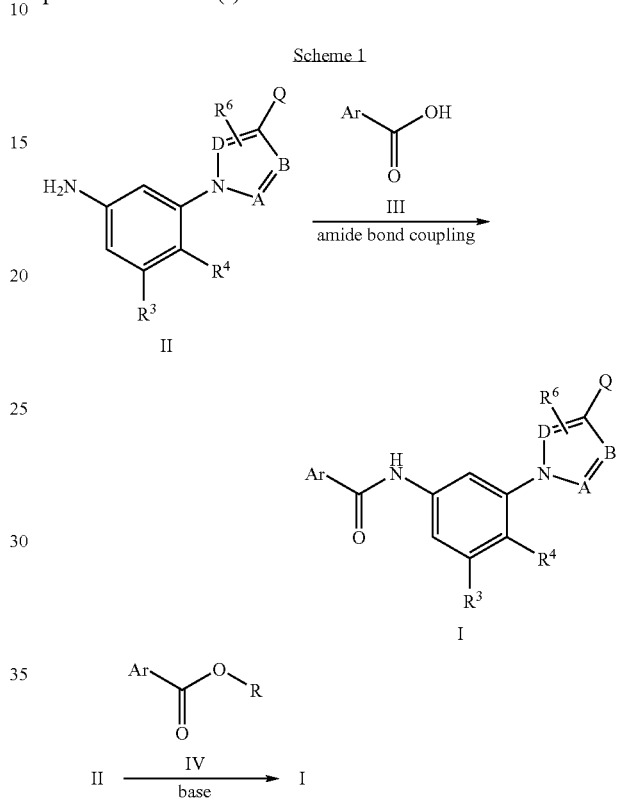

The bromo intermediate V may be used to prepare compounds of formula (I) as illustrated in Scheme 2. For example, Reaction of V with a heterocycle Q substituted with a suitable metal M, such as a boron or tin derivative, in the presence of a suitable palladium catalyst and ligand known in the art provides I where Q is an optionally substituted heterocycle. Reaction of V with an optionally substituted amine $NH_2R'$, in the presence of carbon monoxide and a suitable palladium catalyst and ligand provides I where Q is an optionally substituted amide.

-continued

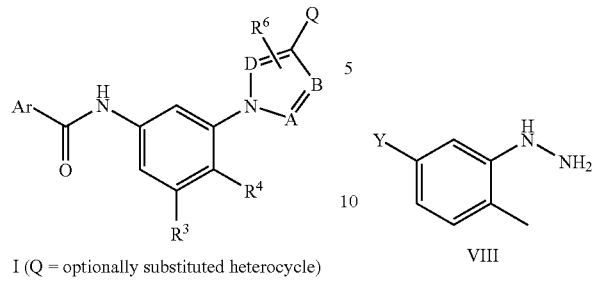

I (Q = optionally substituted heterocycle)

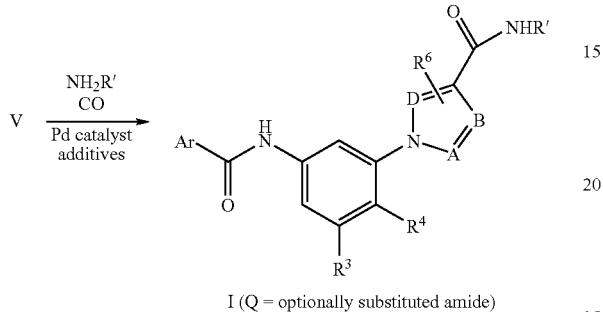

I (Q = optionally substituted amide)

Compounds of formula (I) where D=B=C and A=N may be prepared as illustrated in Scheme 3. Reaction of aryl hydrazine intermediate VI with malonaldehyde bis(dimethyl acetal), followed by bromination by methods known in the art provides VII. The bromine substituent on VII may be converted to the desired Q by methods illustrated in Scheme 2. The ester may then be converted to an amine derivative by methods known in the art such as a Schmidt reaction. Using procedures illustrated in Scheme I, one may then obtain the desired compound of formula (I). In an alternate procedure, intermediate VIII, where Y may be ArC(O)NH or $CO_2R$ or PNH, where P is a protecting group, may be reacted with intermediate IX to produce X, which is a compound of formula (I) if Y=ArC(O)NH or may be modified further by methods known in the art or described above to provide a compound of formula (I) if Y=PNH or $CO_2R$.

Scheme 3

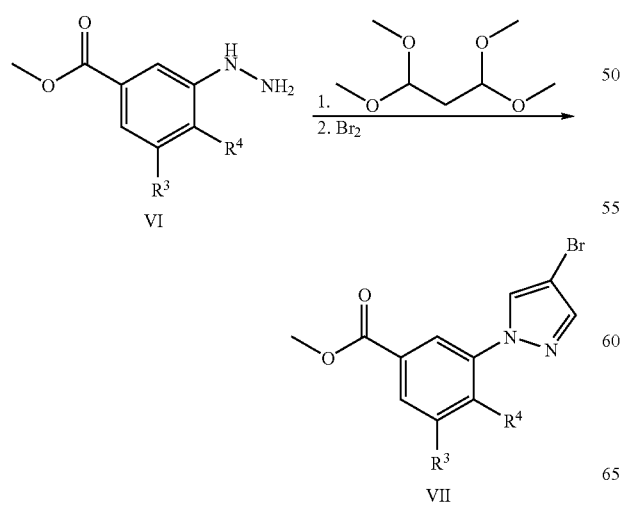

-continued

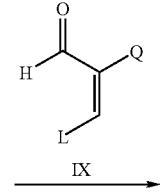

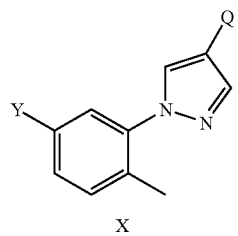

Compounds having A and D=C and B=N may be prepared as illustrated in Scheme IV. Intermediate XI, where Y is defined as above, is reacted with bromoketone XII to provide intermediate XIII. Reaction of XIII with KSCN followed by treatment with $H_2O_2$ or $HNO_3$ and $HNO_2$ provides imidazole XIV.

Scheme 4

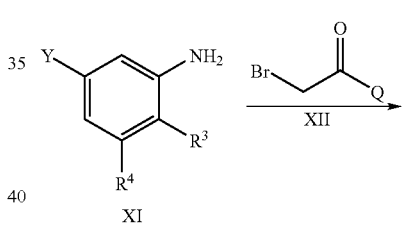

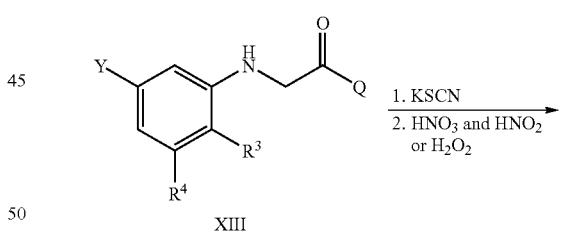

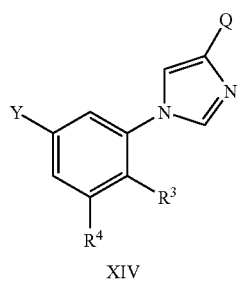

Compounds of formula (I) having A and B=N and D=C may be prepared as illustrated in Scheme 5. Intermediate XV, where P is a suitable amine protecting group known in the art such as a carbobenzoxy (CBZ) group, is reacted with a suitable reducing agent known in the art to provide intermediate XVI. Reaction of XVI with NaNO₂ followed by NaN₃ provides azide intermediate XVII. Reaction of XVII with acetylene intermediate XVIII provides triazole intermediate XIX. Deprotection of the amine by methods known in the art, for example treatment with hydrogen and a palladium catalyst in the case where P=CBZ, provides intermediate XX. This may then be converted to the desired compound of formula (I) by the methods illustrated in Scheme 1 alities on intermediate XV are reversed on intermediate XXI. The remaining steps are analogous to steps in Scheme 5.

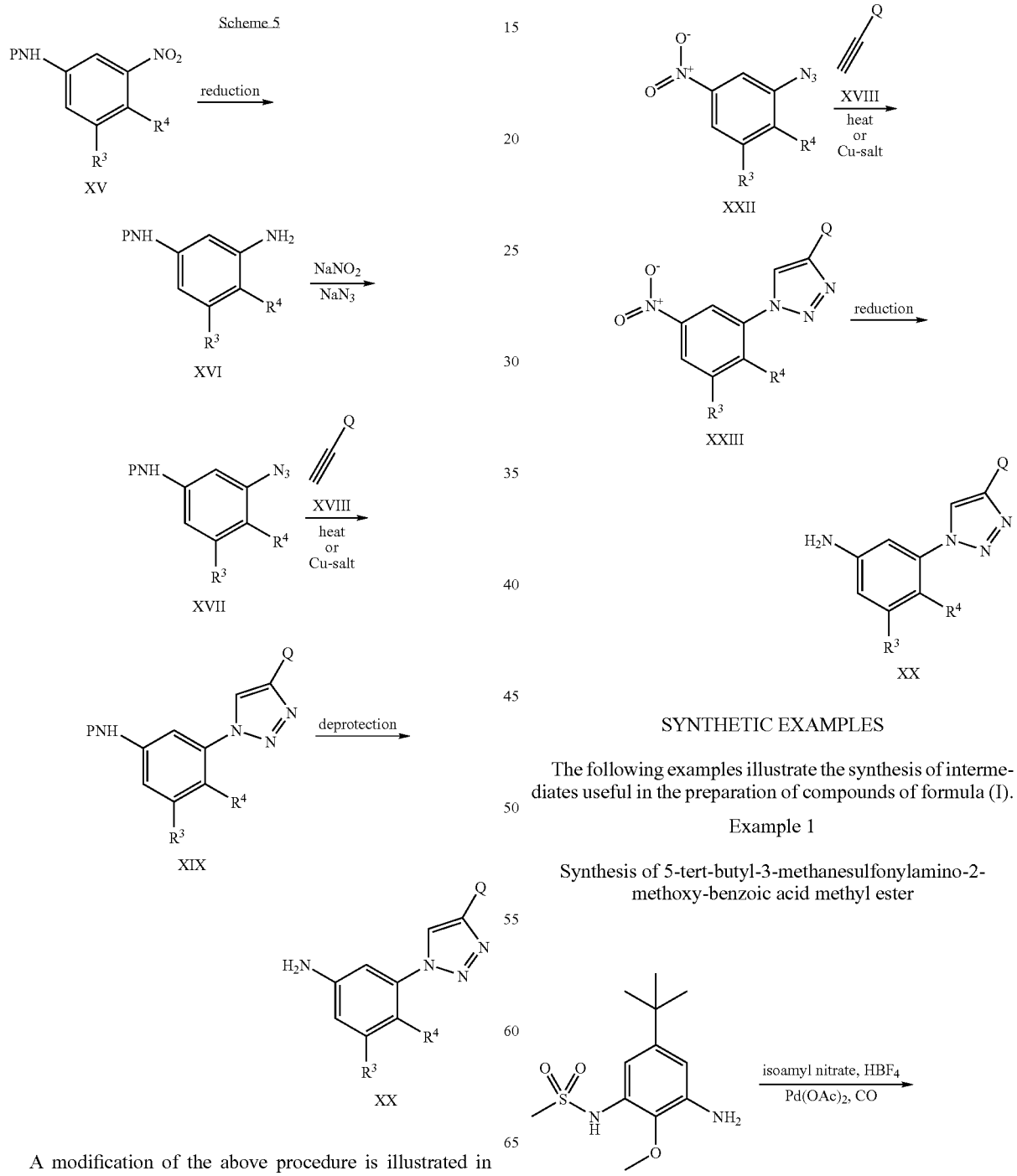

SYNTHETIC EXAMPLES

The following examples illustrate the synthesis of intermediates useful in the preparation of compounds of formula (I).

Example 1

Synthesis of 5-tert-butyl-3-methanesulfonylamino-2-methoxy-benzoic acid methyl ester A modification of the above procedure is illustrated in Scheme 6. As illustrated below, the nitro and aniline function- -continued

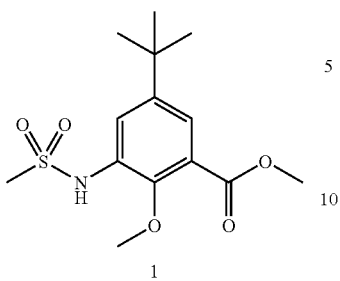

1

To a 0° C. solution of 1.34 g (4.92 mmol) of N-(3-amino-5-tert-butyl-2-methoxy-phenyl)-methanesulfonamide and 1.3 mL (10 mmol) of 48% aqueous HBF$_4$ in 10 mL of THF was added 586 mg (5 mmol) of isoamyl nitrite. The mixture was stirred 2 h, then the solvent was removed and the resulting orange semi-solid triturated with MTBE (3×10 mL). The resulting residue was taken up in MeOH and while CO was bubbled through, 60 mg of Pd(OAc)$_2$ was added, and the mixture was stirred with continuous CO bubbling for 1 h. The solution was filtered, concentrated, and purified by chromatography (0 to 50% EtOAc in hexanes) to provide the title compound as a white solid (752 mg).

Example 2

Synthesis of 4-methyl-3-[4-(5-methyl-1-phenyl-1H-pyrazol-4-yl)-imidazol-1-yl]-benzoic acid methyl ester

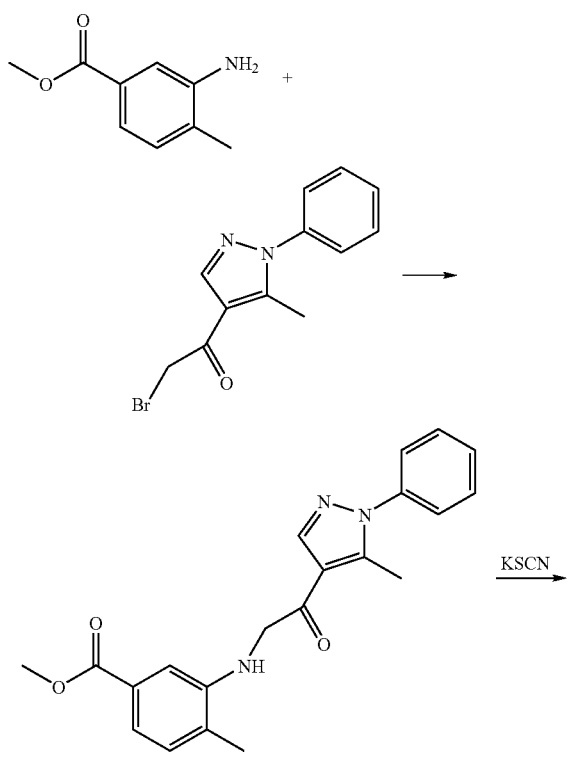

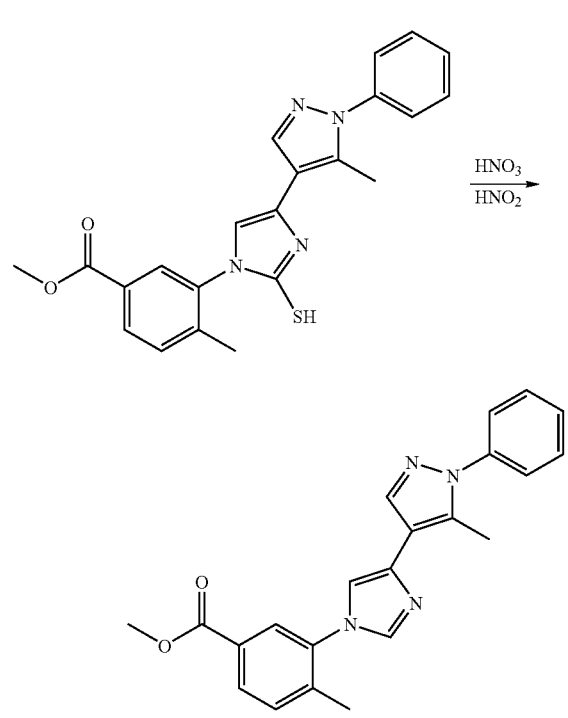

2

A solution of 2-bromo-1-(5-methyl-1-phenyl-1H-pyrazol-4-yl)-ethanone (829 mg, 2.97 mmol) and 3-amino-4-methyl benzoic acid methyl ester in 6 mL of EtOH was stirred at 75° C. for 6 h. The mixture was cooled, and the resulting precipitate was filtered and washed with cold EtOH to provide 564 mg (1.55 mmol, 52%) of 4-methyl-3-[2-(5-methyl-1-phenyl-1H-pyrazol-4-yl)-2-oxo-ethylamino]-benzoic acid methyl ester as a white powder.

A suspension of 380 mg (1.05 mmol) of 4-methyl-3-[2-(5-methyl-1-phenyl-1H-pyrazol-4-yl)-2-oxo-ethylamino]-benzoic acid methyl ester and 203 mg (2.09 mmol) of KSCN in 4 mL of HOAc was stirred at 100° C. for 4 h, when a precipitate formed. The mixture was cooled to room temperature, filtered, and washed with cold MeOH to provide 283 mg of 3-[2-mercapto-4-(5-methyl-1-phenyl-1H-pyrazol-4-yl)-imidazol-1-yl]-4-methyl-benzoic acid methyl ester (0.70 mmol, 67%). ESI MS m/z 405 [C$_{22}$H$_{20}$N$_4$O$_2$S+H]$^+$.

To 1 mL of 20% HNO$_3$ was added 28 mg of HNO$_2$. This mixture was then added to 3-[2-mercapto-4-(5-methyl-1-phenyl-1H-pyrazol-4-yl)-imidazol-1-yl]-4-methyl-benzoic acid methyl ester (280 mg, 0.69 mmol) suspended in 5 mL of rapidly stirring HOAc over 15 min. After stirring an additional 5 min, the solution was poured into ice-cold water. The pH was adjusted to about 7 with NaHCO$_3$, and the mixture was extracted with EtOAc. The extract was washed once with brine, dried with Na$_2$SO$_4$, filtered, and concentrated. The resulting residue was chromatographed (5-60% EtOAc in hexanes) to provide 210 mg (0.56 mmol, 82%) of 4-methyl-3-[4-(5-methyl-1-phenyl-1H-pyrazol-4-yl)-imidazol-1-yl]-benzoic acid methyl ester. ESI MS m/z 373 [C$_{22}$H$_{20}$N$_4$O$_2$+H]$^+$.

Example 3

Synthesis of 3-[4-(5-ethyl-1-phenyl-1H-pyrazol-4-yl)-imidazol-1-yl]-4-methyl-phenylamine

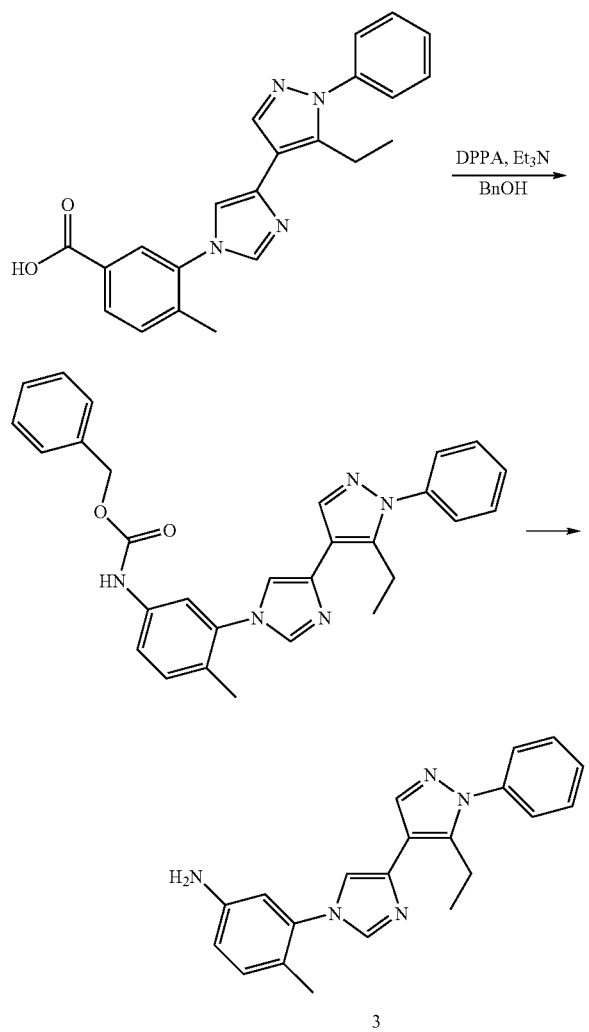

3-[4-(5-Ethyl-1-phenyl-1H-pyrazol-4-yl)-imidazol-1-yl]-4-methyl-benzoic acid (prepared by hydrolysis of the methyl ester which was prepared by the method described in Example 2, using the 5-ethylpyrazole intermediate) (780 mg, 2.09 mmol), DPPA (0.52 mL, 2.4 mmol), and Et₃N (0.37 mL, 2.7 mmol) were suspended in dry toluene (10 mL) under N₂ and stirred for 1 h after which time a clear solution had formed. The reaction mixture was placed into a 100° C. pre-heated oil bath and stirred under N₂ for 75 min. Then, benzyl alcohol (1 mL) was added and the reaction stirred at 110° C. for 6 h. The reaction was cooled, concentrated, and purified by chromatography (0 to 75% EtOAc in hexanes) to give the {3-[4-(5-ethyl-1-phenyl-1H-pyrazol-4-yl)-imidazol-1-yl]-4-methyl-phenyl}-carbamic acid benzyl ester as a white foam (695 mg, 70%).

The benzyl ester intermediate from above (680 mg, 1.42 mmol) was dissolved in 50 mL of EtOH. Ammonium formate (2 g) and Pd/C (100 mg) were added and the mixture was heated to 70° C. for 3 h. The mixture was cooled and concentrated, then the residue taken up in water (10 mL), saturated NaHCO₃ (15 mL) and EtOAc (250 mL). The organic layer was separated, dried over MgSO₄, filtered, concentrated, and purified by chromatography (0 to 100% EtOAc in hexanes) to give the title compound as a white foam (230 mg, 47%).

Example 4

Synthesis of 5-tert-butyl-N-{3-[4-(5-ethyl-1-phenyl-1H-pyrazol-4-yl)-imidazol-1-yl]-4-methyl-phenyl}-3-methanesulfonylamino-2-methoxy-benzamide

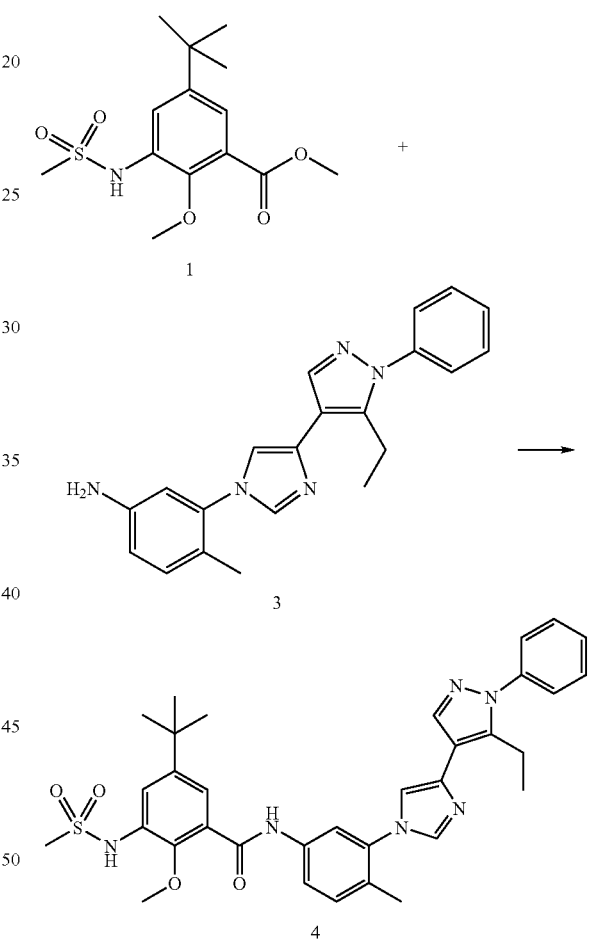

3-[4-(5-Ethyl-1-phenyl-1H-pyrazol-4-yl)-imidazol-1-yl]-4-methyl-phenylamine (Example 3) (80 mg, 0.23 mmol) was dissolved in THF (5 mL) under N₂ and 0.9 mL of 1 M LiH-MDS (0.9 mmol) was slowly added. After stirring for 5 min, a solution of 73.5 mg (0.23 mmol) of 5-tert-butyl-3-methanesulfonylamino-2-methoxy-benzoic acid methyl ester (Example 1) in 5 mL of THF was added. The mixture was stirred at room temperature for 45 min, then saturated NaHCO₃ (10 mL) was slowly added. The resulting mixture was then extracted with CH₂Cl₂ (100 mL). Chromatography (30 to 100% EtOAc in hexanes) provided the title compound as a tan foam (58 mg, 40%). ESI MS m/z 627 [C₃₄H₃₈N₆O₄S+H]⁺.

Example 5

Synthesis of 5-tert-butyl-N-{3-[4-(5-ethyl-1-phenyl-1H-pyrazol-4-yl)-imidazol-1-yl]-4-methyl-phenyl}-2-methoxy-benzamide

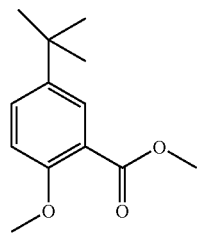

+

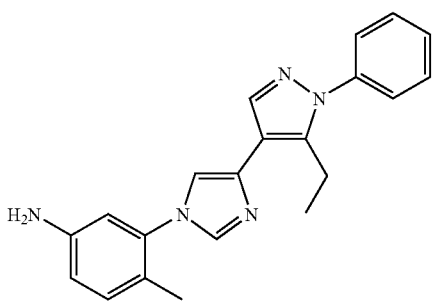

3

→

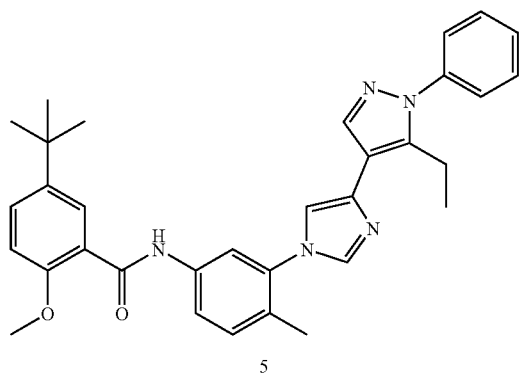

5

3-[4-(5-Ethyl-1-phenyl-1H-pyrazol-4-yl)-imidazol-1-yl]-4-methyl-phenylamine (Example 3) (80 mg, 0.23 mmol) was dissolved in THF (5 mL) under $N_2$ and 0.9 mL of 1 M LiHMDS (0.9 mmol) was slowly added. After stirring for 5 min, a solution of 51.8 mg (0.23 mmol) of 5-tert-butyl-2-methoxy-benzoic acid methyl ester in 5 mL of THF was added. The mixture was stirred at for 45 min, then saturated $NaHCO_3$ (10 mL) was slowly added. The resulting mixture was then extracted with $CH_2Cl_2$ (100 mL). Chromatography (30 to 100% EtOAc in hexanes) provided the title compound as a tan foam (62 mg, 50%). ESI MS m/z 534 $[C_{33}H_{35}N_5O_2+H]^+$.

Examples 6 and 7 illustrate procedures for the synthesis of benzoic acid intermediates that are useful for preparation of compounds of formula (I) having an imidazole ring (formula IA)

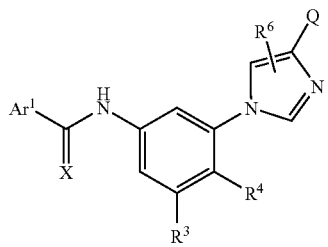

IA

The benzoic acid may be converted to an aniline by methods known in the art, for example a Schmidt reaction or Curtius rearrangement, and the resulting aniline used in methods described in the previous section to prepare compounds of formula IA.

Example 6

Synthesis of 4-methyl-3-(4-pyridin-3-yl-imidazol-1-yl)-benzoic acid

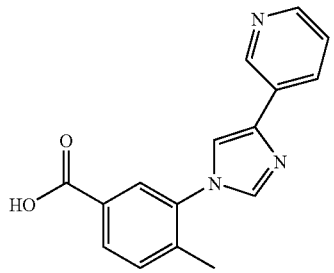

A mixture of 4-methyl-3-(2-oxo-2-pyridin-3-yl-ethylamino)-benzoic acid methyl ester (84.5 mg, 0.297 mmol) and KSCN (58 mg; 0.59 mmol) in 1.5 mL of HOAc were heated to 100° C. for 2 h. The mixture was then poured into water and carefully brought to pH 8 with NaOH. The mixture was immediately extracted with EtOAc, and the extract washed with brine. The washes were extracted once more with EtOAc, and the combined extracts were dried with $Na_2SO_4$, filtered, and concentrated to provide 3-(2-mercapto-4-pyridin-3-yl-imidazol-1-yl)-4-methyl-benzoic acid methyl ester (90 mg, 0.28 mmol; 93%). ESI MS m/z 326 $[C_{17}H_{15}N_3O_2S+H]^+$.

To a suspension of 85 mg (0.261 mmol) of 3-(2-mercapto-4-pyridin-3-yl-imidazol-1-yl)-4-methyl-benzoic acid methyl ester in 1.8 mL of water was added 0.68 mL of concentrated $HNO_3$ and 2 mg of $NaNO_2$. After 2 h, the mixture was cooled to 0° C. and 4N NaOH was added until the pH reached about 10. The mixture was stirred for 30 min then HOAc was added until the pH reached about 6. The resulting precipitate was filtered, washed with water and dried to provide 16 mg (0.057 mmol, 22%) of the title compound.

Example 7

Synthesis of 1-(5-carboxy-2-methyl-phenyl)-1H-imidazole-4-carboxylic acid ethyl ester

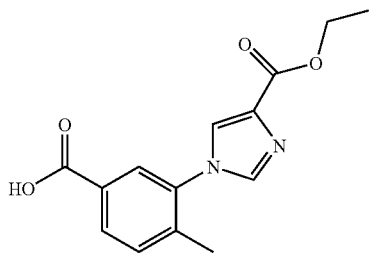

A slurry of 3-amino-4-methylbenzoic acid (5.00 g, 33.1 mmol), ethyl orthoformate (5.94 mL), ethyl nitroacetate (3.67 mL), and acetic acid (0.2 mL) was heated to 100° C. with stirring for 3.5 h. The mixture was cooled to 85° C. and an additional 66 mL each of ethyl orthoformate and acetic acid were added followed by 5.54 g (99.2 mmol) of iron powder. The mixture was heated to reflux and stirred for 1 h, when an additional 5.54 g of iron powder was added in three portions, each portion after 1 h of stirring at reflux. The mixture was then heated for an additional 6 h before being cooled to room temperature. The mixture was filtered and the solids were washed with EtOAc. The filtrate was collected and concentrated to afford a brown semisolid. The solid was triturated with Et₂O/EtOAc to provide 1.93 g (7.04 mmol, 21.3%) of the title compound as a tan solid.

Examples 8-10 illustrate procedures for the synthesis of benzoic acid intermediates or derivatives that are useful for preparation of compounds of formula (I) having a pyrazole ring (formula IB)

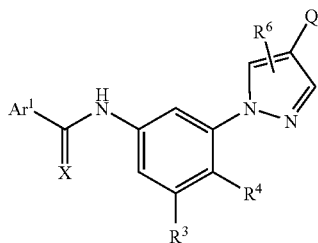

IB

Example 8

Synthesis of 3-(4-bromo-pyrazol-1-yl)-4-methyl-benzoic acid ethyl ester

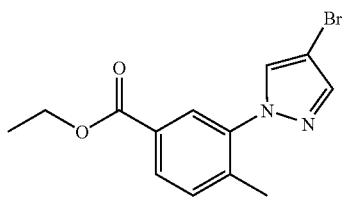

A solution of 3-hydrazino-4-methyl benzoic acid (1.0 g, 4.93 mmol), malonaldehyde(bismethylacetate) (0.82 mL, 4.93 mmol), and concentrated HCl (1 mL) in EtOH (20 mL) was heated to reflux for 4 h. After cooling to room temperature, the reaction was poured into ice water, neutralized with 2N NaOH, and extracted with CH₂Cl₂ (3×). The organic layers were dried over Na₂SO₄, filtered and concentrated to afford 4-methyl-3-pyrazol-1-yl-benzoic acid ethyl ester (536 mg, 47%) as a yellow oil. A solution of the pyrazole (536 mg, 2.33 mmol) and bromine (0.167 mL, 3.26 mmol) in CHCl₃ (15 mL) was refluxed for 4.5 h then cooled to room temperature. The solvent was evaporated to an orange oil. Purification using chromatography on silica gel (1:1 EtOAc/hexanes) yielded 3-(4-bromo-pyrazol-1-yl)-4-methyl-benzoic acid ethyl ester (0.739 g, 99%) as a yellow solid.

Example 9

Synthesis of 1-(5-carboxy-2-methyl-phenyl)-1H-pyrazole-4-carboxylic acid ethyl ester

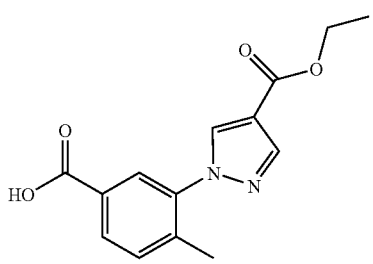

A solution of 2-formyl-3-oxo-propionic acid ethyl ester (S. H. Bertz et al., *J. Org. Chem.*, 1982, 47, 2216) (1.44 g, 10 mmol) in EtOH (10 mL) was cooled in an ice bath. A slurry of 3-hydrazino-4-methyl-benzoic acid hydrochloride (2.02 g, 10 mmol) in EtOH (50 mL) was added and the reaction was stirred overnight. The EtOH was removed under reduced pressure and the residue partitioned between water and CH₂Cl₂. The layers were separated and the organic layer washed with brine. The organic layer was dried over Na₂SO₄, filtered, and concentrated. Hexanes were added and the solution concentrated. The resulting solid was collected by vacuum filtration, washed with hexanes and dried under vacuum to provide 1-(5-carboxy-2-methyl-phenyl)-1H-pyrazole-4-carboxylic acid ethyl ester (1.86 g, 68%) as a yellow solid: ESI MS m/z 275 [$C_{14}H_{14}N_2O_4$+H]⁺.

Example 10

Synthesis of 4-methyl-3-[4-(3-methyl-3H-imidazol-4-yl)-pyrazol-1-yl]-benzoic acid ethyl ester

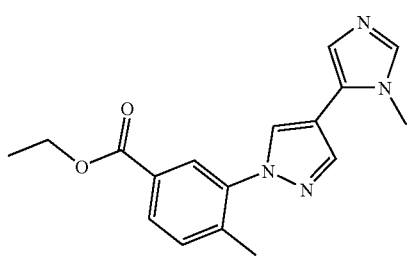

3-(4-Bromo-pyrazol-1-yl)-4-methyl-benzoic acid ethyl ester (Example 8) (366 mg, 1.18 mmol) was dissolved in dioxane (2 mL) and flushed with nitrogen. 1-Methyl-5-tributylstannanyl-1H-imidazole (366 mg, 0.986 mmol) was added to the reaction flask in dioxane (0.5 mL) then the flask was purged with N₂. After Pd(PPh₃)₄ (85 mg, 0.074 mmol) was added, the reaction was heated to 100° C. in a sealed tube. The reaction mixture was stirred with a 10% KF solution for 30 min then diluted with EtOAc. The layers were separated and the aqueous layer extracted with EtOAc (3×). The organic layers were combined, dried over Na₂SO₄, and concentrated. The resulting residue was purified by chromatography on silica gel (5% MeOH/CH₂Cl₂) to give the title compound (81 mg, 22%) as a colorless oil.

Examples 11-13 illustrate procedures for the synthesis of benzoic acid intermediates or derivatives that are useful for preparation of compounds of formula (I) having a 1,2,3-triazole ring (formula IC)

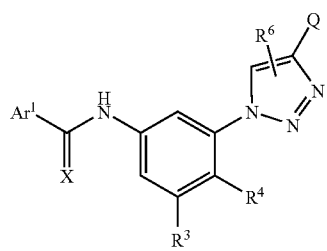

IC

The following alkyne intermediates were prepared by the methods described in case 60/551,445.

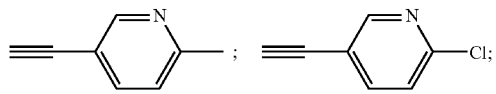

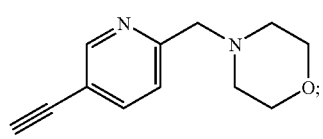

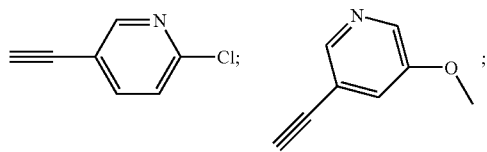

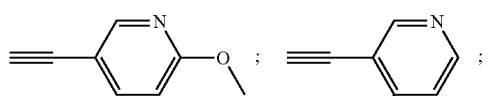

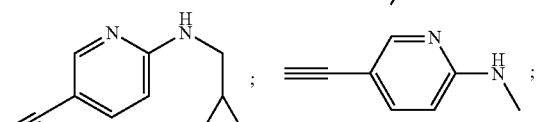

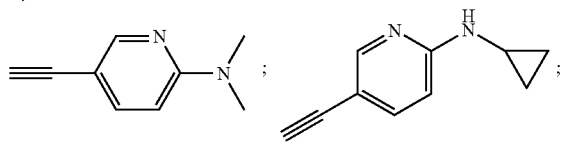

-continued

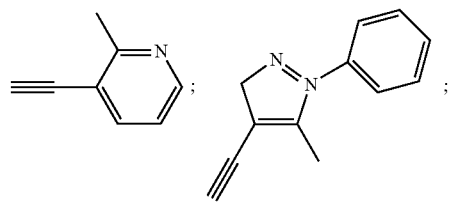

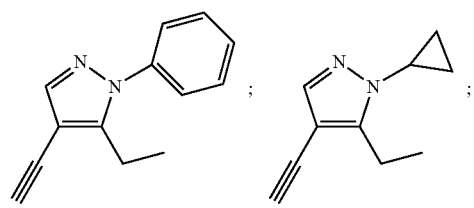

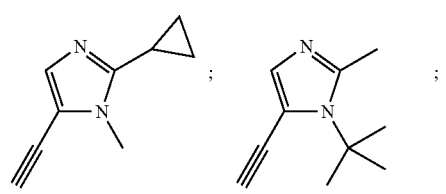

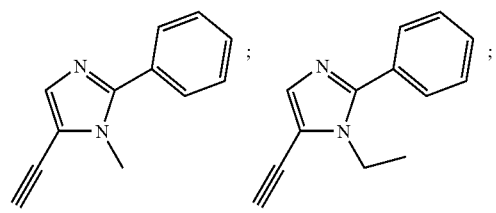

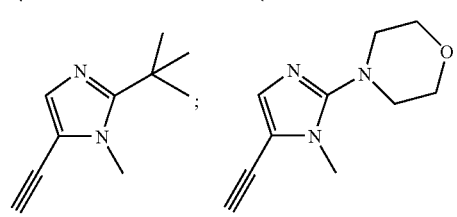

Example 11

Synthesis of 3-[4-(6-chloro-pyridin-3-yl)-1,2,3-triazol-1-yl]-4-methyl-benzoic acid

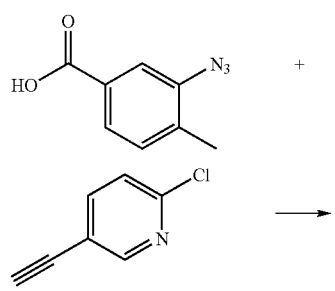

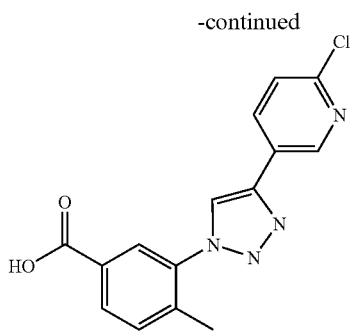

To a suspension of 308 mg (1.75 mmol) of 3-azido-4-methyl benzoic acid (U.S. Ser. No. 04/102,492) and 240 mg (1.75 mmol) of 2-chloro-5-ethynylpyridine in 1 mL of water and 2 mL of EtOH was added 243 μL (1.75 mmol) of Et₃N. To this solution was added 1.75 mL of 1M aqueous sodium ascorbate followed by 1.75 mL of 0.1 M aqueous of CuSO₄ and the resulting yellow suspension was stirred for two days. A 1 M solution of acetic acid in water (1.75 mL) was added along with an additional 2 mL of water. The suspension was stirred for 1 h, then was filtered, washed with water (2×2 mL) and hexanes (2×10 mL), and dried under suction to provide 470 mg of 3-[4-(6-chloro-pyridin-3-yl)-1,2,3-triazol-1-yl]-4-methyl-benzoic acid.

Examples 12 and 13

Synthesis of 3-[4-(2,2-dimethyl-propylcarbamoyl)-[1,2,3]triazol-1-yl]-4-methyl-benzoic acid and 4-methyl-3-[4-(1-phenyl-ethylcarbamoyl)-[1,2,3]triazol-1-yl]-benzoic acid

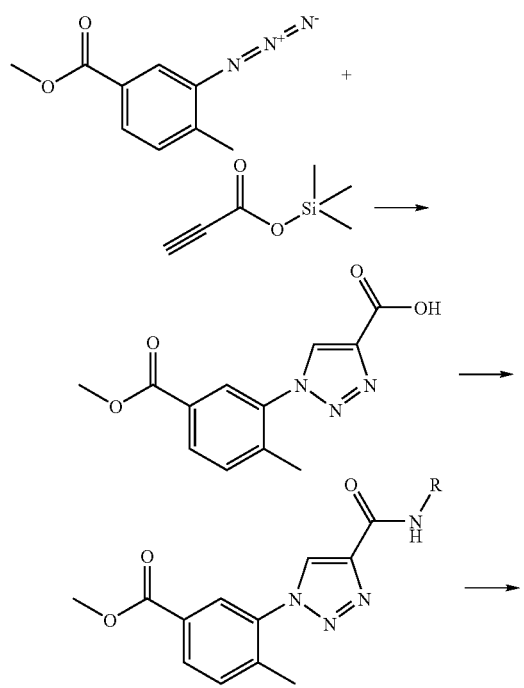

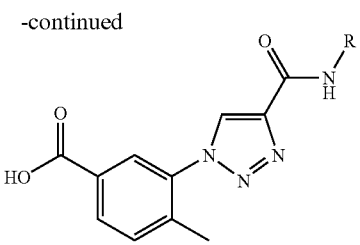

3-Azido-4-methyl-benzoic acid methyl ester (878 mg, 4.60 mmol) and trimethylsilyl propiolate (777 mg, 5.05 mmol) were heated to 80° C. in a sealed tube overnight. The tube was cooled and the contents were mixed with 20 mL of MeOH. After 2 h, the mixture was poured into rapidly stirring cold water, and the resulting precipitate was filtered and dried under air to provide 823 mg of 1-(5-methoxycarbonyl-2-methyl-phenyl)-1H-[1,2,3]triazole-4-carboxylic acid.

The above triazole carboxylic acid (780 mg, 2.99 mmol) was dissolved in 6 mL of DMF and stirred at room temperature while 1.8 g (4.73 mmol) of HATU was added. Once the HATU dissolved, 1.69 mL of i-Pr₂NEt was added slowly, and the reaction vessel was placed in a 0° C. bath. An amine (4.73 mmol) was then added slowly, and the vessel was warmed slowly to room temperature. After 30 min, the mixture was poured into ice-cold water. When a precipitate formed, it was filtered and washed with water. Otherwise, the mixture was extracted twice with EtOAc, and the extracts washed with water and brine. The combined organic extracts were dried with Na₂SO₄, filtered and concentrated. When necessary, the resulting red residue was chromatographed to provide the pure ester. The resulting ester was dissolved in 12 mL of MeOH and 2.23 mL of 4 M NaOH was slowly added. After stirring for 2 h, half the solvent was removed and 100 mL of water was added. The pH was adjusted to <2 by the addition of concentrated HCl. The resulting precipitate was filtered and dried, first under a flow of air, and second in vacuo to provide the desired compound:

| Example | Amine (RNH₂) | Product |
|---------|--------------|---------|
| 12 | neopentylamine | 3-[4-(2,2-Dimethyl-propylcarbamoyl)-[1,2,3]triazol-1-yl]-4-methyl-benzoic acid |
| 13 | 1-phenylethylamine | 4-Methyl-3-[4-(1-phenyl-ethylcarbamoyl)-[1,2,3]triazol-1-yl]-benzoic acid |

Using the methods described above, and with materials that are described above, commercially available, or described in the literature, the following examples may also be prepared:
5-tert-Butyl-3-methanesulfonylamino-2-methoxy-N-[4-methyl-3-(4-pyridin-3-yl-1,2,3-triazol-1-yl)-phenyl]-benzamide;
5-tert-Butyl-2-methoxy-N-[4-methyl-3-(4-pyridin-3-yl-1,2,3-triazol-1-yl)-phenyl]-benzamide;
5-tert-Butyl-3-cyano-2-methoxy-N-[4-methyl-3-(4-pyridin-3-yl-1,2,3-triazol-1-yl)-phenyl]-benzamide;
5-tert-Butyl-N-(3-{4-[6-(cyclopropylmethyl-amino)-pyridin-3-yl]-1,2,3-triazol-1-yl}-4-methyl-phenyl)-3-methanesulfonylamino-2-methoxy-benzamide;
5-tert-Butyl-N-(3-{4-[6-(cyclopropylmethyl-amino)-pyridin-3-yl]-1,2,3-triazol-1-yl}-4-methyl-phenyl)-2-methoxy-benzamide;

5-tert-Butyl-3-cyano-N-(3-{4-[6-(cyclopropylmethyl-amino)-pyridin-3-yl]-1,2,3-triazol-1-yl}-4-methyl-phenyl)-2-methoxy-benzamide;

5-tert-Butyl-3-methanesulfonylamino-2-methoxy-N-{3-[4-(5-methoxy-pyridin-3-yl)-1,2,3-triazol-1-yl]-4-methyl-phenyl}-benzamide;

5-tert-Butyl-2-methoxy-N-{3-[4-(5-methoxy-pyridin-3-yl)-1,2,3-triazol-1-yl]-4-methyl-phenyl}-benzamide;

5-tert-Butyl-3-cyano-2-methoxy-N-{3-[4-(5-methoxy-pyridin-3-yl)-1,2,3-triazol-1-yl]-4-methyl-phenyl}-benzamide;

N-{3-[4-(5-Methoxy-pyridin-3-yl)-1,2,3-triazol-1-yl]-4-methyl-phenyl}-2-morpholin-4-yl-isonicotinamide;

N-{3-[4-(5-Methoxy-pyridin-3-yl)-1,2,3-triazol-1-yl]-4-methyl-phenyl}-3-morpholin-4-yl-benzamide;

3-Fluoro-N-{3-[4-(5-methoxy-pyridin-3-yl)-1,2,3-triazol-1-yl]-4-methyl-phenyl}-5-morpholin-4-yl-benzamide;

5-tert-Butyl-2-methyl-2H-pyrazole-3-carboxylic acid {3-[4-(5-methoxy-pyridin-3-yl)-1,2,3-triazol-1-yl]-4-methyl-phenyl}-amide;

5-tert-Butyl-2-p-tolyl-2H-pyrazole-3-carboxylic acid {3-[4-(5-methoxy-pyridin-3-yl)-1,2,3-triazol-1-yl]-4-methyl-phenyl}-amide;

2-Phenyl-cyclopropanecarboxylic acid {3-[4-(5-methoxy-pyridin-3-yl)-1,2,3-triazol-1-yl]-4-methyl-phenyl}-amide;

N-{3-[4-(5-Methoxy-pyridin-3-yl)-1,2,3-triazol-1-yl]-4-methyl-phenyl}-2-pyrrolidin-1-yl-isonicotinamide;

N-{3-[4-(5-Methoxy-pyridin-3-yl)-1,2,3-triazol-1-yl]-4-methyl-phenyl}-3-pyrrolidin-1-yl-benzamide;

3-Fluoro-N-{3-[4-(5-methoxy-pyridin-3-yl)-1,2,3-triazol-1-yl]-4-methyl-phenyl}-5-pyrrolidin-1-yl-benzamide;

5-tert-Butyl-N-{3-[4-(5-methoxy-pyridin-3-yl)-1,2,3-triazol-1-yl]-4-methyl-phenyl}-2-methyl-nicotinamide;

N-[4-Methyl-3-(4-pyridin-3-yl-1,2,3-triazol-1-yl)-phenyl]-2-morpholin-4-yl-isonicotinamide;

N-[4-Methyl-3-(4-pyridin-3-yl-1,2,3-triazol-1-yl)-phenyl]-2-pyrrolidin-1-yl-isonicotinamide;

N-[4-Methyl-3-(4-pyridin-3-yl-1,2,3-triazol-1-yl)-phenyl]-3-morpholin-4-yl-benzamide;

N-[4-Methyl-3-(4-pyridin-3-yl-1,2,3-triazol-1-yl)-phenyl]-3-pyrrolidin-1-yl-benzamide;

3-Fluoro-N-[4-methyl-3-(4-pyridin-3-yl-1,2,3-triazol-1-yl)-phenyl]-5-morpholin-4-yl-benzamide;

3-Fluoro-N-[4-methyl-3-(4-pyridin-3-yl-1,2,3-triazol-1-yl)-phenyl]-5-pyrrolidin-1-yl-benzamide;

5-tert-Butyl-2-methyl-2H-pyrazole-3-carboxylic acid [4-methyl-3-(4-pyridin-3-yl-1,2,3-triazol-1-yl)-phenyl]-amide;

5-tert-Butyl-2-p-tolyl-2H-pyrazole-3-carboxylic acid [4-methyl-3-(4-pyridin-3-yl-1,2,3-triazol-1-yl)-phenyl]-amide;

2-Phenyl-cyclopropanecarboxylic acid [4-methyl-3-(4-pyridin-3-yl-1,2,3-triazol-1-yl)-phenyl]-amide;

5-tert-Butyl-2-methyl-N-[4-methyl-3-(4-pyridin-3-yl-1,2,3-triazol-1-yl)-phenyl]-nicotinamide;

N-(3-{4-[6-(Cyclopropylmethyl-amino)-pyridin-3-yl]-1,2,3-triazol-1-yl}-4-methyl-phenyl)-2-morpholin-4-yl-isonicotinamide;

N-(3-{4-[6-(Cyclopropylmethyl-amino)-pyridin-3-yl]-1,2,3-triazol-1-yl}-4-methyl-phenyl)-2-pyrrolidin-1-yl-isonicotinamide;

N-(3-{4-[6-(Cyclopropylmethyl-amino)-pyridin-3-yl]-1,2,3-triazol-1-yl}-4-methyl-phenyl)-3-morpholin-4-yl-benzamide;

N-(3-{4-[6-(Cyclopropylmethyl-amino)-pyridin-3-yl]-1,2,3-triazol-1-yl}-4-methyl-phenyl)-3-pyrrolidin-1-yl-benzamide;

N-(3-{4-[6-(Cyclopropylmethyl-amino)-pyridin-3-yl]-1,2,3-triazol-1-yl}-4-methyl-phenyl)-3-fluoro-5-morpholin-4-yl-benzamide;

N-(3-{4-[6-(Cyclopropylmethyl-amino)-pyridin-3-yl]-1,2,3-triazol-1-yl}-4-methyl-phenyl)-3-fluoro-5-pyrrolidin-1-yl-benzamide;

5-tert-Butyl-2-methyl-2H-pyrazole-3-carboxylic acid (3-{4-[6-(cyclopropylmethyl-amino)-pyridin-3-yl]-1,2,3-triazol-1-yl}-4-methyl-phenyl)-amide;

5-tert-Butyl-2-p-tolyl-2H-pyrazole-3-carboxylic acid (3-{4-[6-(cyclopropylmethyl-amino)-pyridin-3-yl]-1,2,3-triazol-1-yl}-4-methyl-phenyl)-amide;

2-Phenyl-cyclopropanecarboxylic acid (3-{4-[6-(cyclopropylmethyl-amino)-pyridin-3-yl]-1,2,3-triazol-1-yl}-4-methyl-phenyl)-amide;

5-tert-Butyl-N-(3-{4-[6-(cyclopropylmethyl-amino)-pyridin-3-yl]-1,2,3-triazol-1-yl}-4-methyl-phenyl)-2-methyl-nicotinamide;

5-tert-Butyl-2-methoxy-N-[4-methyl-3-(4-pyridin-3-yl-imidazol-1-yl)-phenyl]-benzamide;

5-tert-Butyl-3-methanesulfonylamino-2-methoxy-N-[4-methyl-3-(4-pyridin-3-yl-imidazol-1-yl)-phenyl]-benzamide;

5-tert-Butyl-3-cyano-2-methoxy-N-[4-methyl-3-(4-pyridin-3-yl-imidazol-1-yl)-phenyl]-benzamide;

5-tert-Butyl-2-methoxy-N-{4-methyl-3-[4-(5-methyl-1-phenyl-1H-pyrazol-4-yl)-1,2,3-triazol-1-yl]-phenyl}-benzamide;

5-tert-Butyl-3-methanesulfonylamino-2-methoxy-N-{4-methyl-3-[4-(5-methyl-1-phenyl-1H-pyrazol-4-yl)-1,2,3-triazol-1-yl]-phenyl}-benzamide;

5-tert-Butyl-3-cyano-2-methoxy-N-{4-methyl-3-[4-(5-methyl-1-phenyl-1H-pyrazol-4-yl)-1,2,3-triazol-1-yl]-phenyl}-benzamide;

N-{4-Methyl-3-[4-(5-methyl-1-phenyl-1H-pyrazol-4-yl)-1,2,3-triazol-1-yl]-phenyl}-2-morpholin-4-yl-isonicotinamide;

N-{4-Methyl-3-[4-(5-methyl-1-phenyl-1H-pyrazol-4-yl)-1,2,3-triazol-1-yl]-phenyl}-2-pyrrolidin-1-yl-isonicotinamide;

N-{4-Methyl-3-[4-(5-methyl-1-phenyl-1H-pyrazol-4-yl)-1,2,3-triazol-1-yl]-phenyl}-3-morpholin-4-yl-benzamide;

N-{4-Methyl-3-[4-(5-methyl-1-phenyl-1H-pyrazol-4-yl)-1,2,3-triazol-1-yl]-phenyl}-3-pyrrolidin-1-yl-benzamide;

3-Fluoro-N-{4-methyl-3-[4-(5-methyl-1-phenyl-1H-pyrazol-4-yl)-1,2,3-triazol-1-yl]-phenyl}-5-morpholin-4-yl-benzamide;

3-Fluoro-N-{4-methyl-3-[4-(5-methyl-1-phenyl-1H-pyrazol-4-yl)-1,2,3-triazol-1-yl]-phenyl}-5-pyrrolidin-1-yl-benzamide;

5-tert-Butyl-2-methyl-2H-pyrazole-3-carboxylic acid {4-methyl-3-[4-(5-methyl-1-phenyl-1H-pyrazol-4-yl)-1,2,3-triazol-1-yl]-phenyl}-amide;

5-tert-Butyl-2-p-tolyl-2H-pyrazole-3-carboxylic acid {4-methyl-3-[4-(5-methyl-1-phenyl-1H-pyrazol-4-yl)-1,2,3-triazol-1-yl]-phenyl}-amide;

2-Phenyl-cyclopropanecarboxylic acid {4-methyl-3-[4-(5-methyl-1-phenyl-1H-pyrazol-4-yl)-1,2,3-triazol-1-yl]-phenyl}-amide;

5-tert-Butyl-2-methyl-N-{4-methyl-3-[4-(5-methyl-1-phenyl-1H-pyrazol-4-yl)-1,2,3-triazol-1-yl]-phenyl}-nicotinamide;

5-tert-Butyl-N-{3-[4-(1-isopropyl-5-methyl-1H-pyrazol-4-yl)-1,2,3-triazol-1-yl]-4-methyl-phenyl}-3-methanesulfonylamino-2-methoxy-benzamide;

5-tert-Butyl-N-{3-[4-(1-isopropyl-5-methyl-1H-pyrazol-4-yl)-1,2,3-triazol-1-yl]-4-methyl-phenyl}-2-methoxy-benzamide;

5-tert-Butyl-3-cyano-N-{3-[4-(1-isopropyl-5-methyl-1H-pyrazol-4-yl)-1,2,3-triazol-1-yl]-4-methyl-phenyl}-2-methoxy-benzamide;

N-{3-[4-(1-Isopropyl-5-methyl-1H-pyrazol-4-yl)-1,2,3-triazol-1-yl]-4-methyl-phenyl}-2-morpholin-4-yl-isonicotinamide;

5-tert-Butyl-N-{3-[4-(1-isopropyl-5-methyl-1H-pyrazol-4-yl)-1,2,3-triazol-1-yl]-4-methyl-phenyl}-2-methyl-nicotinamide;

5-tert-Butyl-N-{3-[4-(1-cyclopropyl-5-ethyl-1H-pyrazol-4-yl)-1,2,3-triazol-1-yl]-4-methyl-phenyl}-3-methanesulfonylamino-2-methoxy-benzamide;

5-tert-Butyl-N-{3-[4-(1-cyclopropyl-5-ethyl-1H-pyrazol-4-yl)-1,2,3-triazol-1-yl]-4-methyl-phenyl}-2-methoxy-benzamide;

5-tert-Butyl-3-cyano-N-{3-[4-(1-cyclopropyl-5-ethyl-1H-pyrazol-4-yl)-1,2,3-triazol-1-yl]-4-methyl-phenyl}-2-methoxy-benzamide;

N-{3-[4-(1-Cyclopropyl-5-ethyl-1H-pyrazol-4-yl)-1,2,3-triazol-1-yl]-4-methyl-phenyl}-2-morpholin-4-yl-isonicotinamide;

5-tert-Butyl-N-{3-[4-(1-cyclopropyl-5-ethyl-1H-pyrazol-4-yl)-1,2,3-triazol-1-yl]-4-methyl-phenyl}-2-methyl-nicotinamide;

N-{3-[4-(1-Cyclopropyl-5-ethyl-1H-pyrazol-4-yl)-1,2,3-triazol-1-yl]-4-methyl-phenyl}-3-methanesulfonylamino-2-methoxy-5-(1-methyl-cyclopropyl)-benzamide;

5-tert-Butyl-N-{3-[4-(3-tert-butyl-2-methyl-3H-imidazol-4-yl)-1,2,3-triazol-1-yl]-4-methyl-phenyl}-3-methanesulfonylamino-2-methoxy-benzamide;

5-tert-Butyl-N-{3-[4-(3-tert-butyl-2-methyl-3H-imidazol-4-yl)-1,2,3-triazol-1-yl]-4-methyl-phenyl}-2-methoxy-benzamide;

5-tert-Butyl-N-{3-[4-(3-tert-butyl-2-methyl-3H-imidazol-4-yl)-1,2,3-triazol-1-yl]-4-methyl-phenyl}-3-cyano-2-methoxy-benzamide;

5-tert-Butyl-N-{3-[4-(3-tert-butyl-2-methyl-3H-imidazol-4-yl)-1,2,3-triazol-1-yl]-4-methyl-phenyl}-2-methyl-nicotinamide;

N-{3-[4-(3-tert-Butyl-2-methyl-3H-imidazol-4-yl)-1,2,3-triazol-1-yl]-4-methyl-phenyl}-2-morpholin-4-yl-isonicotinamide;

5-tert-Butyl-N-{3-[4-(2-cyclopropyl-3-methyl-3H-imidazol-4-yl)-1,2,3-triazol-1-yl]-4-methyl-phenyl}-3-methanesulfonylamino-2-methoxy-benzamide;

N-{3-[4-(2-Cyclopropyl-3-methyl-3H-imidazol-4-yl)-1,2,3-triazol-1-yl]-4-methyl-phenyl}-3-methanesulfonylamino-2-methoxy-5-(1-methyl-cyclopropyl)-benzamide;

5-tert-Butyl-N-{3-[4-(2-cyclopropyl-3-methyl-3H-imidazol-4-yl)-1,2,3-triazol-1-yl]-4-methyl-phenyl}-2-methoxy-benzamide;

5-tert-Butyl-3-cyano-N-{3-[4-(2-cyclopropyl-3-methyl-3H-imidazol-4-yl)-1,2,3-triazol-1-yl]-4-methyl-phenyl}-2-methoxy-benzamide;

5-tert-Butyl-N-{3-[4-(2-cyclopropyl-3-methyl-3H-imidazol-4-yl)-1,2,3-triazol-1-yl]-4-methyl-phenyl}-2-methyl-nicotinamide;

N-{3-[4-(2-Cyclopropyl-3-methyl-3H-imidazol-4-yl)-1,2,3-triazol-1-yl]-4-methyl-phenyl}-2-morpholin-4-yl-isonicotinamide;

N-{3-[4-(2-Cyclopropyl-3-methyl-3H-imidazol-4-yl)-1,2,3-triazol-1-yl]-4-methyl-phenyl}-3-morpholin-4-yl-benzamide;

N-{3-[4-(2-Cyclopropyl-3-methyl-3H-imidazol-4-yl)-1,2,3-triazol-1-yl]-4-methyl-phenyl}-3-fluoro-5-morpholin-4-yl-benzamide;

5-tert-Butyl-2-methyl-2H-pyrazole-3-carboxylic acid {3-[4-(2-cyclopropyl-3-methyl-3H-imidazol-4-yl)-1,2,3-triazol-1-yl]-4-methyl-phenyl}-amide;

5-tert-Butyl-2-p-tolyl-2H-pyrazole-3-carboxylic acid {3-[4-(2-cyclopropyl-3-methyl-3H-imidazol-4-yl)-1,2,3-triazol-1-yl]-4-methyl-phenyl}-amide;

2-Phenyl-cyclopropanecarboxylic acid {3-[4-(2-cyclopropyl-3-methyl-3H-imidazol-4-yl)-1,2,3-triazol-1-yl]-4-methyl-phenyl}-amide;

5-tert-Butyl-3-methanesulfonylamino-2-methoxy-N-{4-methyl-3-[4-(3-methyl-3H-imidazol-4-yl)-pyrazol-1-yl]-phenyl}-benzamide;

5-tert-Butyl-N-{3-[4-(2-cyclopropyl-3-methyl-3H-imidazol-4-yl)-pyrazol-1-yl]-4-methyl-phenyl}-3-methanesulfonylamino-2-methoxy-benzamide;

5-tert-Butyl-N-{3-[4-(2-tert-butyl-3-methyl-3H-imidazol-4-yl)-1,2,3-triazol-1-yl]-4-methyl-phenyl}-3-methanesulfonylamino-2-methoxy-benzamide;

5-tert-Butyl-N-{3-[4-(2-tert-butyl-3-methyl-3H-imidazol-4-yl)-1,2,3-triazol-1-yl]-4-methyl-phenyl}-2-methoxy-benzamide;

5-tert-Butyl-N-{3-[4-(2-tert-butyl-3-methyl-3H-imidazol-4-yl)-1,2,3-triazol-1-yl]-4-methyl-phenyl}-3-cyano-2-methoxy-benzamide;

N-{3-[4-(2-tert-Butyl-3-methyl-3H-imidazol-4-yl)-1,2,3-triazol-1-yl]-4-methyl-phenyl}-2-morpholin-4-yl-isonicotinamide;

N-{3-[4-(2-tert-Butyl-3-methyl-3H-imidazol-4-yl)-1,2,3-triazol-1-yl]-4-methyl-phenyl}-2-pyrrolidin-1-yl-isonicotinamide;

5-tert-Butyl-N-{3-[4-(2-tert-butyl-3-methyl-3H-imidazol-4-yl)-1,2,3-triazol-1-yl]-4-methyl-phenyl}-2-methyl-nicotinamide;

5-tert-Butyl-3-methanesulfonylamino-2-methoxy-N-{4-methyl-3-[4-(3-methyl-2-phenyl-3H-imidazol-4-yl)-1,2,3-triazol-1-yl]-phenyl}-benzamide;

5-tert-Butyl-2-methoxy-N-{4-methyl-3-[4-(3-methyl-2-phenyl-3H-imidazol-4-yl)-1,2,3-triazol-1-yl]-phenyl}-benzamide;

5-tert-Butyl-3-cyano-2-methoxy-N-{4-methyl-3-[4-(3-methyl-2-phenyl-3H-imidazol-4-yl)-1,2,3-triazol-1-yl]-phenyl}-benzamide;

5-tert-Butyl-2-methyl-N-{4-methyl-3-[4-(3-methyl-2-phenyl-3H-imidazol-4-yl)-1,2,3-triazol-1-yl]-phenyl}-nicotinamide;

N-{4-Methyl-3-[4-(3-methyl-2-phenyl-3H-imidazol-4-yl)-1,2,3-triazol-1-yl]-phenyl}-2-morpholin-4-yl-isonicotinamide;

1-[5-(5-tert-Butyl-3-methanesulfonylamino-2-methoxy-benzoylamino)-2-methyl-phenyl]-1H-1,2,3-triazole-4-carboxylic acid (2,2-dimethyl-propyl)-amide;

1-[5-(5-tert-Butyl-2-methoxy-benzoylamino)-2-methyl-phenyl]-1H-1,2,3-triazole-4-carboxylic acid (2,2-dimethyl-propyl)-amide;

1-[5-(5-tert-Butyl-3-cyano-2-methoxy-benzoylamino)-2-methyl-phenyl]-1H-1,2,3-triazole-4-carboxylic acid (2,2-dimethyl-propyl)-amide;

5-tert-Butyl-N-{3-[4-(2,2-dimethyl-propylcarbamoyl)-1,2,3-triazol-1-yl]-4-methyl-phenyl}-2-methyl-nicotinamide;

N-{3-[4-(2,2-Dimethyl-propylcarbamoyl)-1,2,3-triazol-1-yl]-4-methyl-phenyl}-2-morpholin-4-yl-isonicotinamide;

1-[5-(5-tert-Butyl-3-methanesulfonylamino-2-methoxy-benzoylamino)-2-methyl-phenyl]-1H-1,2,3-triazole-4-carboxylic acid ((R)-1-phenyl-ethyl)-amide;

1-[5-(5-tert-Butyl-2-methoxy-benzoylamino)-2-methyl-phenyl]-1H-1,2,3-triazole-4-carboxylic acid ((R)-1-phenyl-ethyl)-amide;

1-[5-(5-tert-Butyl-3-cyano-2-methoxy-benzoylamino)-2-methyl-phenyl]-1H-1,2,3-triazole-4-carboxylic acid ((R)-1-phenyl-ethyl)-amide;

N-{4-Methyl-3-[4-((R)-1-phenyl-ethylcarbamoyl)-1,2,3-triazol-1-yl]-phenyl}-2-morpholin-4-yl-isonicotinamide;

5-tert-Butyl-3-methanesulfonylamino-2-methoxy-N-{4-methyl-3-[4-(3-methyl-2-morpholin-4-yl-3H-imidazol-4-yl)-1,2,3-triazol-1-yl]-phenyl}-benzamide;

5-tert-Butyl-2-methoxy-N-{4-methyl-3-[4-(3-methyl-2-morpholin-4-yl-3H-imidazol-4-yl)-1,2,3-triazol-1-yl]-phenyl}-benzamide;

5-tert-Butyl-3-cyano-2-methoxy-N-{4-methyl-3-[4-(3-methyl-2-morpholin-4-yl-3H-imidazol-4-yl)-1,2,3-triazol-1-yl]-phenyl}-benzamide;

5-tert-Butyl-2-methyl-N-{4-methyl-3-[4-(3-methyl-2-morpholin-4-yl-3H-imidazol-4-yl)-1,2,3-triazol-1-yl]-phenyl}-nicotinamide;

N-{4-Methyl-3-[4-(3-methyl-2-morpholin-4-yl-3H-imidazol-4-yl)-1,2,3-triazol-1-yl]-phenyl}-2-morpholin-4-yl-isonicotinamide.

Methods of Use

In accordance with the invention, there are provided novel methods of using the compounds of the formula (I). The compounds disclosed therein effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds are useful for the treatment of diseases and conditions as described in the Background section, including the following conditions and diseases:

osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure. The compounds of the invention may also be useful for anticoagulant or fibrinolytic therapy (and the diseases or conditions related to such therapy) as described in the provisional application No. 60/403,422.

The compounds of the invention are also p38 Map kinase inhibitors, and therefore will be useful for treating oncological diseases and other cytokine mediated diseases and conditions related to p38 Map kinase as known in the art. Methods of assaying for p38 Map kinase activity can be perfomed by known methods. See for example Branger, J. et al, *The Journal of Immunology*, (2002), 168: 4070-4077, and the 46 references cited therein, each incorporated herein by reference in their entirety. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), hepatoblastoma, cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, Hodgkins lymphoma, cutaneous T-cell lymphoma, and lymphoma of the central nervous system.

Sarcomas include, but are not limited to sarcoma of the soft tissue, osteosarcoma, Ewings sarcoma, malignant fibrous histiocytoma, lymphosarcoma, angiosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

Plasma cell dyscrasias include, but are not limited to multiple myeloma, and Waldenstrom's macroglobulinemia.

These disorders have been well characterized in man, but also exist with a similar etiology in other mammals, and can be treated by pharmaceutical compositions of the present invention.

For therapeutic use, the compounds may be administered in any conventional dosage form in any conventional manner.

Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. Pat. No. 6,565,880, PCT/US 01/21860 and U.S. application Ser. No. 10/214,782, each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. Reference in this regard may also be made to US publication no. US 2003-0118575 A1. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Biological Assays

Molecular Assay

Binding affinities can be determined by using the thermal denaturation method (Kroe, R. R. et al. *J. Med. Chem.*, 2004, 24, 4669).

Inhibition of TNF Production in THP Cells

The inhibition of cytokine production can be observed by measuring inhibition of TNFα in lipopolysaccharide stimulated THP cells (for example, see W. Prichett et al., 1995, *J. Inflammation*, 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was non-sterile. Initial stock solutions were made in DMSO followed by dilution into RPMI 1640 2-fold higher than the desired final assay concentration. Confluent THP.1 cells ($2\times10^6$ cells/ml, final conc.; American Type Culture Company, Rockville, Md.) were added to 96 well polypropylene round bottomed culture plates (Costar 3790; sterile) containing 125 µl test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 µg/ml final; Siga L-2630, from *E. coli* serotype 0111.B4; stored as 1 mg/ml stock in endotoxin screened distilled $H_2O$ at −80° C.). Blanks (unstimulated) received $H_2O$ vehicle; final incubation volume was 250 µl. Overnight incubation (18-24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated $IC_{50}$ value is the concentration of the test compound that caused a 50% decrease in the maximal TNFα production.

Preferred compounds have an $IC_{50}<1$ uM in this assay.

Inhibition of Other Cytokines

By similar methods using peripheral blood monocytic cells, appropriate stimuli, and commercially available ELISA kits (or other method of detection such as radioimmunoassay), for a particular cytokine, inhibition of IL-1 beta, GM-CSF, IL-6 and IL-8 can be demonstrated for preferred compounds (for example, see J. C. Lee et al., 1988, *Int. J. Immunopharmacol.*, 10, 835).

All references disclosed in this application including patents, patent publications and literature citations are incorporated herein by reference in their entirety.

What is claimed is:

1. A compound of the formula (I)

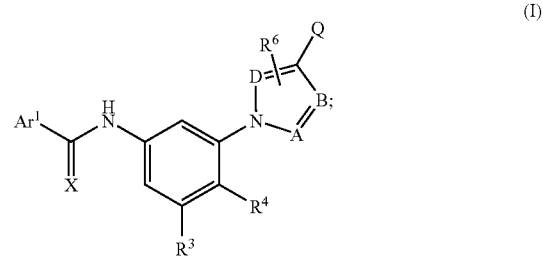

wherein:

$Ar^1$ is chosen from (i), (ii), (iii) and (iv) below:
i) a carbocycle independently substituted by one or more of $R^1$, $R^2$ and $R^x$,

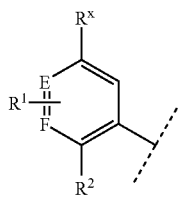

wherein one of E or F is nitrogen and the other is carbon, $R^1$ is covalently attached to either E or F, and when nitrogen is $N-R^1$ the double bond between E and F is not present;

(iii)

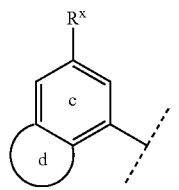

wherein c is a benzo ring fused to ring d which is a 5-7 membered heterocyclic ring optionally substituted by an oxo (=O) group and one to two R groups each independently being H or C1-3 alkyl;

(iv) a 5 membered nitrogen containing heteroaryl or heterocyclic ring optionally substituted by $R^1$ or $R^x$;

$R^1$ is chosen from hydrogen, $NO_2$, $-N(R^c)_2$, J-C(O)-N($R^c$)-, J-S(O)$_m$-N($R^c$)-, C1-6 alkylS(O)$_m$- or $R^1$ is chosen from C1-6 alkyl, C3-7 cylcoalkyl, C1-5 alkoxyl or C3-7 cycloalkoxyl, C1-5 alkylthiol or C3-7 cycloalkylthiol, C1-5 acyl, C1-5 alkoxycarbonyl, C1-5 acyloxy, C1-5 acylamino, C2-5 alkenyl, C2-5 alkynyl, heterocycle, aryl, heterocycleC1-6 alkyl, heteroaryl, heteroarylC1-6 alkyl and nitrile; each of the aforementioned where possible are optionally partially or fully halogenated or are optionally further substituted with alkylsulfonylamino, aminocarboxyl, alkoxyl, amino, alkylamino, dialkylamino, hydroxyl, oxo, nitro or nitrile;

$R^2$ is chosen from:

hydrogen, halogen, nitrile, C1-5 alkylS(O)$_m$-, arylS(O)$_m$, J-O-C(O)-O-, N($R^c$)$_2$-C(O)-(CH$_2$)$_n$-, C1-6 acetyl, aroyl, C1-6alkoxycarbonyl, C1-6 alkyl, C3-7cycloalkyl, C1-6 alkoxy, C3-5cycloalkoxy, C1-5 alkylC1-5 alkoxy, hydroxy, hydroxy C1-5 alkyl, and amino optionally mono- or di-substituted by C1-5 alkyl, aryl or aryl C1-5 alkyl; each of the aforementioned where possible are optionally partially or fully halogenated or are optionally further substituted with C1-3 alkyl, alkylsulfonylamino, alkoxyl, amino, alkylamino, dialkylamino, hydroxyl, oxo, nitro or nitrile;

each $R^x$ is chosen from C1-6 alkyl or C3-7 cycloalkyl each being optionally substituted by C1-3 alkyl and optionally partially or fully halogenated, C1-4 acyl, aroyl, C1-4 alkoxy, C1-5alkylS(O)$_m$-, each may optionally be partially or fully halogenated, halogen, C1-6 alkoxycarbonyl, carbocyclesulfonyl;

each $R^c$ is independently hydrogen or C1-5 alkyl;

D, A and B in

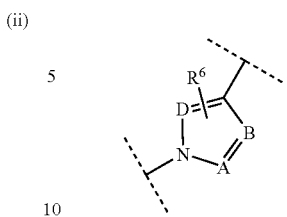

of the formula (I) is chosen from:

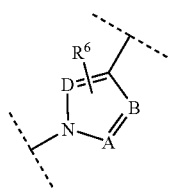

wherein the hydrogen atom is optionally replaced by $R^6$;

Q is $-C(O)-R^5$ or Het,

Het is a heterocyclic or heteroaryl ring wherein Het is optionally substituted by one to three $R^5$;

m is 0,1 or 2;

J is chosen from C1-10 alkyl and C3-7cycloalkyl each optionally substituted by $R^b$;

$R^3$, $R^4$, $R^6$, $R^7$ and $R^8$ are each independently chosen from hydrogen, halogen, C1-5 alkyl, C1-5 alkoxy, C1-5 alkylC1-5 alkoxy, hydroxy, hydroxy C1-5 alkyl or amino optionally mono- or di- substituted by C1-5 alkyl, aryl or aryl C1-5 alkyl;

$R^5$ is:

$R^a$, $-O-R^a$, $-S(O)_m-R^a$, $-N(R^a)_2$, $-C(O)-R^a$, $-NH(CR^7R^8)_n-R^a$, $N(R^a)_2-(CH_2)_{1-2}-(CR^7R^8)_n-R^a$, $-O(CR^7R^8)_n-R^a$, $-C(O)-O(CR^7R^8)_n-R^a$, $-C(O)(CR^7R^8)_n-R^a$ $C(O)C(O)R^a$, $-C(O)C(O)OR^a$, $-C(O)NHR^a$, and $-C(O)NH(CR^7R^8)_n-$, each optionally substituted by C1-3 alkyl, halogen or hydroxy, wherein n is 1-5;

$R^a$ and $R^b$ are each independently chosen from hydrogen, C1-6 alkyl, hydroxyC1-5 alkyl, C2-5 alkenyl, C2-5 alkynyl, carbocycle, carbocycleC0-2 alkyl, aryl, heterocycle, heteroaryl, C1-5 alkoxy, C1-5 alkylthio, amino, C1-5 alkylamino, C1-5 dialkylamino, arylamino, aryl C1-5 alkylamino, diarylamino, C1-5 acyl, C1-5 alkoxycarbonyl, C1-5 acyloxy, C1-5 acylamino, each of the aforementioned are optionally partially or fully halogenated, or $R^a$ and $R^b$ are chosen from C1-5 alkylsulphonylamino, hydroxy, oxo, halogen, $-CF_3$, $-CH_2-CF_3$, nitro and nitrile, wherein each carbocycle, heterocycle or heteroaryl for $R^a$ and $R^b$ is optionally substituted by amino, C1-3 alkyl, halogen or hydroxy;

and

X is O or S or a pharmaceutically acceptable salt thereof.

2. The compound according to claim 1 and wherein
Q is Het;
Het is

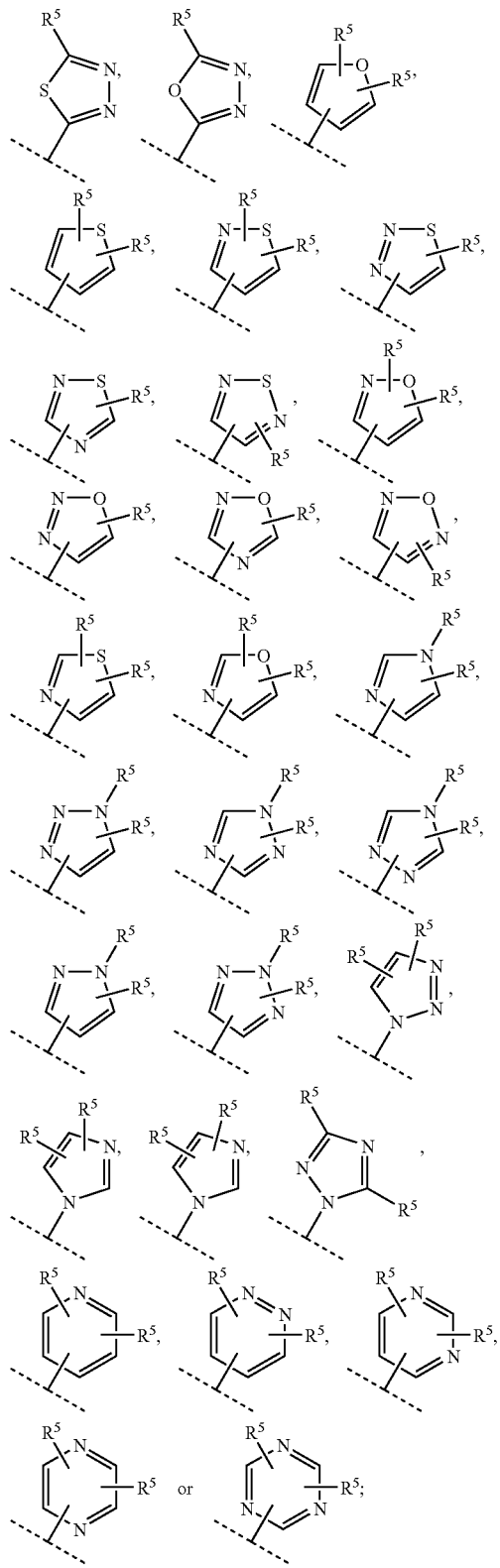

J is chosen from C1-10 alkyl, aryl and C3-7 cycloalkyl each optionally substituted by $R^b$;

$R^2$ is independently chosen from hydrogen, J-O—C(O)—O—, C1-6 alkoxy, C1-6 alkyl, C1-6 acetyl, aroyl, halogen, methoxycarbonyl, phenylsulfonyl, C1-5 alkyl S(O)$_m$— and C3-7 cycloalkyl optionally substituted by C1-3 alkyl, each $R^2$ where possible may be optionally partially or fully halogenated;

$R^1$ is chosen from H, C1-6 alkyl, phenyl, C1-5 alkyl S(O)$_m$—, J-S(O)$_m$—N($R^c$)—, C1-5 alkoxyl, C1-5 alkylthiol , NH$_2$—C(O)—(CH$_2$)$_n$—, ($R^c$)$_2$N C1-6 alkyl, C1-5 acylNH—, —NH$_2$, —NO$_2$, heteroaryl chosen from pyrazole, triazole, imidazole and tetrazole, and nitrile;

ring d is a 5-6 membered heterocyclic ring such that rings c and d fuse to form the following:

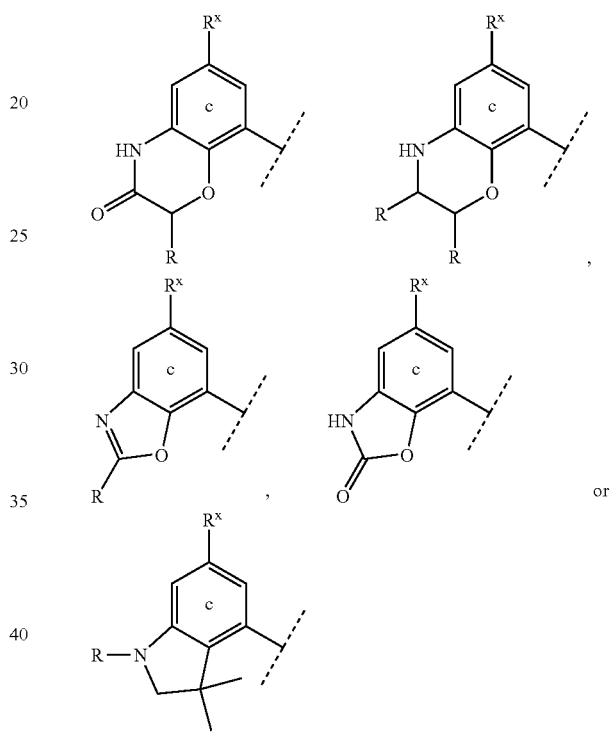

where each R is independently hydrogen or C1-3 alkyl;
if Ar is (iv) then Ar is pyrazolyl optionally substituted by $R^1$ or $R^x$;
$R^3$ and $R^4$ are each independently chosen from hydrogen, C1-3 alkoxy, C1-3 alkyl and halogen;
n is 1-4;
$R^a$ and $R^b$ are each independently chosen from hydrogen, C1-6 alkyl, C2-5 alkenyl, C2-5 alkynyl, C3-8 cycloalkylC0-2 alkyl, aryl, C1-5 alkoxy, C1-5 alkylthio, amino, C1-5 alkylamino, C1-5 dialkylamino, arylamino, C1-5 acyl, C1-5 alkoxycarbonyl, C1-5 acyloxy, C1-5 acylamino, aryl C1-5 alkylamino, C1-5 alkylsulphonylamino, hydroxy, halogen, —CF$_3$, —CH$_2$—CF$_3$ nitro, nitrile,
or $R^a$ and $R^b$ are chosen from; heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, homopiperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, aziridinyl, pentamethylene sulfide, pentamethylene sulfoxide, pentamethylene sulfone, tetramethylene sulfide, tetramethylene sulfoxide and tetramethylene sulfone
and heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl; wherein each aryl, heterocycle or heteroaryl for $R^a$ and $R^b$ is optionally substituted by amino, C1-3 alkyl, halogen or hydroxy;
and X is O.

3. The compound according to claim 2 and wherein $Ar^1$ is chosen from (i), (ii) and (iv);
wherein if $Ar^1$ is (iv) then $Ar^1$ is

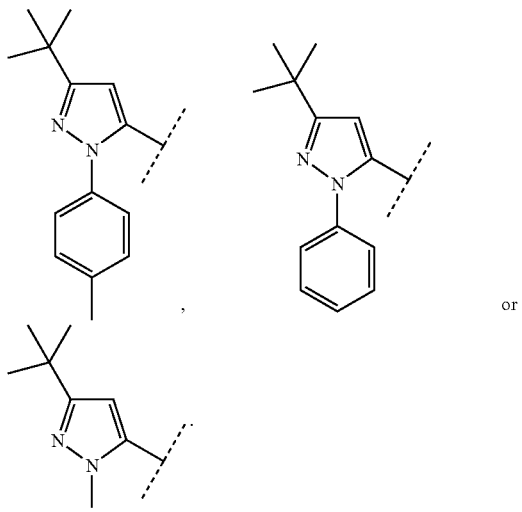

,                              or $R^5$ is:
a) $R^a$, —O—$R^a$, —S(O)$_m$—$R^a$, —N($R^a$)$_2$, N($R^a$)$_2$—(CH$_2$)$_{1-2}$—, —NH(CR$^7$R$^8$)$_n$—$R^a$, —(CR$^7$R$^8$)$_n$—$R^a$ or —O(CR$^7$R$^8$)$_n$—$R^a$;
or $R^5$ is:
b) —C(O)—$R^a$, —C(O)—O(CR$^7$R$^8$)$_n$—$R^a$, —C(O)(CR$^7$R$^8$)$_n$—$R^a$, —C(O)NHR$^a$, —C(O)NH(CR$^7$R$^8$)$_n$—, —C(O)C(O)R$^a$ or —C(O)C(O)OR$^a$;
each of the above $R^5$ is optionally substituted by C1-3 alkyl, halogen or hydroxyl, and wherein n is 1-3.

4. The compound according to claim 3 and wherein $Ar^1$ is:

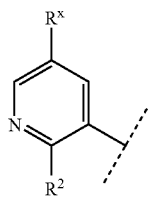

or $Ar^1$ is cyclopropyl, cyclobutyl, phenyl, naphthyl, tetrahydronaphthyl, indanyl and indenyl each independently substituted with one or more of $R^1$, $R^x$, and $R^2$;

$R^1$ is nitrile, NO$_2$, NH$_2$, C1-3acylNH—, J-S(O)$_m$—N(R$^c$)— where J is C1-10 alkyl, or $R^1$ is

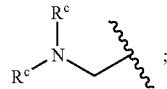

;

$R^2$ is independently chosen from C1-6 alkyl, C1-6 alkylS(O)$_m$—, C1-3 alkoxy and C3-6 cycloalkyl optionally substituted by C1-3 alkyl , each may optionally be partially or fully halogenated;
$R^3$ and $R^4$ are each independently chosen from hydrogen, C1-3 alkyl, fluoro and chloro;
$R^6$ is chosen from hydrogen and amino;
n is 1-2;
$R^a$ and $R^b$ are each independently chosen from hydrogen, C1-6 alkyl, C3-7 cycloalkylC0-2 alkyl, aryl, C1-5 alkoxy, amino, C1-5 alkylamino, C1-5 dialkylamino, arylamino, aryl C1-5 alkylamino, C1-3 acyl, C1-5 alkoxycarbonyl, C1-5 acyloxy, C1-5 acylamino, C1-5 sulphonylamino, hydroxy, halogen, —CF$_3$, —CH$_2$—CF$_3$ nitro, nitrile;
or $R^a$ is chosen from pyrrolidinyl, pyrrolinyl, morpholinyl, thiomorpholinyl, thiomorpholinyl sulfoxide, thiomorpholinyl sulfone, piperidinyl, piperazinyl, homopiperazinyl, piperidinonyl, tetrahydropyrimidonyl, aziridinyl, isoxazolyl, oxazolyl, thiazolyl, thiadiazolyl, tetrazolyl, pyrazolyl, pyrrolyl, imidazolyl, pyridinyl, pyrimidinyl, pyrazinyl and pyridazinyl; wherein each aryl, heterocycle or heteroaryl for $R^a$ and $R^b$ is optionally substituted by amino, C1-3 alkyl, halogen or hydroxy.

5. The compound according to claim 4 and wherein $Ar^1$ is

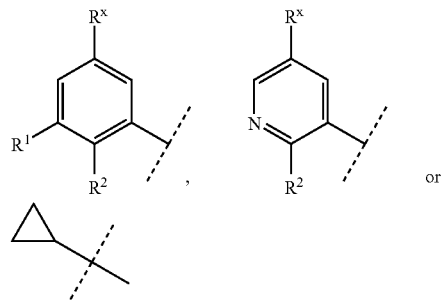

substituted by one or more of $R^1$, $R^2$ and $R^x$;
$R^1$ is:
J-S(O)$_2$—NH—, where J is C1-5 alkyl,
or $R^1$ is nitrile, NO$_2$, NH$_2$ or C1-3acylNH—;
wherein $R^x$=$R^2$ each are independently chosen from C1-5 alkyl, C1-5 alkylS(O)$_m$—, C1-4 alkoxy and and C3-5 cycloalkyl optionally substituted by C1-2 alkyl, each may optionally be partially or fully halogenated;
$R^8$ is hydrogen, methyl, ethyl, CH$_2$OH and CH$_2$OCH$_3$.

6. The compound according to claim 5 and wherein $R^a$ is chosen from hydrogen, C1-6 alkyl, C3-6 cycloalkylC0-2 alkyl, phenyl, C1-5 alkoxy, amino, C1-5 alkylamino, C1-5 dialkylamino, arylamino, aryl C1-5alkylamino, C1-5 acyl, C1-5 alkoxycarbonyl, C1-5 acyloxy, C1-5 acylamino, hydroxy, halogen, —CF$_3$, —CH$_2$—CF$_3$;

or R<sup>a</sup> is chosen from morpholinyl, thiomorpholinyl, thiomorpholinyl sulfoxide, thiomorpholinyl sulfone, piperazinyl, homopiperazinyl, pyrrolidinyl, piperidinyl, piperidinonyl, pyrimidinyl, pyridinyl, pyrazinyl and pyridazinyl wherein each phenyl, heterocycle or heteroaryl for R<sup>a</sup> is optionally substituted by amino, C1-3 alkyl, halogen or hydroxy.

7. The compound according to claim 6 and wherein

R<sup>a</sup> is chosen from hydrogen, C1-6 alkyl, C3-6 cycloalkyl, phenyl, C1-5 alkoxy, C1-5 alkoxycarbonyl, amino, C1-5 alkylamino, C1-5 dialkylamino, arylamino, aryl C1-5 alkylamino, C1-5 acyloxy, C1-5 acylamino, hydroxy, halogen, —CF$_3$, —CH$_2$—CF$_3$;

or R<sup>a</sup> is chosen from morpholinyl, piperidinyl piperazinyl, homopiperazinyl, pyrrolidinyl and pyridinyl wherein each phenyl, heterocycle or heteroaryl for R<sup>a</sup> is optionally substituted by amino, C1-3 alkyl, halogen or hydroxy.

8. The compound according to claim 7 and wherein

Het is;

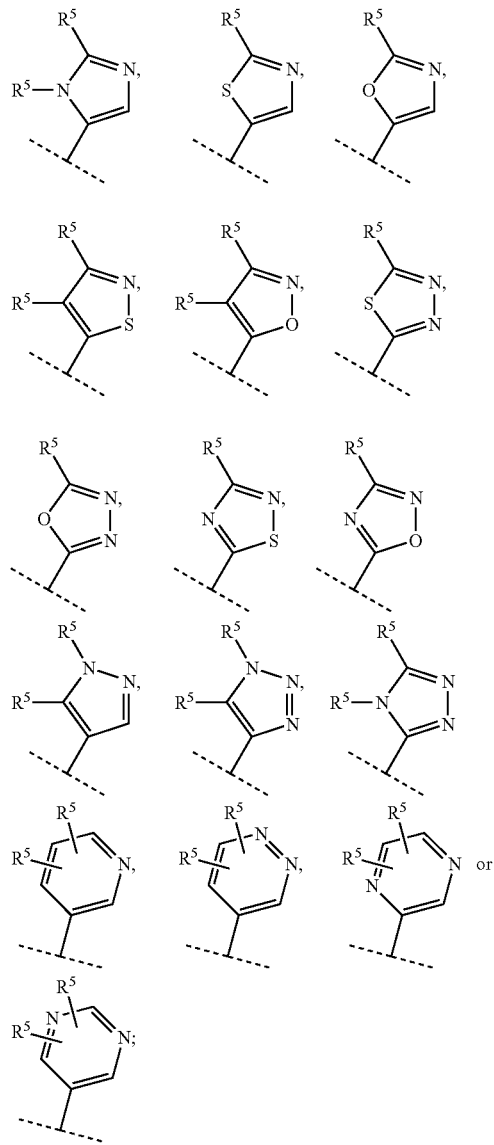

Ar$^1$ is

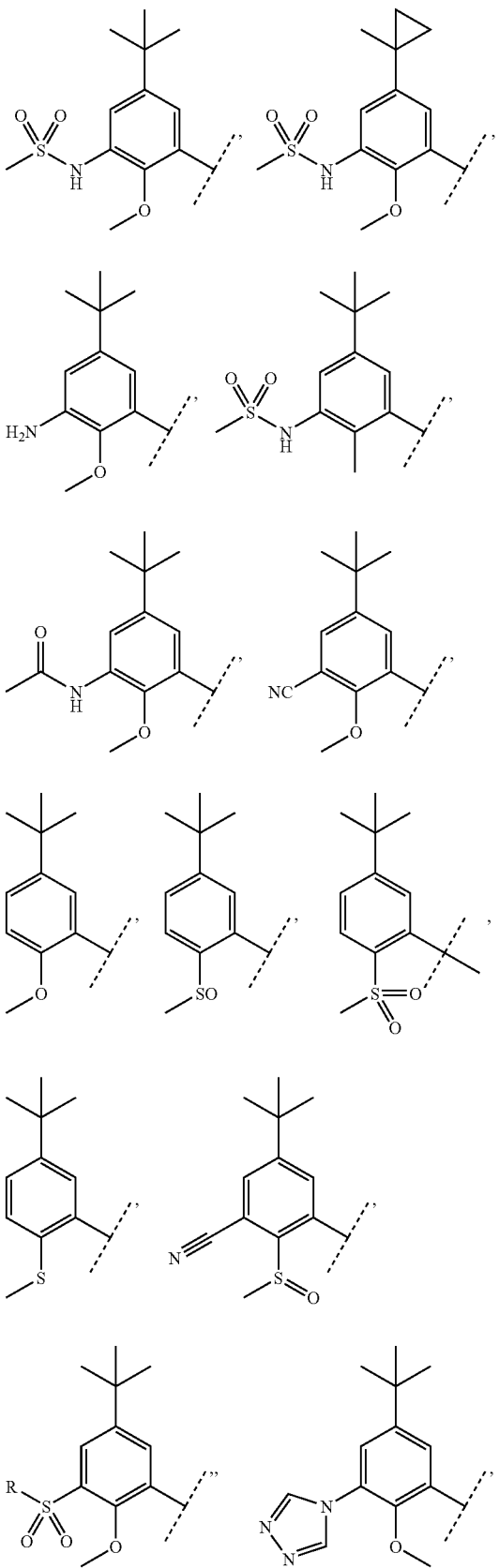

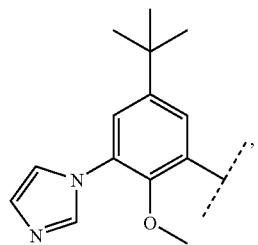
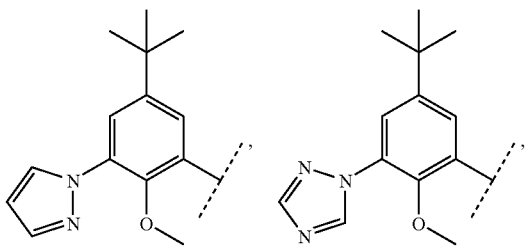
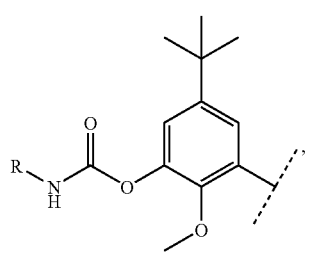
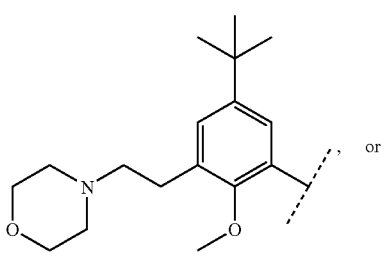
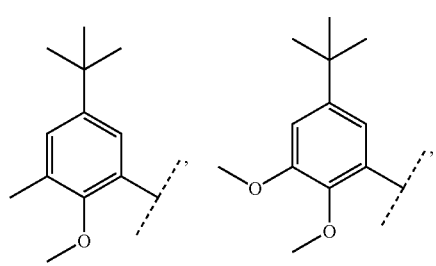
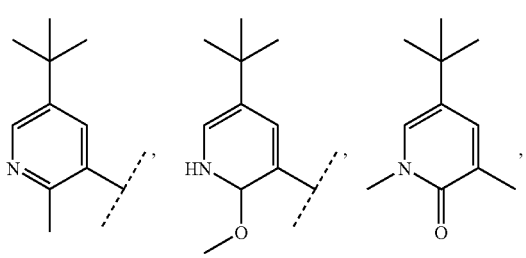
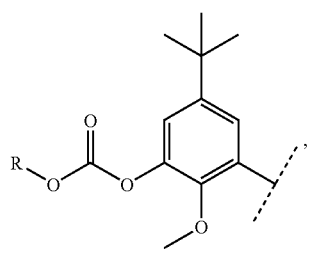
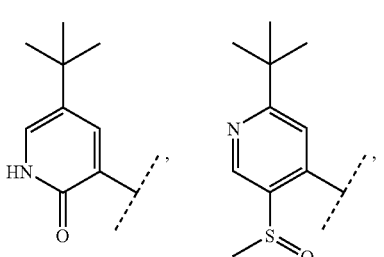
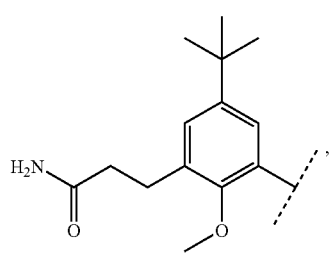
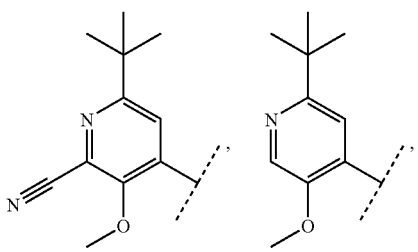
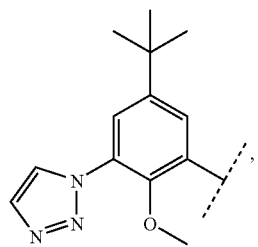
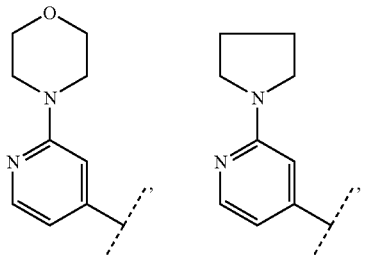

-continued

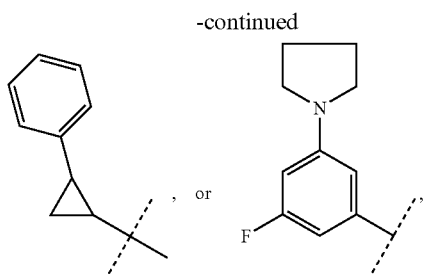

where each R is independently hydrogen or C1-3 alkyl;
$R^5$ is:

C1-5 alkyl, C3-6 cycloalkyl, $N(R^a)_2(CH_2)_{1-2}$—, halogen, C1-3 alkoxy, hydroxy, —$N(R^a)_2$, —$CF_3$, —$CH_2$—$CF_3$, aryl, —$S(O)_m$—$R^a$, —$NH(CR^7R^8)_n$—$R^a$ or —$(CR^7R^8)_n$—$N(R^a)_2$ each optionally substituted by C1-3 alkyl, halogen or hydroxy, or $R^5$ is —$C(O)R^a$, —$C(O)C(O)R^a$, —$C(O)NHR^a$, $R^a$ is chosen from hydrogen, morpholinyl, piperidinyl, piperazinyl, pyrrolidinyl, pyridinyl, $C_{1-5}$ mono or dialkylamino, arylamino, C3-6cylcoalkyl, C1-5 alkyl and C1-3 alkoxy wherein each phenyl or heterocycle for $R^a$ is optionally substituted by amino, C1-3 alkyl, halogen or hydroxyl.

9. The compound according to claim 1 wherein when then Het is

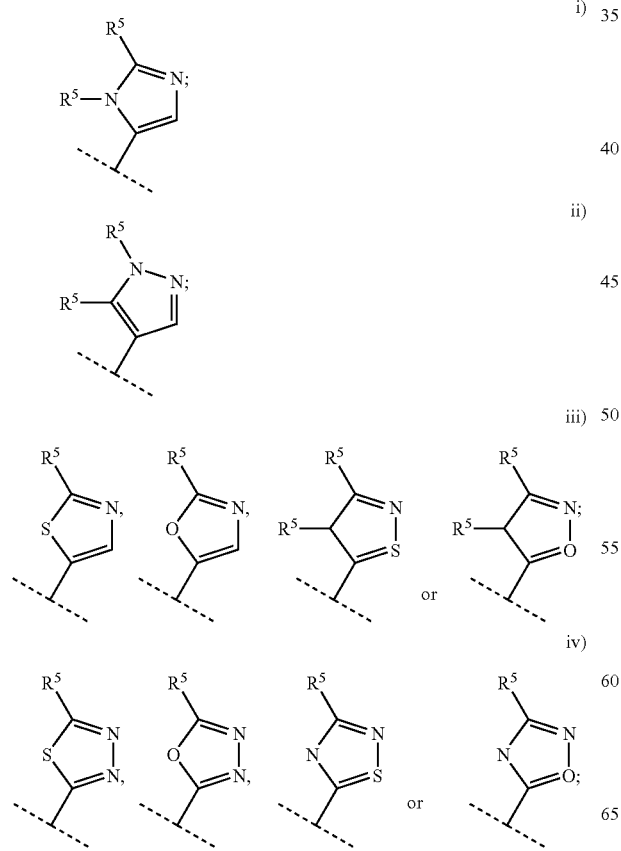

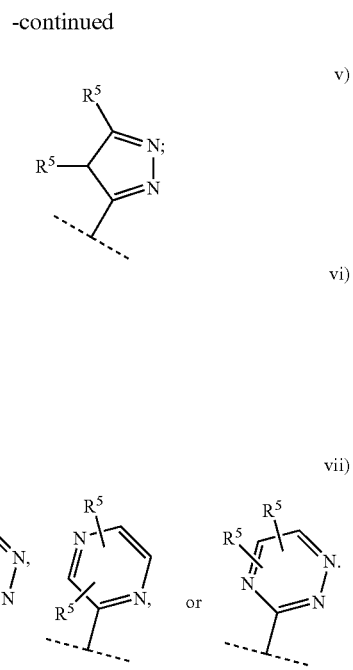

10. The compound according to claim 1 and wherein
Q is —$C(O)$—$R^5$;
J is chosen from C1-10 alkyl, aryl and C3-7 cycloalkyl each optionally substituted by $R^b$;
$R^2$ is independently chosen from hydrogen, J-O—C(O)—O—, C1-6 alkoxy, C1-6 alkyl, C1-6 acetyl, aroyl, halogen, methoxycarbonyl, phenylsulfonyl, C1-5 alkyl $S(O)_m$— and C3-7 cycloalkyl optionally substituted by C1-3 alkyl, each $R^2$ where possible may be optionally partially or fully halogenated;
$R^1$ is chosen from H, C1-6 alkyl, phenyl, C1-5 alkyl $S(O)_m$—, J-$S(O)_m$—$N(R^c)$—, C1-5 alkoxyl, C1-5 alkylthiol, $NH_2$—$C(O)$—$(CH_2)_n$—, $(R^c)_2N$ C1-6 alkyl, C1-5 acylNH—, —$NH_2$, —$NO_2$, heteroaryl chosen from pyrazole, triazole, imidazole and tetrazole, and nitrile;
ring d is a 5-6 membered heterocyclic ring such that rings c and d fuse to form the following:

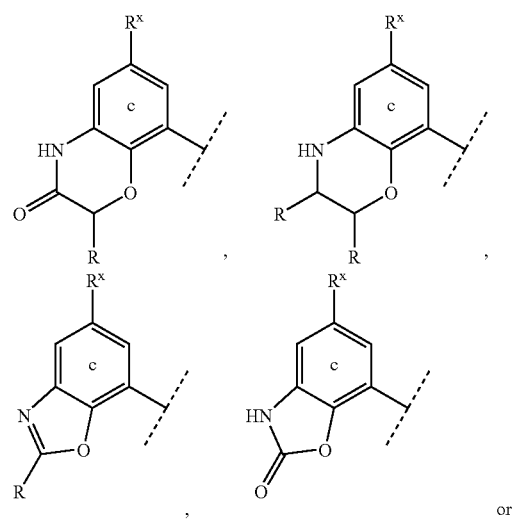

-continued

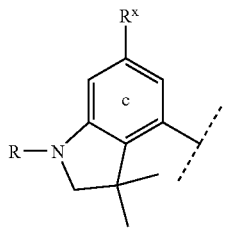

where each R is independently hydrogen or C1-3 alkyl;
if Ar is (iv) then Ar is pyrazolyl optionally substituted by $R^1$ or $R^x$;

$R^3$ and $R^4$ are each independently chosen from hydrogen, C1-3 alkoxy, C1-3 alkyl and halogen;

n is 1-4;

$R^a$ and $R^b$ are each independently chosen from hydrogen, C1-6 alkyl, C2-5 alkenyl, C2-5 alkynyl, C3-8 cycloalkylC0-2 alkyl, aryl, C1-5 alkoxy, C1-5 alkylthio, amino, C1-5 alkylamino, C1-5 dialkylamino, arylamino, C1-5 acyl, C1-5 alkoxycarbonyl, C1-5 acyloxy, C1-5 acylamino, aryl C1-5alkylamino, C1-5 alkylsulphonylamino, hydroxy, halogen, —$CF_3$, —$CH_2$—$CF_3$ nitro, nitrile, or $R^a$ and $R^b$ are chosen from; heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, homopiperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, aziridinyl, pentamethylene sulfide, pentamethylene sulfoxide, pentamethylene sulfone, tetramethylene sulfide, tetramethylene sulfoxide and tetramethylene sulfone and heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl; wherein each aryl, heterocycle or heteroaryl for $R^a$ and $R^b$ is optionally substituted by amino, C1-3 alkyl, halogen or hydroxy;

and X is O.

11. The compound according to claim 10 and wherein $Ar^1$ is chosen from (i), (ii) and (iv);
wherein if $Ar^1$ is (iv) then $Ar^1$ is

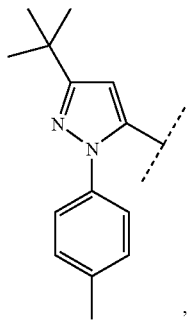,

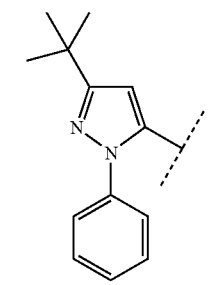 or

-continued

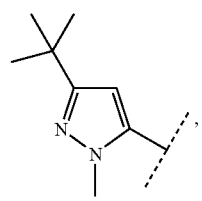, $R^5$ is:
a) $R^a$, —O—$R^a$, —S(O)$_m$—$R^a$, —N($R^a$)$_2$, N($R^a$)$_2$—(CH$_2$)$_{1-2}$—, —NH(CR$^7$R$^8$)$_n$—$R^a$, —(CR$^7$R$^8$)$_n$—$R^a$ or —O(CR$^7$R$^8$)$_n$—$R^a$;

or $R^5$ is:
b) —C(O)—$R^a$, —C(O)—O(CR$^7$R$^8$)$_n$—$R^a$, —C(O)(CR$^7$R$^8$)$_n$—$R^a$, —C(O)NHR$^a$, —C(O)NH(CR$^7$R$^8$)$_N$—, —C(O)C(O)R$^a$ or —C(O)C(O)OR$^a$;

each of the above $R^5$ is optionally substituted by C1-3 alkyl, halogen or hydroxyl, and wherein n is 1-3.

12. The compound according to claim 11 and wherein $Ar^1$ is

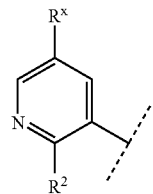

or $Ar^1$ is cyclopropyl, cyclobutyl, phenyl, naphthyl, tetrahydronaphthyl, indanyl and indenyl each independently substituted with one or more of $R^1$, $R^x$, and $R^2$;

$R^1$ is nitrile, $NO_2$, $NH_2$, C1-3acylNH—, J-S(O)$_m$—N(R$^c$)— where J is C1-10 alkyl, or $R^1$ is

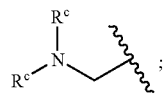;

$R^2$ is independently chosen from C1-6 alkyl, C1-6 alkylS(O)$_m$—, C1-3 alkoxy and C3-6 cycloalkyl optionally substituted by C1-3 alkyl, each may optionally be partially or fully halogenated;

$R^3$ and $R^4$ are each independently chosen from hydrogen, C1-3 alkyl, fluoro and chloro;

$R^6$ is chosen from hydrogen and amino;

n is 1-2;

$R^a$ and $R^b$ are each independently chosen from hydrogen, C1-6 alkyl, C3-7 cycloalkylC0-2 alkyl, aryl, C1-5 alkoxy, amino, C1-5 alkylamino, C1-5 dialkylamino, arylamino, aryl C1-5 alkylamino, C1-3 acyl, C1-5 alkoxycarbonyl, C1-5 acyloxy, C1-5 acylamino, C1-5 sulphonylamino, hydroxy, halogen, —$CF_3$, —$CH_2$—$CF_3$ nitro, nitrile;

or $R^a$ is chosen from pyrrolidinyl, pyrrolinyl, morpholinyl, thiomorpholinyl, thiomorpholinyl sulfoxide, thiomorpholinyl sulfone, piperidinyl, piperazinyl, homopiperazinyl, piperidinonyl, tetrahydropyrimidonyl, aziridinyl, isoxazolyl, oxazolyl, thiazolyl, thiadiazolyl, tetrazolyl, pyrazolyl, pyrrolyl, imidazolyl, pyridinyl, pyrimidinyl, pyrazinyl and pyridazinyl ; wherein each aryl, heterocycle or heteroaryl for $R^a$ and $R^b$ is optionally substituted by amino, C1-3 alkyl, halogen or hydroxy.

13. The compound according to claim 12 and wherein $Ar^1$ is

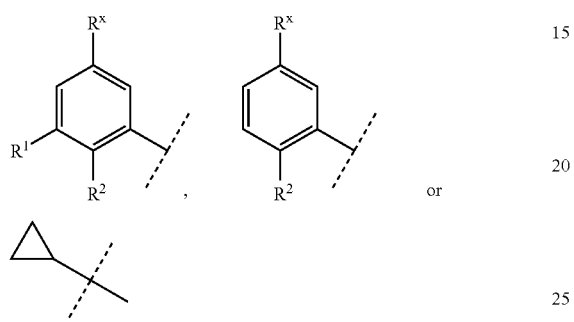

substituted by one or more of $R^1$, $R^2$ and $R^x$;

$R^1$ is:

J-S(O)$_2$—NH—, where J is C1-5 alkyl, or $R^1$ is nitrile, NO$_2$, NH$_2$ or C1-3acylNH—;

wherein $R^x$=$R^2$ each are independently chosen from C1-5 alkyl, C1-5 alkylS(O)$_m$—, C1-4 alkoxy and and C3-5 cycloalkyl optionally substituted by C1-2 alkyl, each may optionally be partially or fully halogenated;

$R^8$ is hydrogen, methyl, ethyl, CH$_2$OH and CH$_2$OCH$_3$.

14. The compound according to claim 13 and wherein $R^a$ is chosen from hydrogen, C1-6 alkyl, C3-6 cycloalkylC0-2 alkyl, phenyl, C1-5 alkoxy, amino, C1-5 alkylamino, C1-5 dialkylamino, arylamino, aryl C1-5alkylamino, C1-3 acyl, C1-5 alkoxycarbonyl, C1-5 acyloxy, C1-5 acylamino, hydroxy, halogen, —CF$_3$, —CH$_2$—CF$_3$;

or $R^a$ is chosen from morpholinyl, thiomorpholinyl, thiomorpholinyl sulfoxide, thiomorpholinyl sulfone, piperazinyl, homopiperazinyl, pyrrolidinyl, piperidinyl, piperidinonyl, pyridinyl, pyrimidinyl, pyrazinyl and pyridazinyl wherein each phenyl, heterocycle or heteroaryl for $R^a$ is optionally substituted by amino, C1-3 alkyl, halogen or hydroxy.

15. The compound according to claim 14 and wherein $R^a$ is chosen from hydrogen, C1-6 alkyl, C3-6 cycloalkyl, phenyl, C1-5 alkoxy, C1-5 alkoxycarbonyl, amino, C1-5 alkylamino, C1-5 dialkylamino, arylamino, aryl C1-5 alkylamino, C1-5 acyloxy, C1-5 acylamino, hydroxy, halogen, —CF$_3$, —CH$_2$—CF$_3$;

or $R^a$ is chosen morpholinyl, piperidinyl piperazinyl, homopiperazinyl, pyrrolidinyl and pyridinyl wherein each phenyl, heterocycle or heteroaryl for $R^a$ is optionally substituted by amino, C1-3 alkyl, halogen or hydroxy.

16. The compound according to claim 15 and wherein $Ar^1$ is

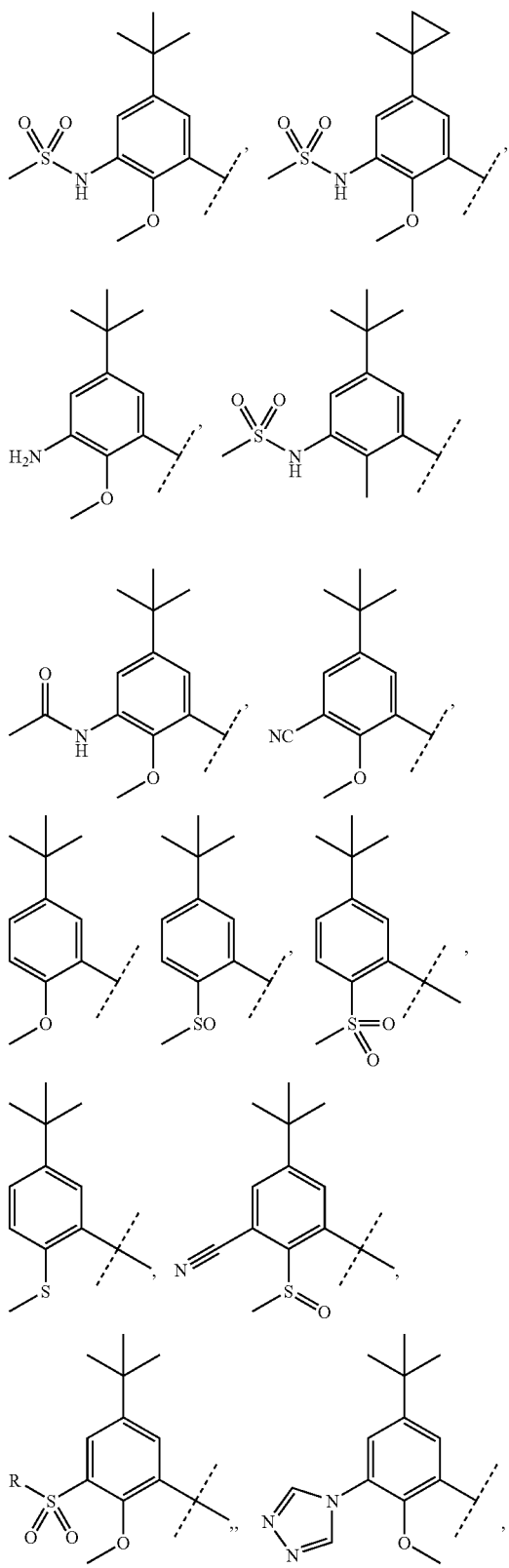

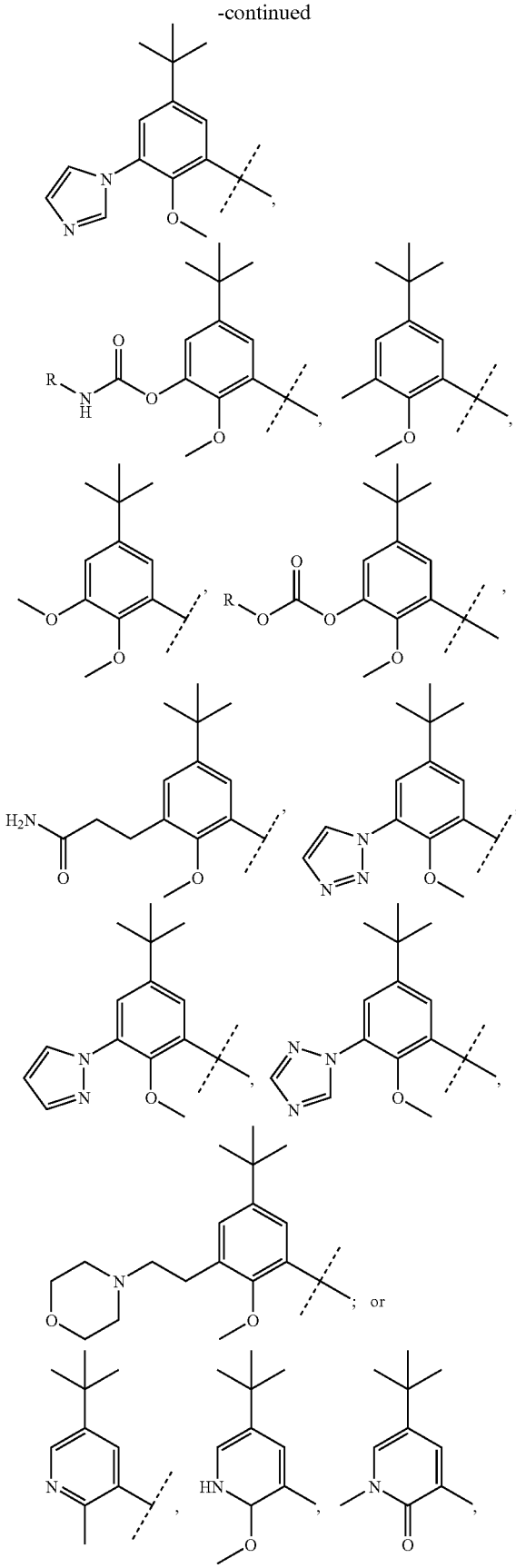

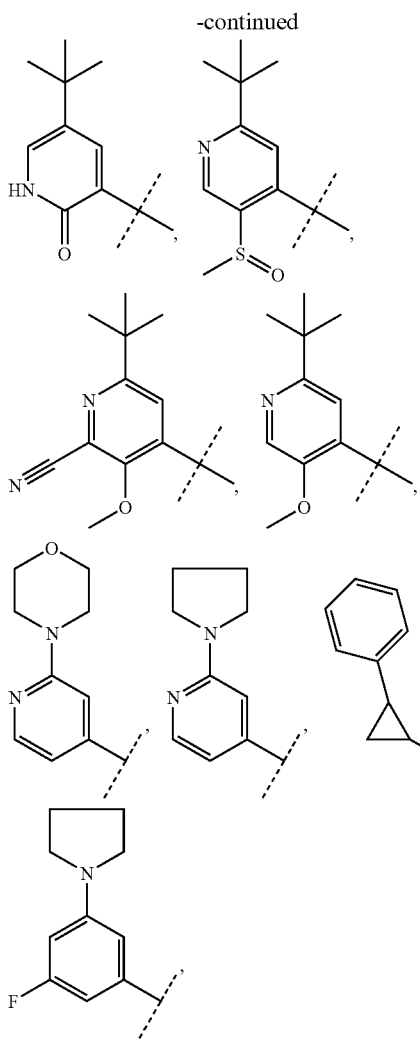

wherein R is independently hydrogen or C1-3 alkyl;

R⁵ is:

C1-5 alkyl, C3-6 cycloalkyl, N(Rᵃ)₂(CH₂)₁₋₂—, halogen, C1-3 alkoxy, hydroxy, —N(Rᵃ)₂, —CF₃, —CH₂—CF₃, aryl, S(O)ₘ—Rᵃ, —NH(CR⁷R⁸)ₙ—Rᵃ or —(CR⁷R⁸)ₙ—N(Rᵃ)₂ each optionally substituted by C1-3 alkyl, halogen or hydroxy, or R⁵ is —C(O)Rᵃ, —C(O)C(O)Rᵃ, —C(O)NHRᵃ, Rᵃ is chosen from hydrogen, phenyl, morpholinyl, piperidinyl, piperazinyl, pyrrolidinyl, pyridinyl, C₁₋₅ mono or dialkylamino, arylamino, C3-6cylcoalkyl, C1-5 alkyl and C1-3 alkoxy wherein each phenyl or heterocycle for Rᵃ is optionally substituted by amino, C1-3 alkyl, halogen or hydroxyl.

17. The compound according to claim 1 wherein Q is:

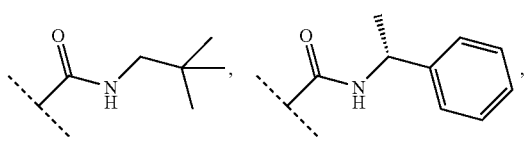

-continued
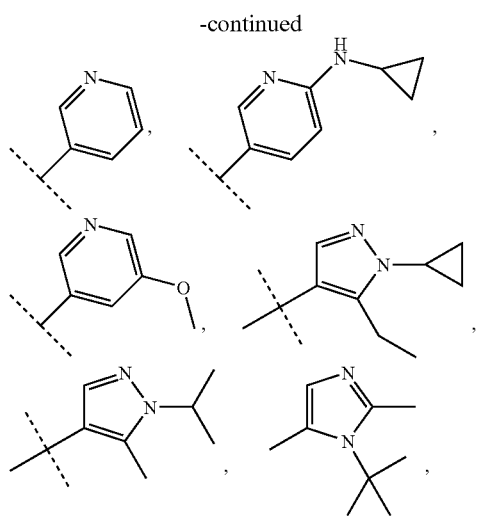
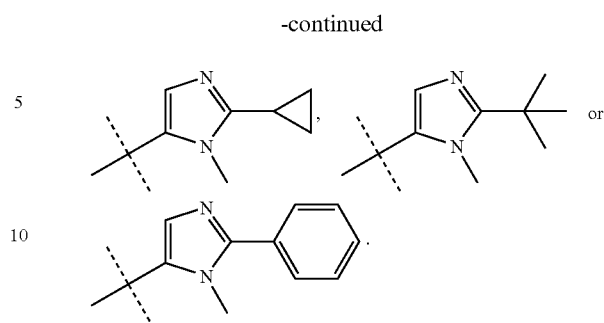
18. A pharmaceutical composition containing a pharmaceutically effective amount of a compound according to claim 1 and one or more pharmaceutically acceptable carrier and/or adjuvant.
* * * * *